United States Patent
Ornelis et al.

(10) Patent No.: US 11,608,326 B2
(45) Date of Patent: Mar. 21, 2023

(54) SYNTHETIC RECEPTORS FOR IONOPHORIC COMPOUNDS

(71) Applicant: Universiteit Gent, Ghent (BE)

(72) Inventors: Vincent Ornelis, Zevekote (BE); Annemieke Madder, Massemen (BE); Sarah de Saeger, Aalst (BE); Andreja Rajkovic, Ghent (BE); Benedikt Sas, Stekene (BE)

(73) Assignee: Universiteit Gent, Ghent (BE)

( * ) Notice: Subject to any disclaimer, the term of this patent is extended or adjusted under 35 U.S.C. 154(b) by 48 days.

(21) Appl. No.: 16/969,290

(22) PCT Filed: Feb. 27, 2019

(86) PCT No.: PCT/EP2019/054829
§ 371 (c)(1),
(2) Date: Aug. 12, 2020

(87) PCT Pub. No.: WO2019/166475
PCT Pub. Date: Sep. 6, 2019

(65) Prior Publication Data
US 2021/0009569 A1    Jan. 14, 2021

(30) Foreign Application Priority Data
Feb. 27, 2018 (EP) .................... 18158911

(51) Int. Cl.
C07D 403/14    (2006.01)
C07D 519/00    (2006.01)
C07D 409/14    (2006.01)

(52) U.S. Cl.
CPC ......... *C07D 403/14* (2013.01); *C07D 409/14* (2013.01); *C07D 519/00* (2013.01)

(58) Field of Classification Search
CPC ............... C07D 403/14; C07D 409/14; C07D 519/00
USPC ...................................................... 514/411
See application file for complete search history.

(56) References Cited

PUBLICATIONS

International Search Report and Written Opinion pertaining to PCT/EP2019/054829, dated Apr. 30, 2019.
European Search Report pertaining to corresponding European Patent Application No. 18158911.0, dated Jun. 28, 2018.
Santini et al., "Overview of Analytical Methods for Beauvericin and Fusaproliferin in Food Matrices", Analytical and Bioanalytical Chemistry, 2009, 1253-1260.
Maragos et al., "Recent Advances in the 1-15 Development of Novel Materials for Mycotoxin Analysis", Analytical and Bioanalytical Chemistry, 2009, 1205-1213.
Fan Yang et al., "Reversible Adsorption and Separation of Chlorocarbons and BTEX Based on Cu(II)-metal Organic Framework", Crystengcomm, 2015, 4102-4109.
Ornelis et al., "Development of a Synthetic Receptor for the Food Toxin Beauvericin: A Tale of Carbazole and Steroids", Organic Letters, 2018, 6368-6371.
Bernard, et al., "Macrocyclic Diketopiperazine Receptors: Effect of Macrocyclization on the Binding Properties of Two-Armsed Receptors", Organic Letters, vol. 9, No. 21, pp. 4283-4286, 2007.
Chang, et al., Stereoselective Recognition of Tripeptides Guided by Encoded Library Screening: Construction of Chiral Macrocyclic Tetraamide Ruthenium Receptor for Peptide Sensing, J. Org. Chem., pp. 2026-2032, 2005.
Gefen, et al., "The efftect of haptens on protein-carrier immunogenicity", Immunology, pp. 116-126, 2014.
Henley, et al., "Synthesis and binding properties of a macrobicyclic receptor for N-protected peptides with a carboxylic acid terminus", J. Chem. Soc., pp. 1021-1031, 2000.
Maragos, "Biosensors for mycotoxin analysis: recent developments and future prospects", World Mycotoxin Journal, pp. 221-238, May 2009.
O'Kennedy, et al., "A Review of Enzyme-Immunoassay and a Description of a Competitive Enzyme-Linked Immunosorbent Assay for the Detection of Immunoglobulin Concentrations", Biochemical Education, pp. 136-140, 1990.
Tonshin, et al., "The Fusarium mycotoxins enniatins and beauvericin cause mitochondrial dysfunction by affecting the mitochondrial volume regulation, oxidative phosphorylation and ion homeostasis", Toxicology, pp. 49-57, 2010.
Santini, et al., "Overview of analytical methods for beauvericin and fusaproliferin in food matrices", Anal Bioanal Chem., vol. 395, pp. 1253-1260, 2009.

*Primary Examiner* — Kristin A Vajda
(74) *Attorney, Agent, or Firm* — Dinsmore & Shohl, LLP

(57) ABSTRACT

The present invention relates to synthetic receptors for ionophoric compounds, such as ionophoric toxins. Hence, the invention provides synthetic molecules capable of binding different ionophoric compounds, thereby being suitable for use in the detection, isolation and detoxification of such ionophoric compounds. The present invention further provides the use of such synthetic receptors in human and veterinary medicine, such as in the diagnosis, prevention and/or treatment of disorders caused by such ionophoric compounds. Finally, the invention provides methods of preparing such synthetic receptors for ionophoric compounds.

16 Claims, 6 Drawing Sheets

Receptor V4 : n = 2
Receptor V3: n = 5

SYNTHETIC RECEPTORS FOR IONOPHORIC COMPOUNDS

FIELD OF THE INVENTION

The present invention relates to synthetic receptors for ionophoric compounds, such as ionophoric toxins. Hence, the invention provides synthetic molecules capable of binding different ionophoric compounds, thereby being suitable for use in the detection, isolation and detoxification of such ionophoric compounds. The present invention further provides the use of such synthetic receptors in human and veterinary medicine, such as in the diagnosis, prevention and/or treatment of disorders caused by such ionophoric compounds. Finally, the invention provides methods of preparing such synthetic receptors for ionophoric compounds.

BACKGROUND TO THE INVENTION

The presence of toxins in food products such as grains provides a serious risk for toxicosis upon consumption of such food products.

For example beauvericin (BEA) and enniatins (ENN) are mycotoxins produced by fungi from the *Fusarium* genus which commonly infect grains such as wheat or maize. Due to their toxicity, in combination with a high prevalence in food, there is a need for detecting these analytes in food samples or in animal/human tissue for pharmacokinetic studies. Cereulide (CER) is an emetic toxin produced by *Bacillus cereus* which typically resides in rice or pasta causing food poisoning when consumed. Lethal cases of intoxication have been described.

It is known that (myco)toxin contamination in food is highly heterogeneous and therefore requires a large sampling size. Moreover due to the high prevalence of both CER and BEA/ENN in food, a method is needed which allows to analyse multiple samples in parallel and which can be used on the field. This has already been made possible for other mycotoxins such as aflatoxins, ochratoxin A, zearalenone, deoxynivalenol, . . . using testkits (such as ELISA, lateral flow devices, . . . ) but does not exist for BEA/ENN nor CER. Current methods for detecting BEA/ENN or CER rely on LC-MS and there is no fast, inexpensive assay available which allows the analysis of multiple samples simultaneously.

Specifically, beauvericin is a toxic cyclodepsipeptide produced by the insect pathogenic fungus *Beauveria bassiana* or by plant pathogenic *Fussarium* spp. The latter infects crops such as wheat and maize, which explains the high concentrations (up to 520 mg/kg) of beauvericin that can be found in infected kernels. This toxin is able to bind $K^+$ and $NH_{4+}$ cations via ion-dipole interactions and can transport these ions across lipid bilayers. By using membrane potential sensitive fluorescent dyes, Tonshin et al. showed that low µM concentrations of beauvericin are sufficient to cause depolarization of human neural (Paju) cells (Tonshin et al., 2010). Overnight incubation of human leukemia cells with 3 µM beauvericin, resulted in a drop of 80% survival rate, illustrating the toxic effect of this ionophore. Moreover, when mice were treated intraperitoneally with 5 mg beauvericin/kg bw for three consecutive days, bioaccumulation in the liver and lipophilic tissue was observed, probably due to the hydrophobic nature of this toxin. It is this combination of prevalence in food with toxic properties and tendency to bio-accumulate, that motivate the need to develop efficient and rapid detection systems for beauvericin. Current methods rely on LC-MS(/MS) (Santini et al., 2009) and even though this technique provides low limits of detection/quantification, some drawbacks are still persistent.

The main limitation resides in the fact that LC-MS(/MS) does not allow parallel measurements of many samples simultaneously, nor can it be used on site (in the field or in food processing facilities) where the fungi contamination and thus toxin production takes place. These limitations have been circumvented by the development of ELISA (O'Kennedy et al., 1990) and lateral flow devices (Maragos et al., 2009) which already exist commercially for the more well-known mycotoxins such as aflatoxins, deoxynivalenol and many others. Both methods however require antibodies to recognize the mycotoxin under investigation. These are typically generated via immunization of animals with the appropriate antigen. However, small molecules (so-called haptens in this context) are, in view of their low molecular weight, non-immunogenic. To circumvent this, the hapten is conjugated to a carrier protein and by doing so, an immune response and concomitant antibody production can be induced. (Gefen et al., 2014) While mycotoxins such as aflatoxins, zearalenone and deoxynivalenol contain functional groups that allow conjugation to such carrier-proteins, beauvericin does not. Given this difficulty to generate antibodies for beauvericin (due to the unavailability of appropriate functional groups for carrier-protein conjugation) and the fact that antibody binding efficiency is inherently dependent on factors such as ionic strength, pH and temperature which complicates their implementation in solid phase extraction and rapid tests, we envisioned to develop a synthetic receptor capable of selectively binding this toxin. A vast wealth of artificial receptors have already been developed for a broad range of ligands such as anions, cations, saccharides and small peptides to name a few. However, medium-sized depsipeptides such as beauvericin (FIG. 1) have remained unexplored as ligands for synthetic hosts.

Therefore it was an object of the present invention to provide a testkit for ionophoric toxins such as BEA/ENN and CER, which would allow their fast detection in a multi-sample setup. Our receptor design is based on the bridging of two steroid arms via a linker to create a hydrophobic cavity, in an effort to accommodate the lipophilic character of beauvericin. Secondly, incorporation of a primary amine functionality in the linker promotes binding due to the ionophoric nature of the toxin (FIG. 1). A carbazole moiety is used as linking fragment to ensure an adequate level of rigidity, while at the same time equipping the receptor with fluorescent properties.

These receptors are suitable for use in the isolation, detection and detoxification of ionophoric toxins, and thus provide a solution to the problems currently associated with early detection of toxin contamination in the food chain.

SUMMARY OF THE INVENTION

In a first aspect, the present invention provides a compound of formula (I):

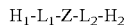   (I)

wherein:
H₁ and H₂ are hydrophobic moieties;
L₁ and L₂ are linker moieties;
Z is a moiety of formula (Ia)

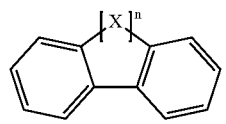   (Ia)

X is selected from the list comprising C, N and O;
n is 0 or 1;
wherein at least one of said $L_1$, $H_1$, $L_2$, $H_2$ and Z moieties is substituted with an amine-containing moiety; and
wherein said compound forms a cavity for accommodating an ionophoric compound.

In a specific embodiment of the present invention, each of said $H_1$ and $H_2$ hydrophobic moieties is independently a cyclic moiety comprising from 2 to 8 aromatic and/or non-aromatic 5-or 6-membered cycles; wherein each of said cycles may optionally comprise 1 or more heteroatoms, and/or may optionally be further substituted.

In another particular embodiment of the present invention, each of said $H_1$ and $H_2$ hydrophobic moieties is independently selected from the list comprising but not limited to: steroids, abietic acid derivatives, naphthalene, pyrene, acenaphthylene, and anthracene.

In yet a further embodiment of the present invention, each of said $L_1$ and $L_2$ linker moieties independently comprises one or more elements selected from the list comprising: alkyl, alkene, alkyn, phenyl, cycloalkane, heterocycle, cycloalkane, amide, ester, ether, carbamate, thiocarbamate; each of said elements being optionally substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles.

In a further embodiment of the present invention, said amine-containing moiety is attached to said $H_1$, $H_2$, $L_1$, $L_2$ or Z moiety through an alkyl linker; wherein said alkyl linker may be further substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles.

Hence, in particular embodiment, the present invention provides a compound of formula (I)

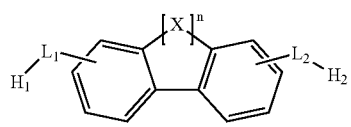   (I)

wherein:
L₁ and L₂ are each independently linker moieties comprising one or more elements selected from the list comprising: alkyl, alkene, alkyne, phenyl, heterocycle, cycloalkane, amide, ester, ether, carbamate, thiocarbamate; each of said elements being optionally substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles;
H₁ and H₂ are each independently hydrophobic cyclic moieties comprising from 2 to 8 aromatic and/or non-aromatic 5-or 6-membered cycles; wherein each of said cycles may optionally comprise 1 or more heteroatoms, and/or may optionally be further substituted;
X is selected from the list comprising —CR'R"—, —NR'— and —O—;
R' and R" are each independently selected from the list comprising —H and optionally substituted alkyl;
n is 0 or 1;
wherein at least one of said $L_1$, $H_1$, $L_2$, $H_2$ and

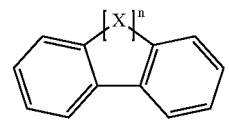

moieties is substituted with an amine-containing moiety; and
wherein said compound forms a cavity for accommodating an ionophoric compound.

In a still further embodiment, the present invention provides a compound as defined herein and being of formula (II)

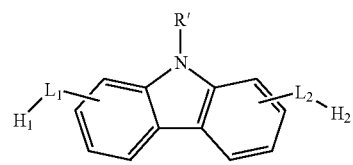   (II)

wherein:
L₁ and L₂ are each independently linker moieties comprising one or more elements selected from the list comprising: alkyl, alkene, alkyne, phenyl, heterocycle, cycloalkane, amide, ester, ether;
H₁ and H₂ are each independently hydrophobic cyclic moieties comprising from 2 to 8 aromatic and/or non-aromatic 5-or 6-membered cycles; wherein each of said cycles may optionally comprise 1 or more heteroatoms, and/or may optionally be further substituted;

R' is optionally substituted alkyl;

wherein at least one of said $L_1$, $H_1$, $L_2$, $H_2$ and R' moieties is substituted with an amine-containing moiety; and wherein said compound forms a cavity for accommodating an ionophoric compound.

In yet a further embodiment, the present invention provides a compound as defined herein and being of formula (III)

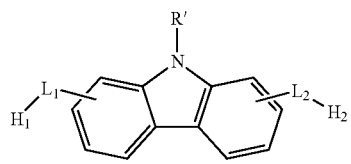

wherein:

$L_1$ and $L_2$ are each independently linker moieties comprising one or more elements selected from the list comprising: alkyl, alkene, alkyne, phenyl, heterocycle, cycloalkane, amide, ester, ether;

$H_1$ and $H_2$ are each independently hydrophobic cyclic moieties comprising from 2 to 8 aromatic and/or non-aromatic 5-or 6-membered cycles; wherein each of said cycles may optionally comprise 1 or more heteroatoms, and/or may optionally be further substituted;

R' is optionally substituted alkyl;

wherein at least one of said $L_1$, $H_1$, $L_2$, $H_2$ and R' moieties is substituted with an amine-containing moiety; and wherein said compound forms a cavity for accommodating an ionophoric compound.

In a particular embodiment of the present invention, said amine-containing moiety may be selected from the list comprising: —$NH_3^+$ and —NHY; wherein Y is a protecting group, such as selected from the list comprising: Boc, Fmoc, Cbz, Bn and Trt.

In a particular embodiment of the present invention, each of said $H_1$ and $H_2$ hydrophobic moieties is independently selected from the list comprising: steroids, abietic acid derivatives, naphthalene, pyrene, acenaphthylene, and anthracene.

In yet another particular embodiment of the present invention, said amine-containing moiety is attached to said $H_1$, $H_2$, $L_1$, $L_2$, R' or

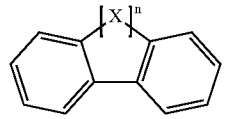

moiety through an alkyl linker;

wherein said alkyl linker may be further substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles.

The present invention further provides a compound of Formula (IIIa) or a stereoisomer, tautomer, racemic, metabolite, pro- or predrug, salt, hydrate, or solvate thereof:

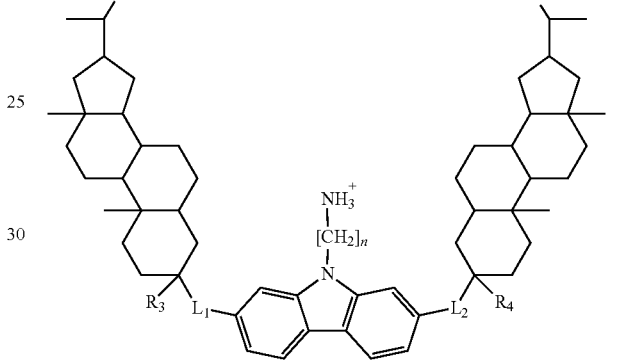

wherein:

$R_1$ and $R_2$ are each independently selected from the list comprising: —(C=O)—O—$C_{1-6}$alkyl, —(C=O)—NH—$C_{1-6}$alkyl and —(C=O)—OH; wherein each of said —$C_{1-6}$alkyl is optionally substituted with one or more of —OH, -halo, -biotin, -disulfide, or a detectable label;

$R_3$ and $R_4$ are each independently selected from the list comprising: —H and —OH;

$L_1$ and $L_2$ are each independently selected from the list comprising:

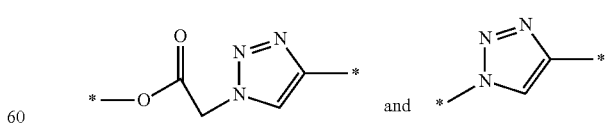

wherein each of said moieties can be present in the compounds in either direction; m, n and p are each independently an integer from 1 to 10.

In a very specific embodiment of the present invention, said compound is selected from the list comprising:
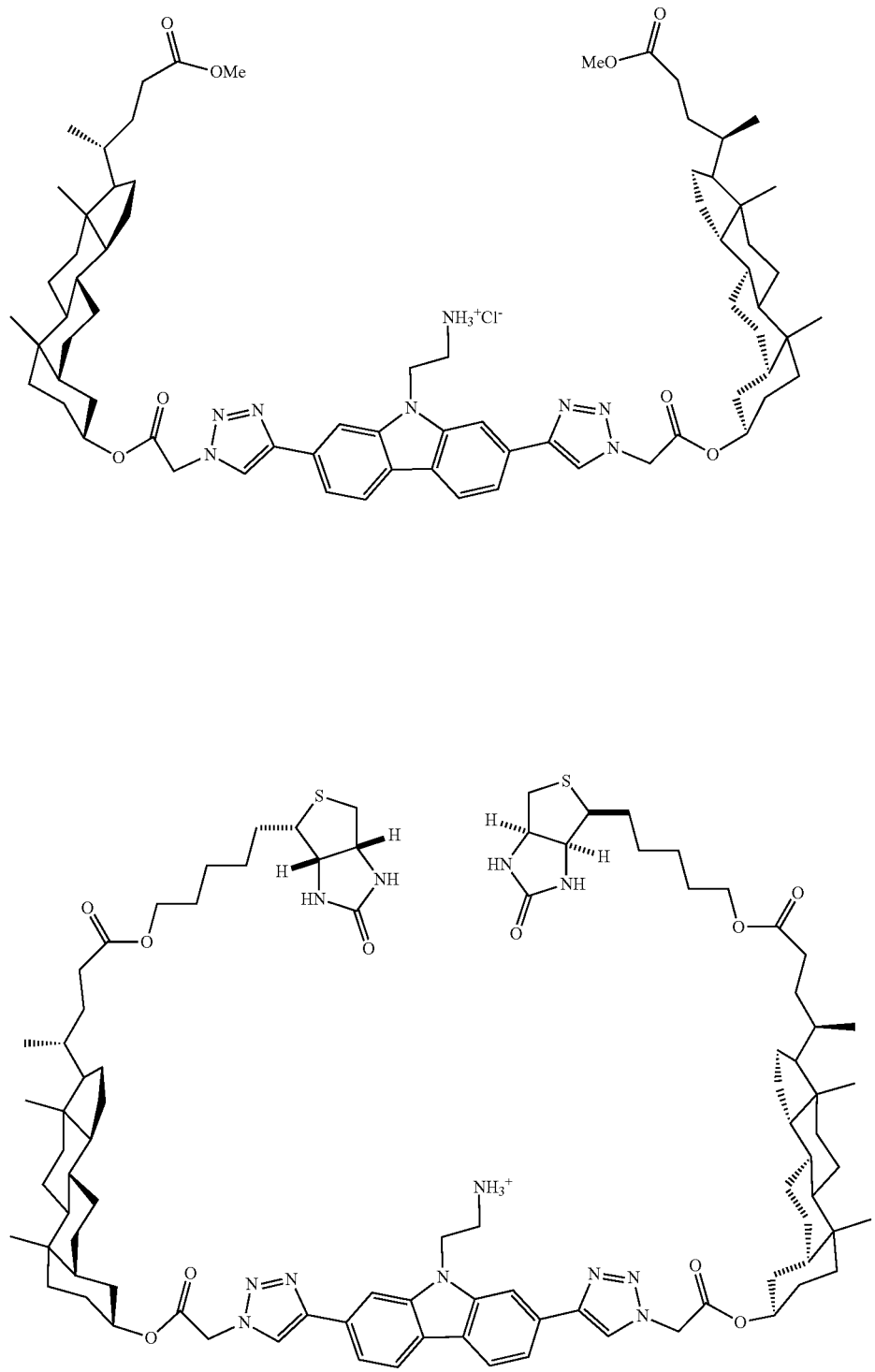

-continued
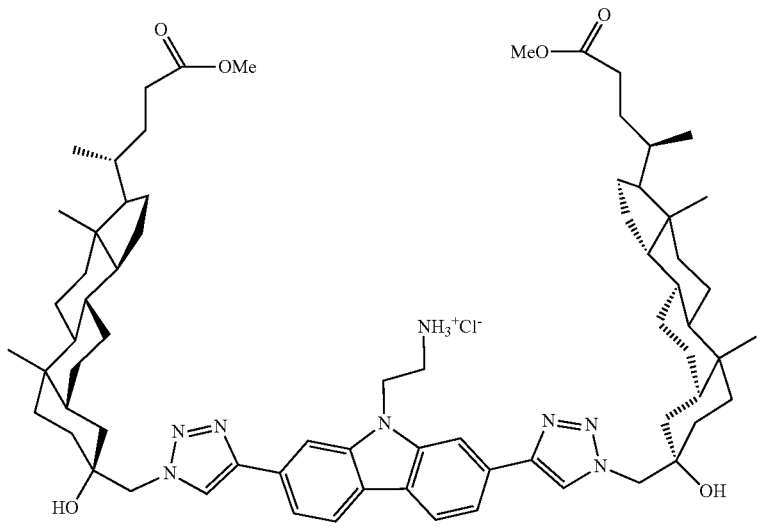
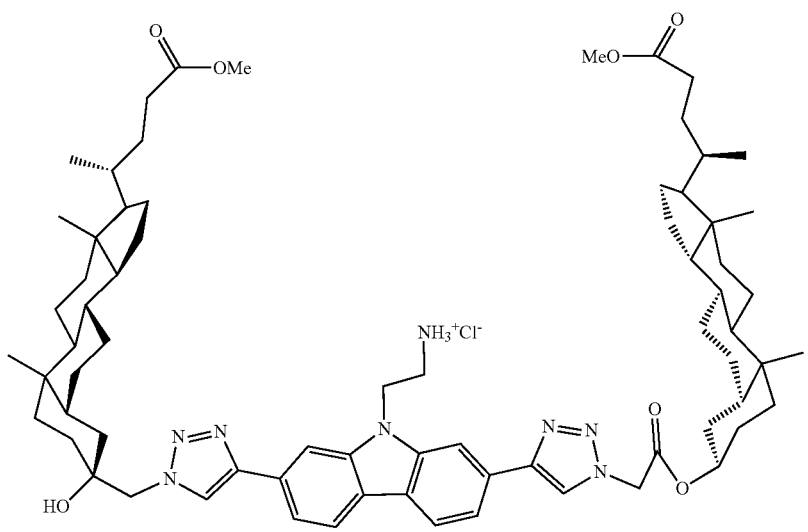
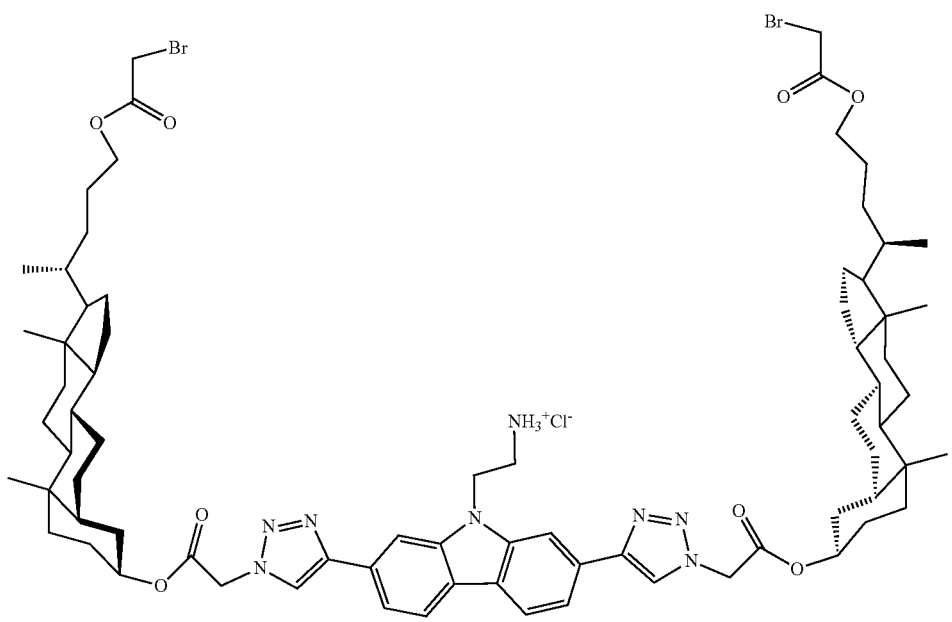

-continued

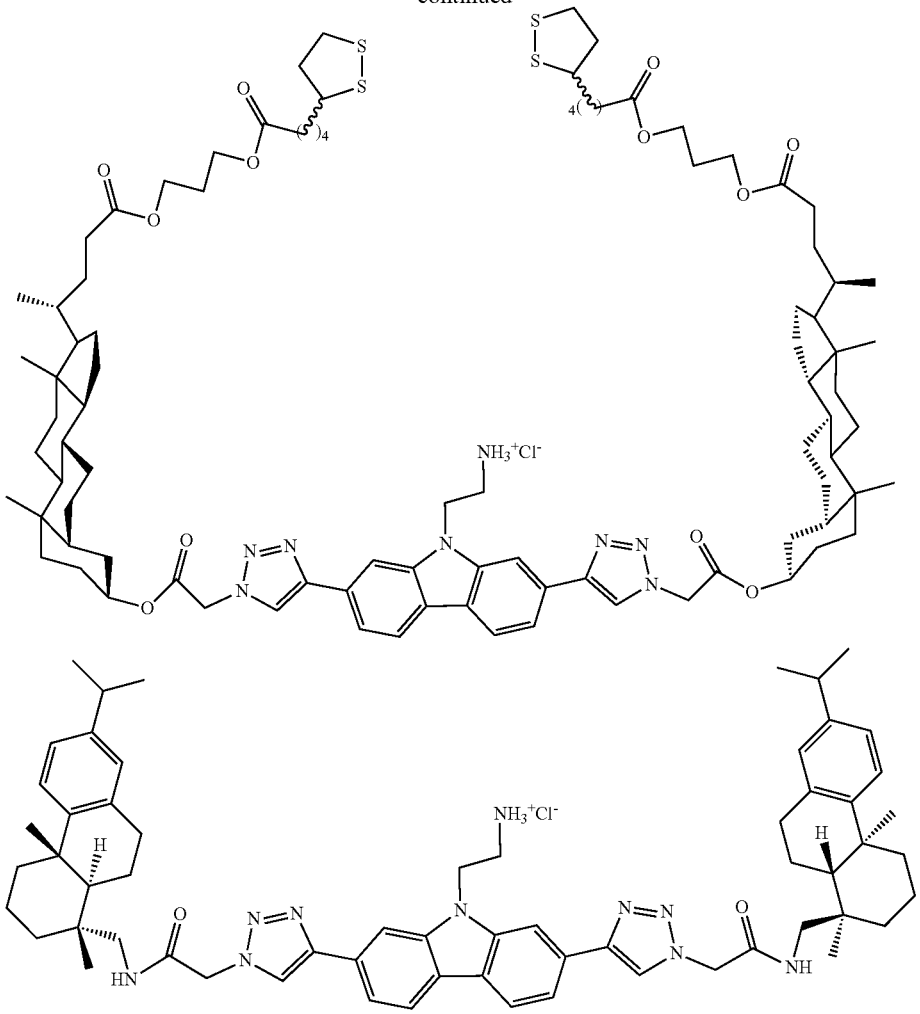

The present invention also provides a pharmaceutical composition comprising a compound as defined herein and a pharmaceutically acceptable excipient of carrier; more specifically, for use in human and/or veterinary medicine.

The present invention further provides the compound or the composition as defined herein for use in the diagnosis, prevention and/or treatment of disorders caused by ionophoric compounds, such as selected from the list comprising neurological disorders, cancer, food poisoning, heart disorders, and encephalopathy. Said ionophoric compounds may for example be mycotoxins beauvericin or enniatins; ionophoric polyether antibiotics, such as monensin A and salinomycin; emetic toxins such as cereulide; or the bacterial ionophore valinomycin.

The present invention further provides a method for the prevention and/or treatment of at least one disease or disorder being caused by an ionophoric compound; said method comprising administering to a subject in need thereof a therapeutically effective amount of a compound or a pharmaceutical composition as defined herein.

In yet a further aspect, the present invention provides a solid support having attached thereto a compound of the present invention.

Finally, the present invention provides the use of a compound or a solid support of the present invention in solid phase extraction of ionophoric compounds, in purification of ionophoric compounds using liquid chromatography, in decontamination of food products containing these compounds or for the detection, isolation and/or detoxification of an ionophoric compound.

BRIEF DESCRIPTION OF THE DRAWINGS

With specific reference now to the figures, it is stressed that the particulars shown are by way of example and for purposes of illustrative discussion of the different embodiments of the present invention only. They are presented for the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
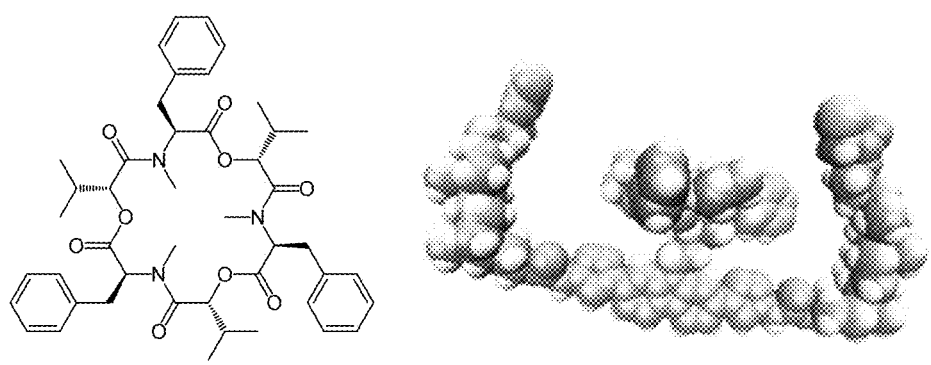
FIG. 1. Chemical structure of beauvericin and visual spatial representation of beauvericin (central) and the synthetic receptor (surrounding) using VMD software.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

As already mentioned hereinbefore, in a first aspect the present invention provides compounds of Formula I, $$H_1\text{-}L_1\text{-}Z\text{-}L_2\text{-}H_2 \quad (I)$$

wherein:

$H_1$ and $H_2$ are hydrophobic moieties;

$L_1$ and $L_2$ are linker moieties;

Z is a moiety of formula (Ia)

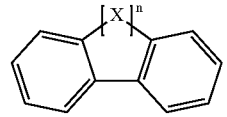

(Ia)

X is selected from the list comprising C, N and O;

n is 0 or 1;

wherein at least one of said $L_1$, $H_1$, $L_2$, $H_2$ and Z moieties is substituted with an amine-containing moiety; and wherein said compound forms a cavity for accommodating an ionophoric compound.

In particular, the present invention provides a compound of formula (I)

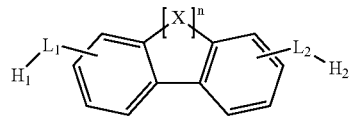

(I)

wherein:

$L_1$ and $L_2$ are each independently linker moieties comprising one or more elements selected from the list comprising: alkyl, alkene, alkyne, phenyl, heterocycle, cycloalkane, amide, ester, ether, carbamate, thiocarbamate; each of said elements being optionally substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles;

$H_1$ and $H_2$ are each independently hydrophobic cyclic moieties comprising from 2 to 8 aromatic and/or non-aromatic 5-or 6-membered cycles; wherein each of said cycles may optionally comprise 1 or more heteroatoms, and/or may optionally be further substituted;

X is selected from the list comprising —CR'R"—, —NR'— and —O—;

R' and R" are each independently selected from the list comprising —H and optionally substituted alkyl;

n is 0 or 1;

wherein at least one of said $L_1$, $H_1$, $L_2$, $H_2$ and

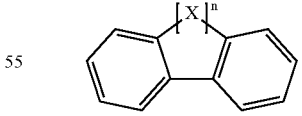

moieties is substituted with an amine-containing moiety; and wherein said compound forms a cavity for accommodating an ionophoric compound.

In a particular embodiment, the optional substituents on the $H_1$ and/or $H_2$ moieties may be selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles.

In another particular embodiment, the optional substituents on the $H_1$ and/or $H_2$ moieties may be selected from the list comprising: alkoxycarbonyl, PEG, polyoxazoline, cyclic disulfides, biotin, sulphate, halogen, N-hydroxy-succinimide and maleimide.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include halo, hydroxyl, carbonyl, nitro, amino, oxime, imino, azido, hydrazino, cyano, aryl, heteroaryl, cycloalkyl, acyl, alkylamino, alkoxy, thiol, alkylthio, carboxylic acid, acylamino, alkyl esters, carbamate, thioamido, urea, sulfonamido and the like.

The term "alkenyl", as used herein, unless otherwise indicated, means straight-chain or branched-chain hydrocarbon moieties containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E, Z-hexenyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, E- and Z-propynyl, isopropynyl, E- and Z-butynyl, E- and Z-isobutynyl, E- and Z-pentynyl, E, Z-hexynyl, and the like. An optionally substituted alkynyl refers to an alkynyl having optionally one or more substituents (for example 1, 2, 3 or 4), selected from those defined above for substituted alkyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkynyl groups as defined above, are divalent radicals having single bonds for attachment to two other groups, they are termed "alkynylene".

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2CH_2CH_2$—*, *—CH(—$CH_2$CH3)—*, or *—$CH_2$CH(—$CH_3$)—*.

The term "cycloalkyl" or "cycloalkane" by itself or as part of another substituent is a cyclic alkyl group, that is to say, a monovalent, saturated, or unsaturated hydrocarbyl group having a cyclic structure. Cycloalkyl includes all saturated or partially saturated (containing 1 or 2 double bonds) hydrocarbon groups having a cyclic structure. Cycloalkyl groups may comprise 3 or more carbon atoms in the ring and generally, according to this invention comprise from 3 to 6 atoms. Examples of cycloalkyl groups include but are not limited to cyclopropyl, cyclobutyl, cyclopentyl, cyclohexyl.

The term "carboxy" or "carboxyl" or "hydroxycarbonyl" by itself or as part of another substituent refers to the group —$CO_2$H. Thus, a carboxyalkyl is an alkyl group as defined above having at least one substituent that is —$CO_2$H.

The term "alkoxycarbonyl" by itself or as part of another substituent refers to a carboxy group linked to an alkyl radical i.e. to form —C(=O)O$R^e$, wherein $R^e$ is as defined above for alkyl. The term "halo" or "halogen" as a group or part of a group is generic for fluoro, chloro, bromo, or iodo.

The term -disulfide is meant to be a —SSR' moiety, said disulfide may also be in the form of a 5- or 6-membered cyclic moiety wherein R' may be —H.

The term "amide" refers to a functional group represented by $R_nE(O)_xNR'_2$ (R and R' refer to H or organic groups). Most common are carboxamides (organic amides) (n=1, E=C, x=1), but many other important types of amides are known, including phosphoramides (n=2, E=P, x=1 and many related formulas) and sulfonamides (E=S, x=2).

The term "ester" refers to a moiety derived from an acid (organic or inorganic) in which at least one —OH (hydroxyl) group is replaced by an —O-alkyl (alkoxy) group. Typically, esters are derived from a carboxylic acid and an alcohol.

The term "ether" refers to a moiety in which an oxygen atom is connected to two alkyl or aryl groups. They have the general formula R—O—R', where R and R' independently from each other represent the alkyl or aryl groups.

The term "carbamate" refers to a moiety derived from carbamic acid ($NH_2$COOH). A carbamate group, carbamate ester (e.g., ethyl carbamate), and carbamic acids are functional groups that are inter-related structurally and often are interconverted chemically. Carbamate esters are also called urethanes.

Thiocarbamates are sulphur analogues of carbamates. There are two isomeric forms of thiocarbamate esters: O-thiocarbamates, ROC(=S)$NR_2$, and S-thiocarbamates, RSC(=O)$NR_2$.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

The term "heterocycle" as used herein by itself or as part of another group refers to non-aromatic, fully saturated or partially unsaturated cyclic groups (for example, 3 to 6 membered monocyclic ring systems) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl. Exemplary heterocyclic groups include triazolinyl, piperidinyl, azetidinyl, imidazolinyl, imidazolidinyl, isoxazolinyl, oxazolidinyl, isoxazol id inyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3- pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3- dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl; in particular pyrrolidinyl, imidazolidinyl, pyrazolidinyl, piperidinyl, dioxolanyl, dioxanyl, morpholinyl, thiomorpholinyl, piperazinyl, thiazolidinyl, tetrahydropyranyl, and tetrahydrofuranyl.

As described herein, some of the compounds of the invention may contain one or more asymmetric carbon atoms that serve as a stereogenic center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I, II, III and any subgroup thereof. This term also refers to the compounds as depicted herein, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In the context of the present invention, the term hydrophobic moiety is meant to be a moiety that is not attracted to water, but instead repelled from water. Due to the hydrophobic nature of these moieties, the compounds of the present invention tend to form a cavity which is suitable for accommodating ionophoric compounds, such as ionophoric toxins.

In a specific embodiment of the present invention, each of said $H_1$ and $H_2$ hydrophobic moieties is independently a cyclic moiety comprising from 2 to 8 aromatic and/or non-aromatic 5-or 6-membered cycles; wherein each of said cycles may optionally comprise 1 or more heteroatoms, and/or may optionally be further substituted.

In another particular embodiment of the present invention, each of said $H_1$ and $H_2$ hydrophobic moieties is independently selected from the list comprising: steroids, abietic acid derivatives, naphthalene, pyrene, acenaphthylene, and anthracene.

In yet a further embodiment of the present invention, each of said $L_1$ and $L_2$ linker moieties independently comprises one or more elements selected from the list comprising: alkyl, alkene, alkyn, phenyl, cycloalkane, heterocycle, cycloalkane, amide, ester, ether, carbamate, thiocarbamate; each of said elements being optionally substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles.

In a further embodiment of the present invention, said amine-containing moiety is attached to said $H_1$, $H_2$, $L_1$, $L_2$, R' or Z moiety through an alkyl linker; wherein said alkyl linker may be further substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles.

In a specific embodiment, the present invention provides a compound as defined herein and being of formula (II)

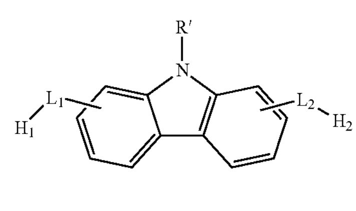

(II)

wherein:

$L_1$ and $L_2$ are each independently linker moieties comprising one or more elements selected from the list comprising: alkyl, alkene, alkyne, phenyl, heterocycle, cycloalkane, amide, ester, ether;

$H_1$ and $H_2$ are each independently hydrophobic cyclic moieties comprising from 2 to 8 aromatic and/or non-aromatic 5-or 6-membered cycles; wherein each of said cycles may optionally comprise 1 or more heteroatoms, and/or may optionally be further substituted;

R' is optionally substituted alkyl;

wherein at least one of said $L_1$, $H_1$, $L_2$, $H_2$ and R' moieties is substituted with an amine-containing moiety; and wherein said compound forms a cavity for accommodating an ionophoric compound.

In an even further specific embodiment, the present invention provides a compound as defined herein and being of formula (III)

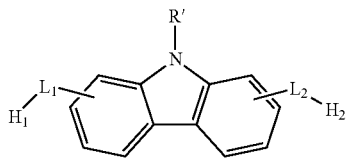

(III)

wherein:
L$_1$ and L$_2$ are each independently linker moieties comprising one or more elements selected from the list comprising: alkyl, alkene, alkyne, phenyl, heterocycle, cycloalkane, amide, ester, ether;
H$_1$ and H$_2$ are each independently hydrophobic cyclic moieties comprising from 2 to 8 aromatic and/or non-aromatic 5-or 6-membered cycles; wherein each of said cycles may optionally comprise 1 or more heteroatoms, and/or may optionally be further substituted;
R' is optionally substituted alkyl;
wherein at least one of said L$_1$, H$_1$, L$_2$, H$_2$ and R' moieties is substituted with an amine-containing moiety; and
wherein said compound forms a cavity for accommodating an ionophoric compound.

In a particular embodiment of the compounds of the invention, said amine-containing moiety is selected from the list comprising: —NH$_3^+$ and —NHY; wherein Y is a protecting group, such as selected from the list comprising: Boc, Fmoc, Cbz, Bn and Trt.

In another particular embodiment of the compounds of the invention, each of said H$_1$ and H$_2$ hydrophobic moieties is independently selected from the list comprising: steroids, abietic acid derivatives, naphthalene, pyrene, acenaphthylene, and anthracene.

In yet a further embodiment of the compounds of the invention, said amine-containing moiety is attached to said H$_1$, H$_2$, L$_1$, L$_2$, R' or

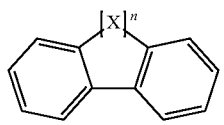

moiety through an alkyl linker;
wherein said alkyl linker may be further substituted with one or more substituents selected from the list comprising: hydroxyl groups, carboxyl groups, carbonyl groups, thiol groups, sulphide groups, sulfonyl groups, amides, amines, epoxides, aldehydes, cyano groups, nitrile groups, aminocarbonyl groups, aminocarboxyl groups, alkene, alkyne, phenyl, and heterocycles.

Specific examples of the Z moiety and more in particular the

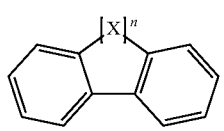

moiety of the present invention include but are not limited to:

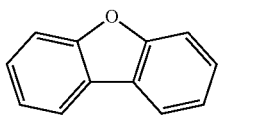

dibenzofuran
x = O
n = 1

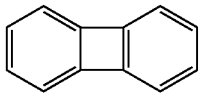

biphenylene
n = 0

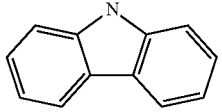

carbazole
x = N
n = 1

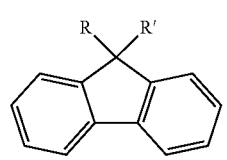

fluorene
x = C
n = 1 with R=H, alkyl, . . . .

In a further specific embodiment, the L$_1$ and L$_2$ moieties may be attached to the

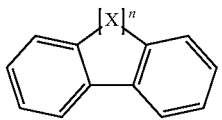

moiety according to

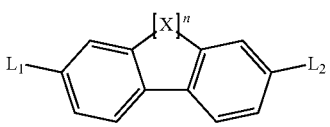

A

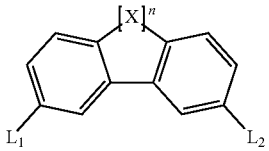

B any of the following representations:

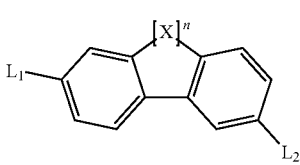

C

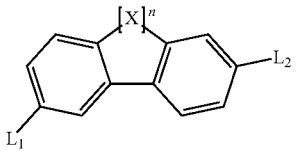

D

In a very specific embodiment, the $L_1$ and $L_2$ moieties of the present invention may be selected from the non-limiting list comprising:

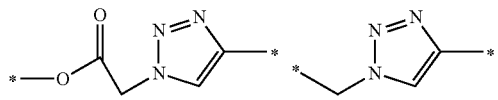

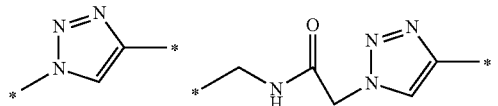

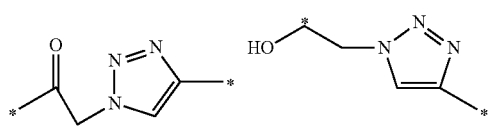

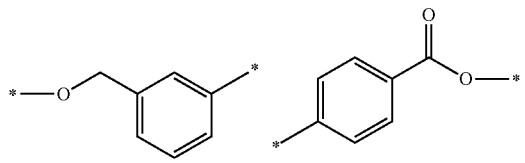

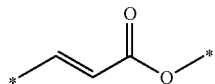

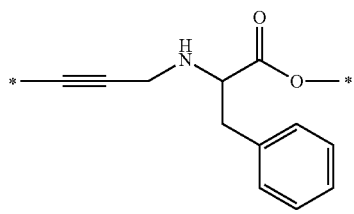

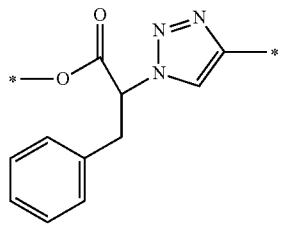

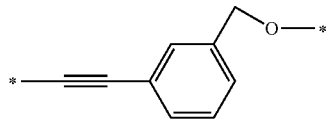

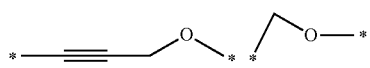

-continued

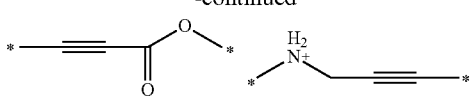

In each of the above representations, $L_1$ and $L_2$ may be present in either direction.

The present invention further provides a compound of Formula (IIIa) or a stereoisomer, tautomer, racemic, metabolite, pro- or predrug, salt, hydrate, or solvate thereof:

(IIIa)

[structure of Formula (IIIa)]

wherein:

$R_1$ and $R_2$ are each independently selected from the list comprising: —(C=O)—O—$C_{1-6}$alkyl, —(C=O)—NH—$C_{1-6}$alkyl and —(C=O)—OH; wherein each of said —$C_{1-6}$alkyl is optionally substituted with one or more of —OH, -halo, -biotin, -disulfide, or a detectable label;

$R_3$ and $R_4$ are each independently selected from the list comprising: —H and —OH;

$L_1$ and $L_2$ are each independently selected from the list comprising:

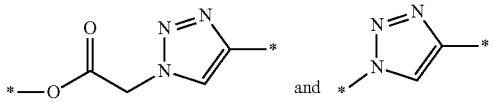 [SMILES: *OC(=O)Cn1cc(*)nn1 ; *c1cn(*)nn1]

wherein each of said moieties can be present in the compounds in either direction; m, n and p are each independently an integer from 1 to 10.

In a further embodiment of the present invention, the compound is selected from the list comprising:
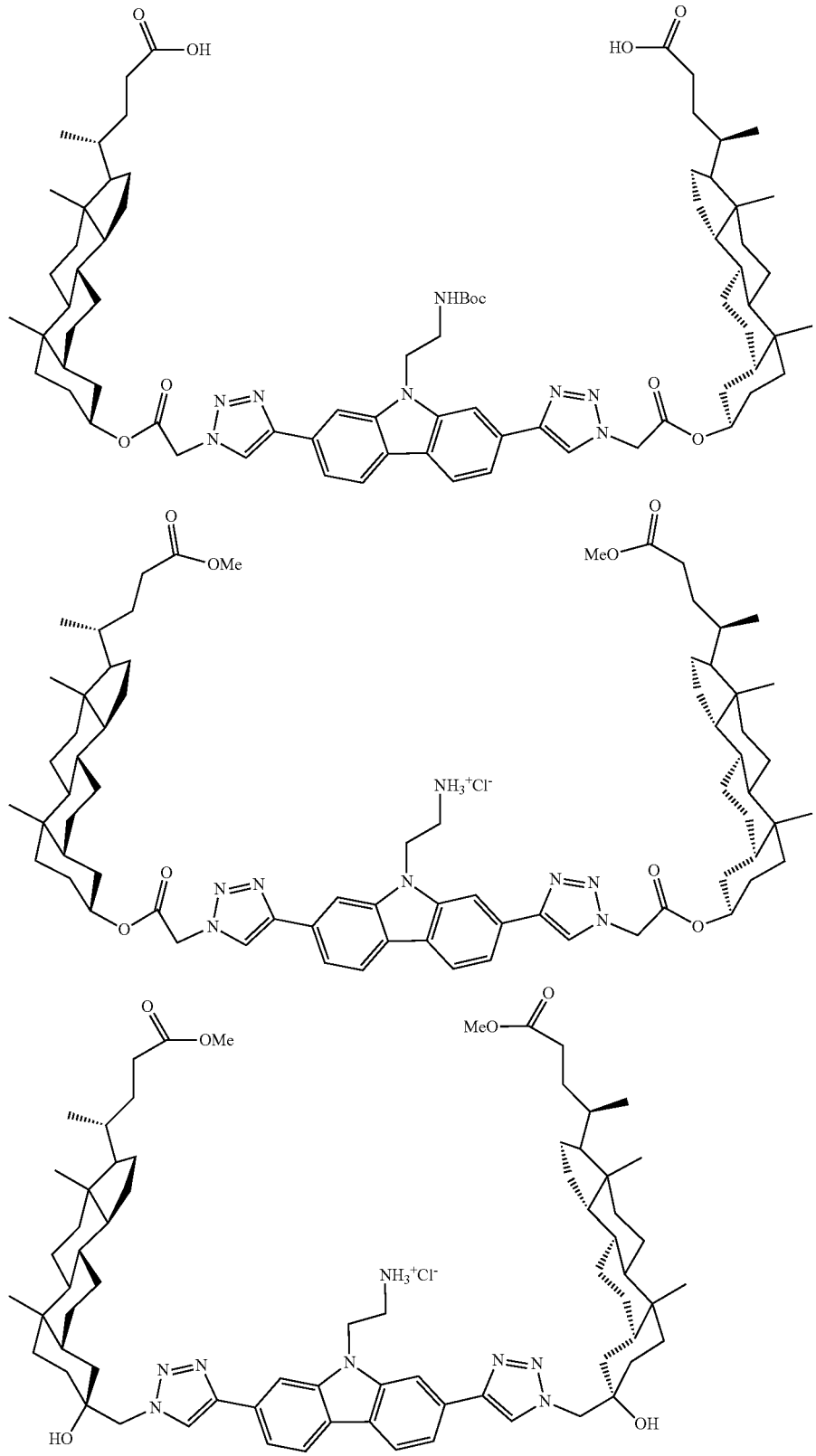

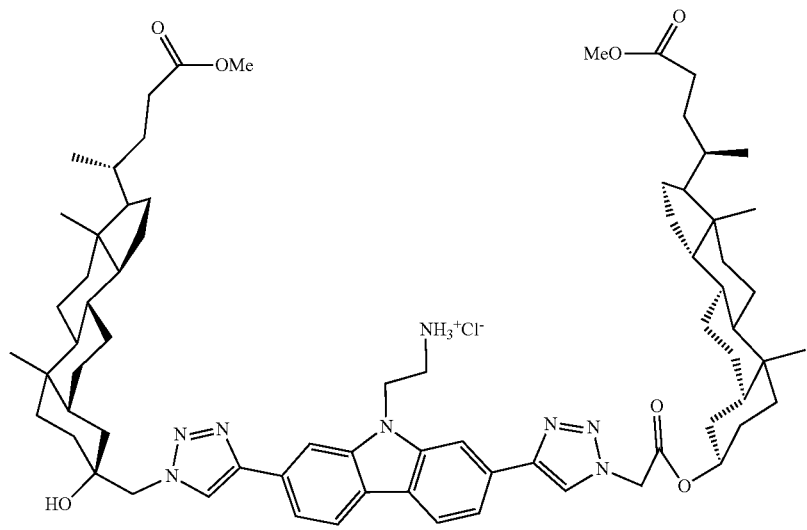
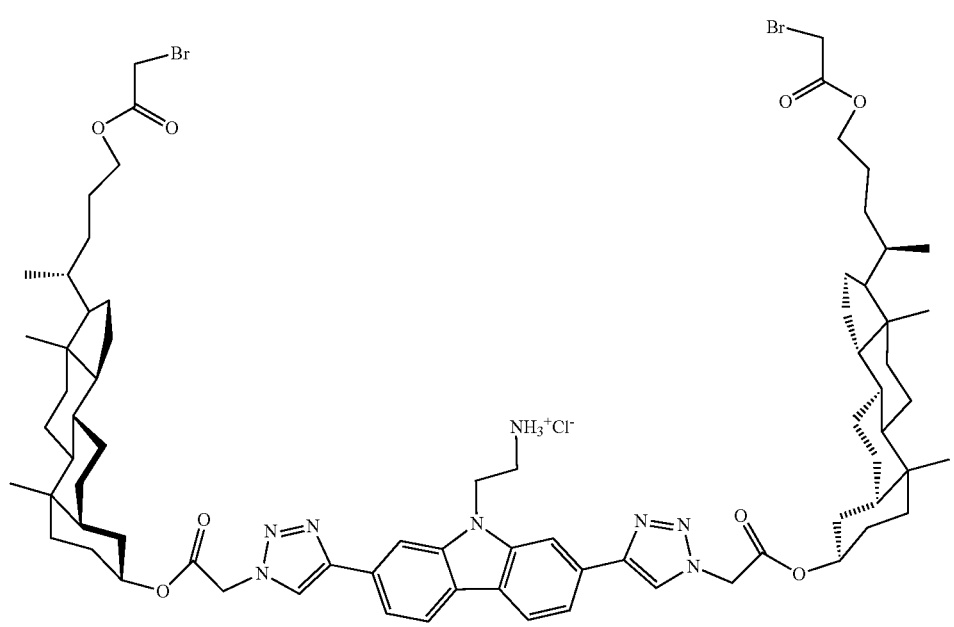

-continued
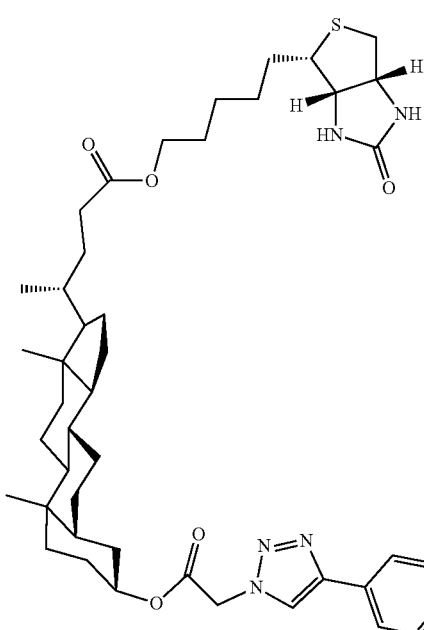
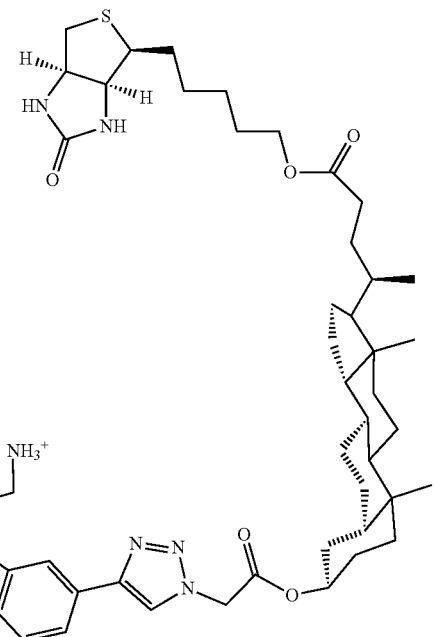
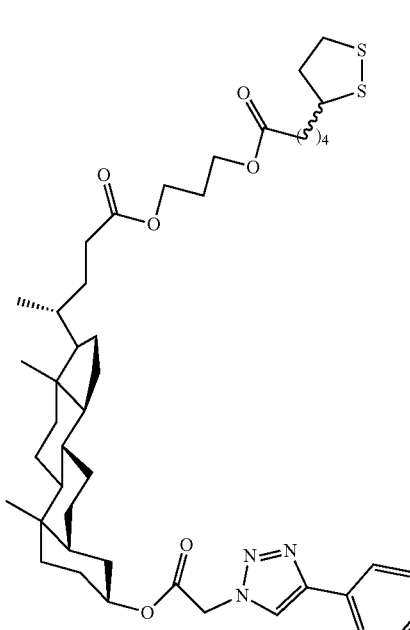
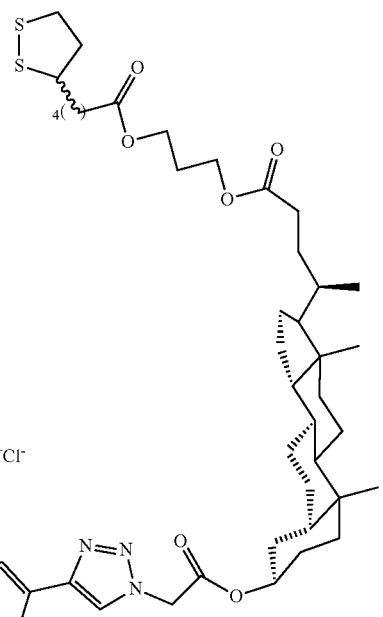
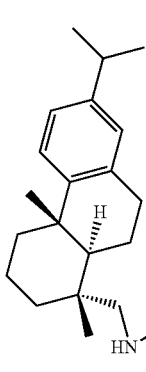
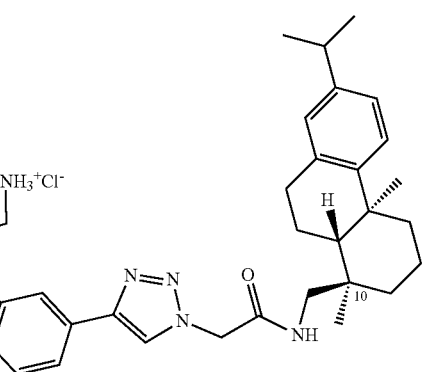

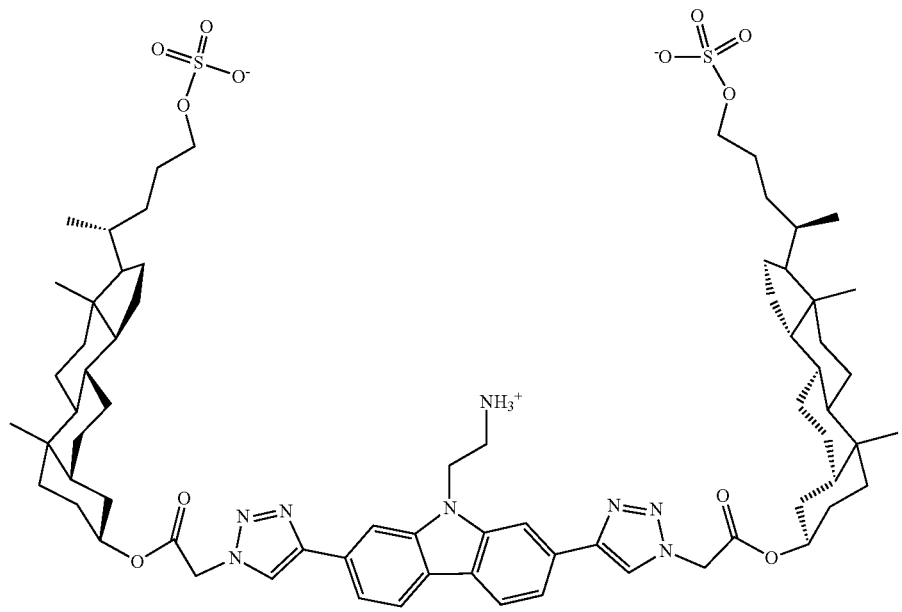
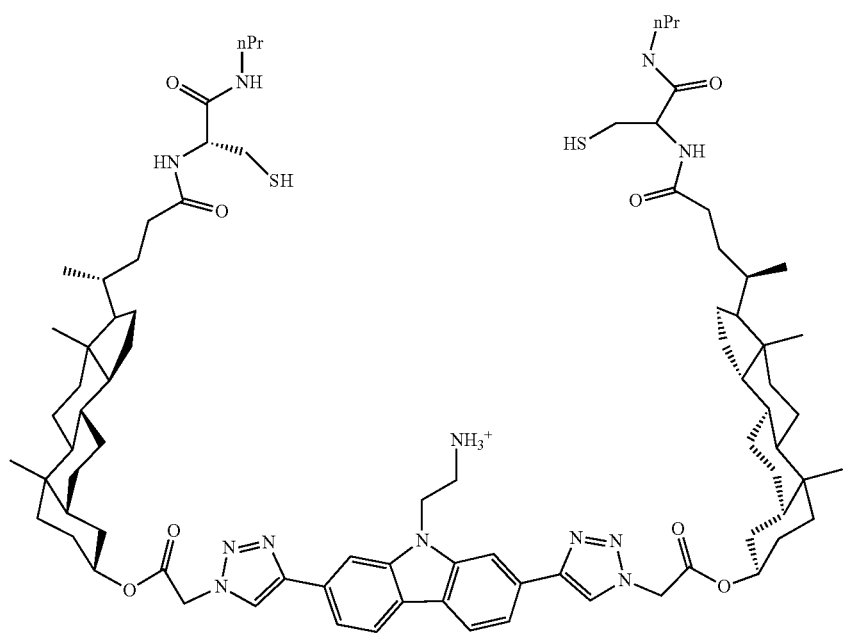

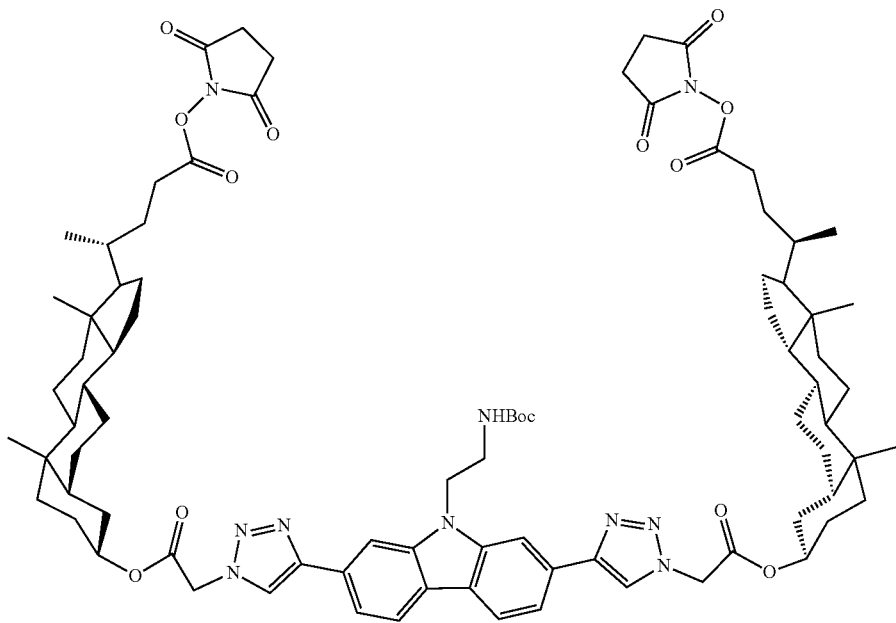
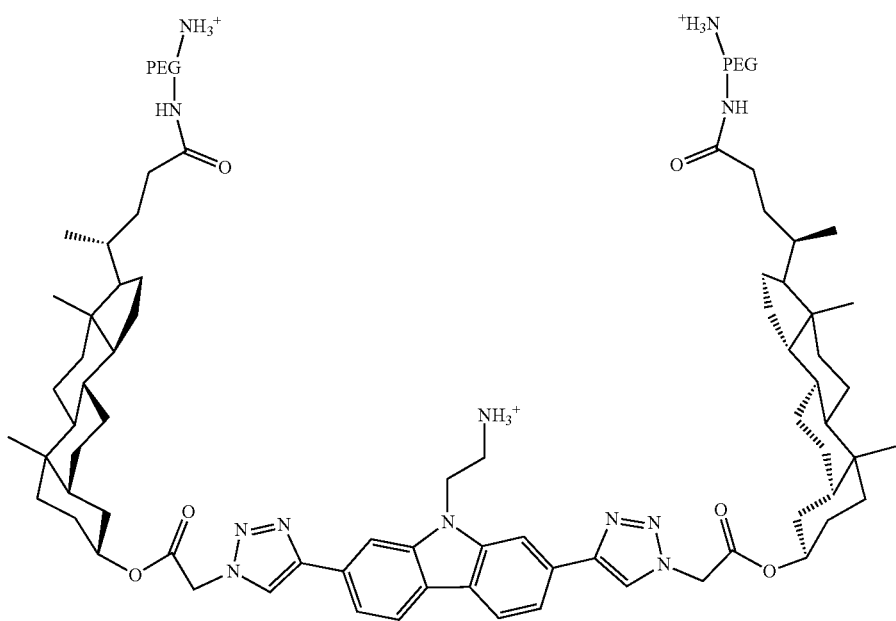

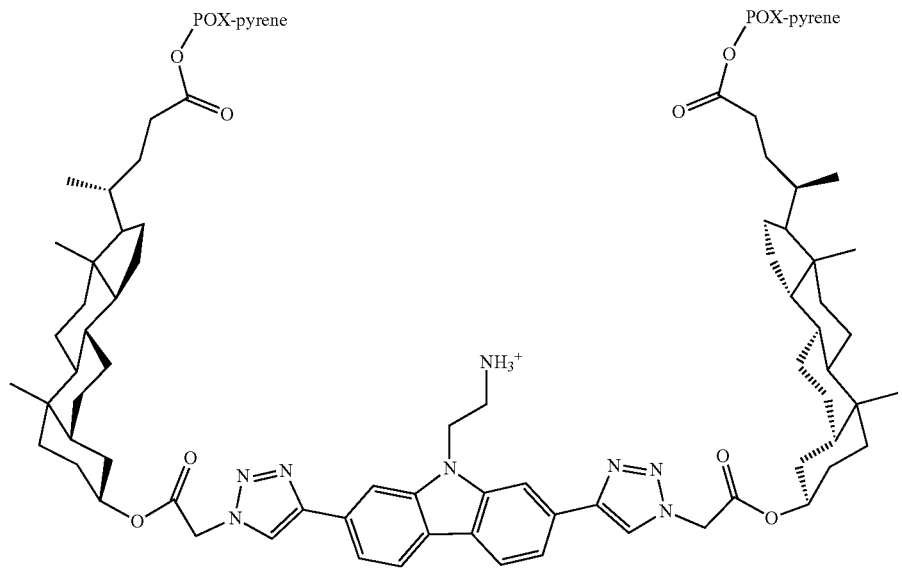
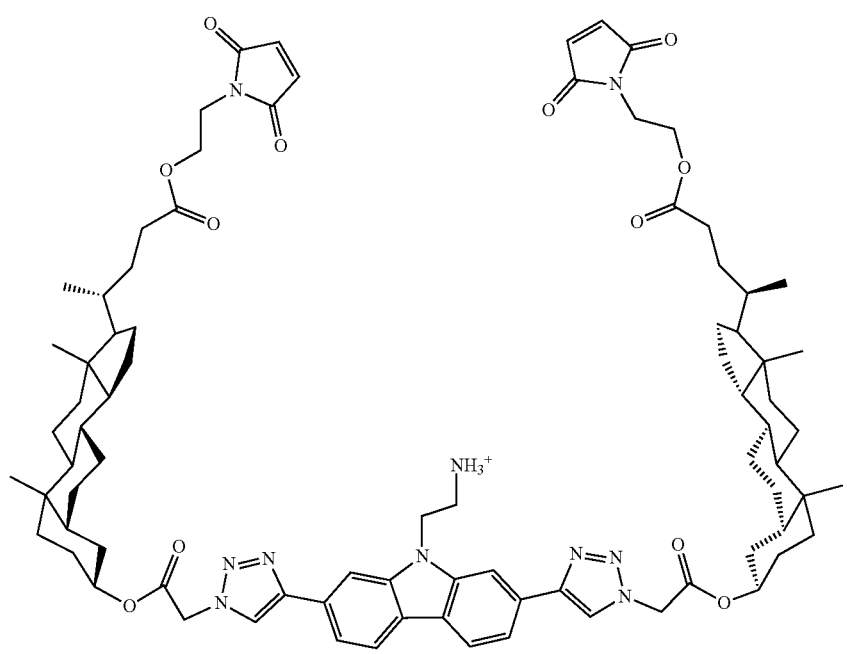

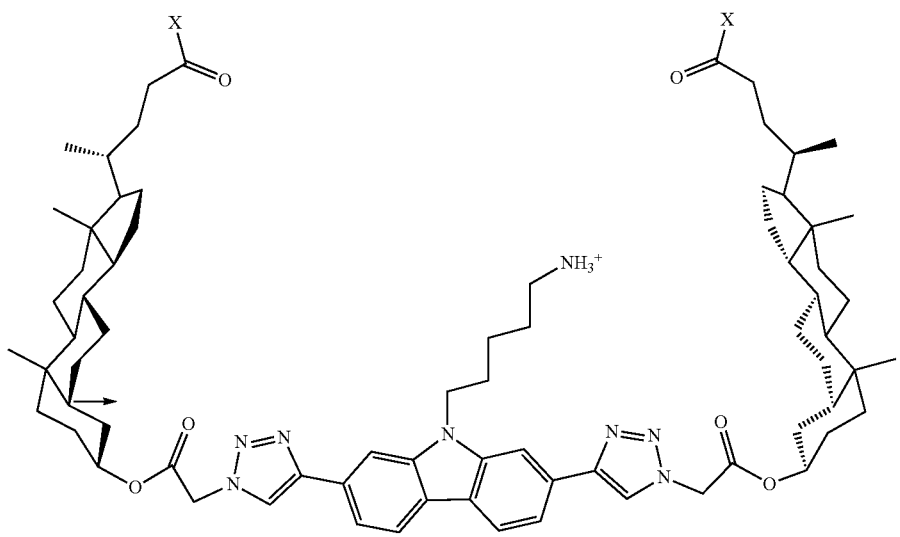
X20
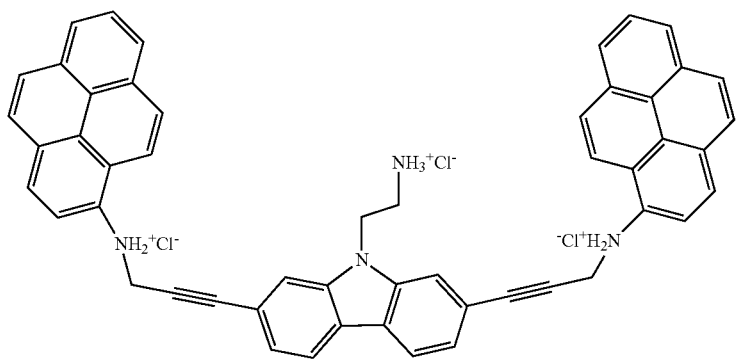
X5
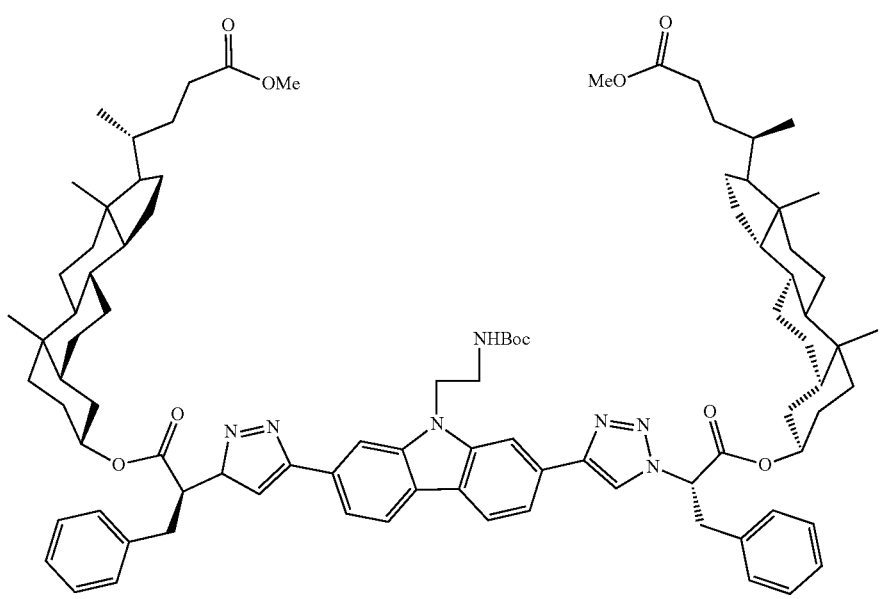

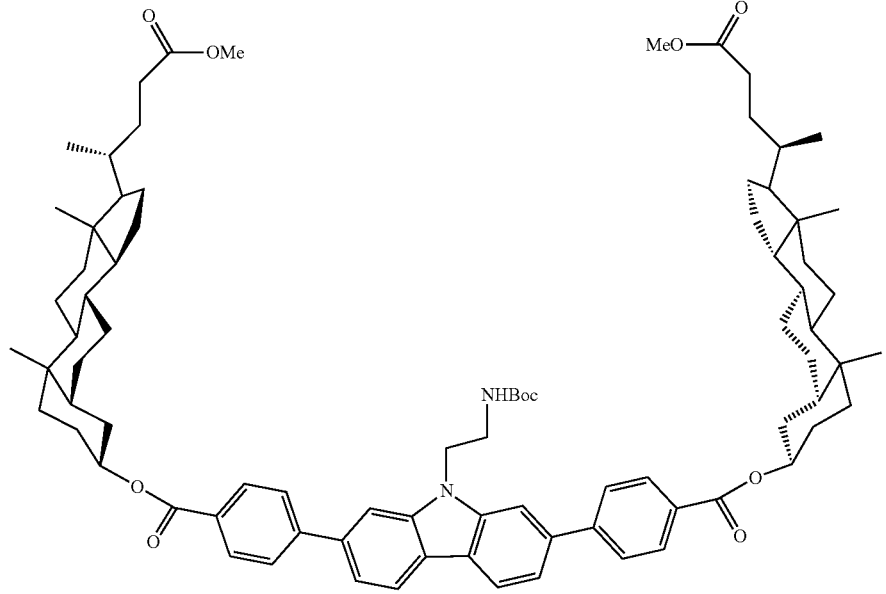
X7
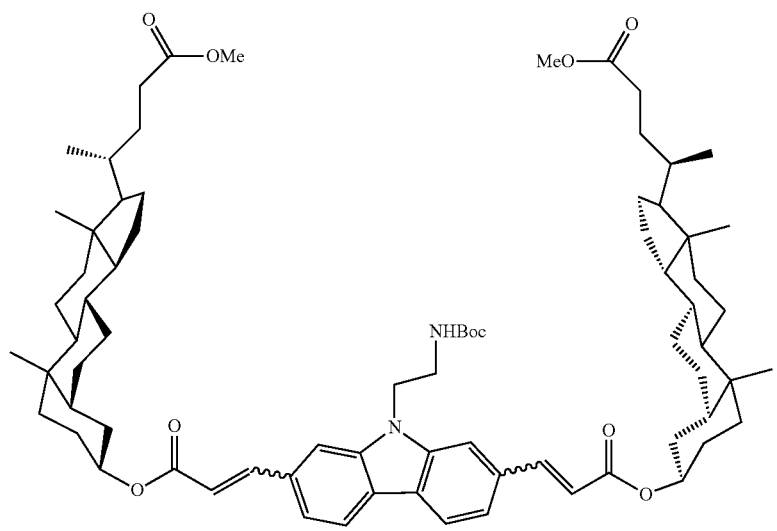
X10

-continued
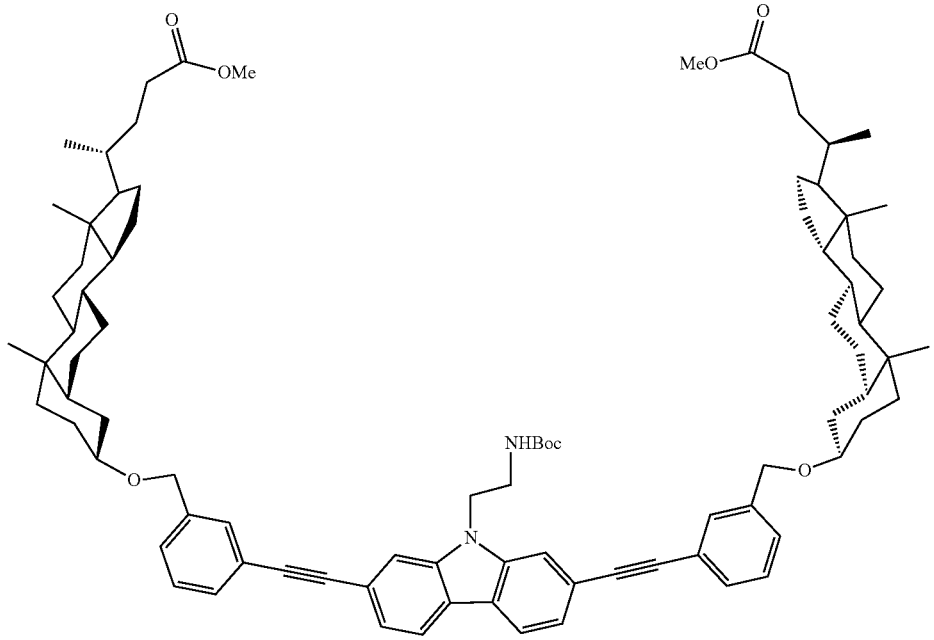
X12
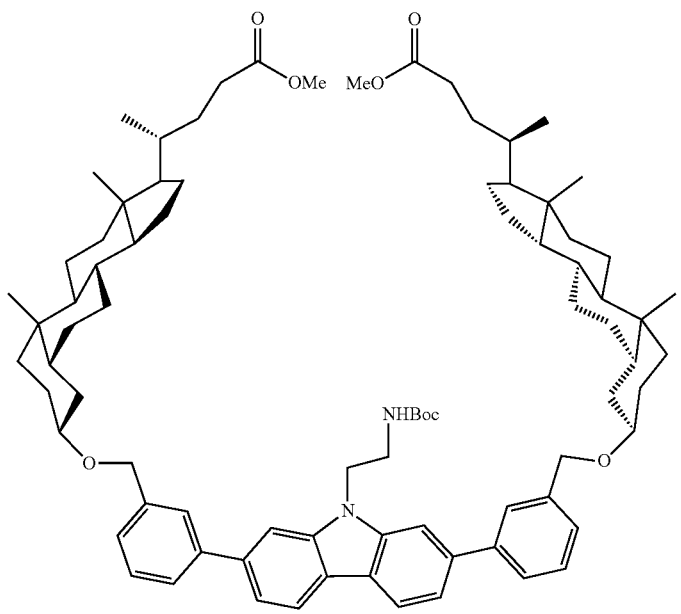
X14

-continued
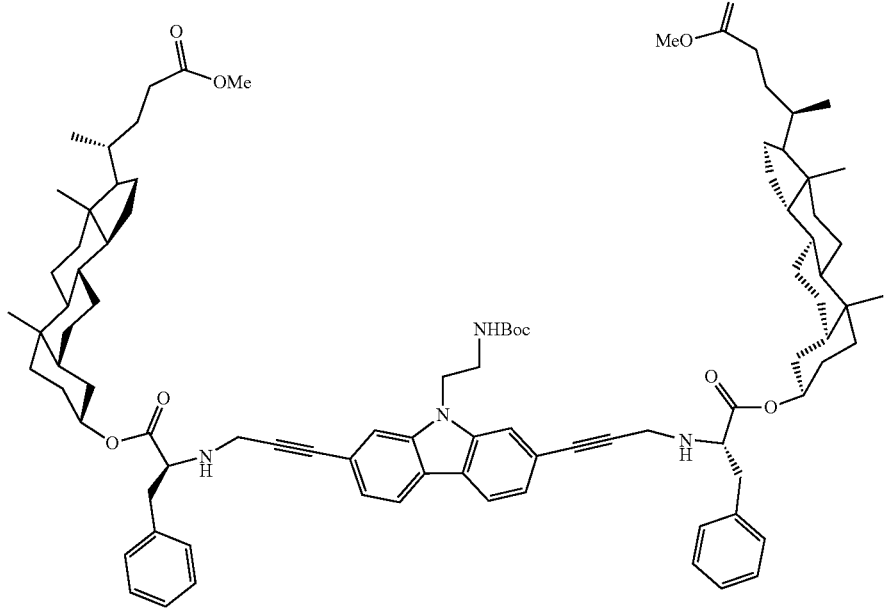
X18
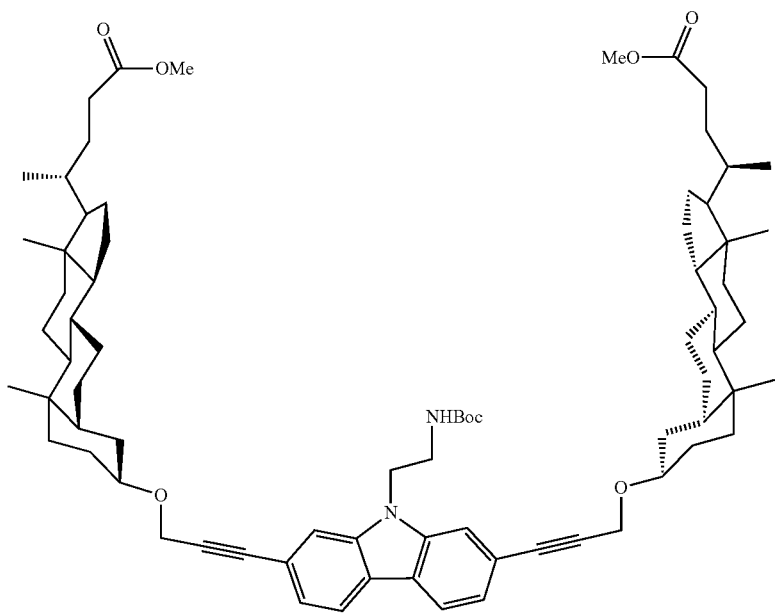
X25

X23

The present invention further provides the use of a compound as defined herein for the detection, isolation and/or detoxification of an ionophoric compound.

The present invention also provides a pharmaceutical composition comprising a compound as defined herein and a pharmaceutically acceptable excipient of carrier; more specifically, for use in human and/or veterinary medicine.

The present invention further provides the compound or the composition as defined herein for use in the diagnosis, prevention and/or treatment of disorders caused by ionophoric compounds, such as for example neurological disorders, cancer, food poisoning, heart disorders, and encephalopathy. Said ionophoric compounds may be selected from the list comprising the mycotoxins beauvericin or enniatins; ionophoric polyether antibiotics, such as monensin A and salinomycin; emetic toxins such as cereulide; or the bacterial ionophore valinomycin.

The present invention further provides a method for the prevention and/or treatment of at least one disease or disorder being caused by an ionophoric compound; said method comprising administering to a subject in need thereof a therapeutically effective amount of a compound or a pharmaceutical composition as defined herein.

In yet a further aspect, the present invention provides a solid support having attached thereto a compound of the present invention, for use in solid phase extraction of ionophoric compounds, for purification of ionophoric compounds using liquid chromatography, or for decontamination of food products containing these compounds.

Finally, the present invention provides the use of a compound or a solid support of the present invention in solid phase extraction of ionophoric compounds, in purification of ionophoric compounds using liquid chromatography, or in decontamination of food products containing these compounds.

EXAMPLES

Example 1

In this first example, the synthesis of a synthetic receptor showing high affinity for the ionophoric cyclodepsipeptide toxin beauvericin is described. Binding results in a pronounced increase in fluorescence intensity of the receptor, while this increase is not observed for a very similar ionophore such as valinomycin.

Synthesis of Synthetic Receptor with Affinity for Beauvericin

Scheme 1. Synthesis of the artificial receptor G with affinity for beauvericin

-continued
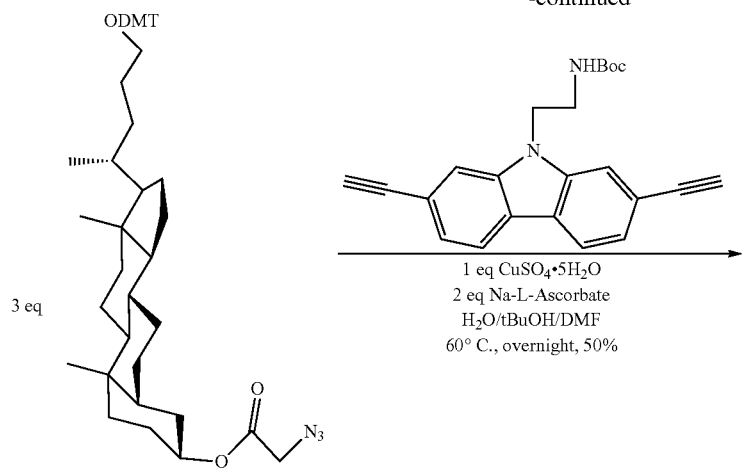
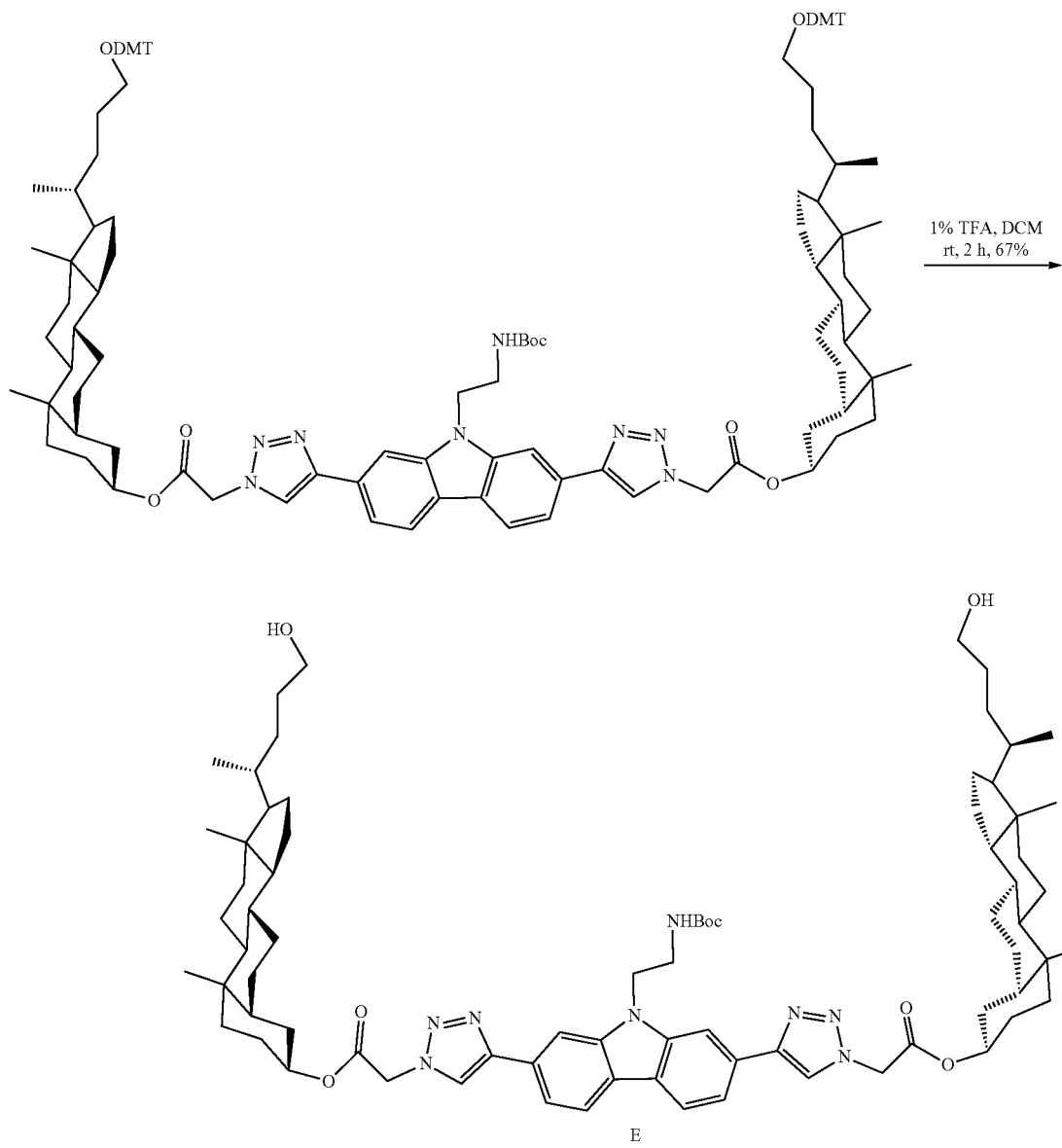

-continued
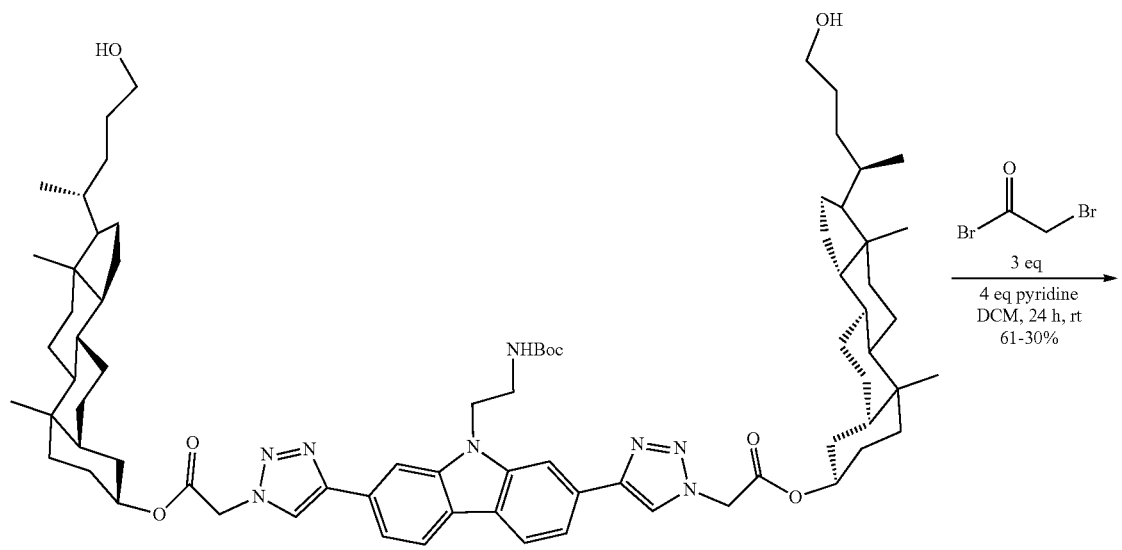
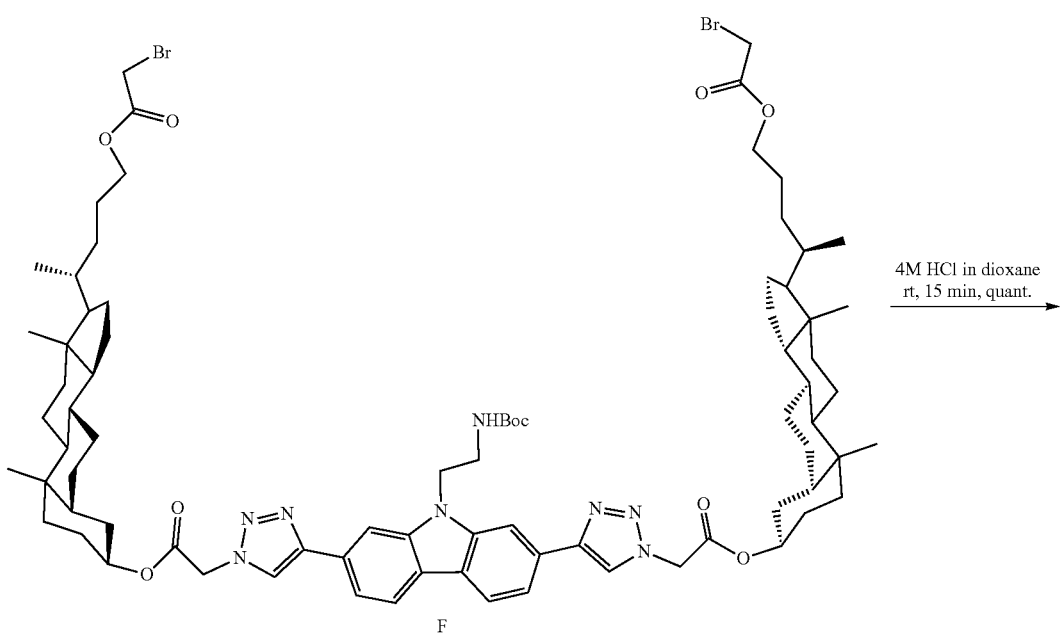

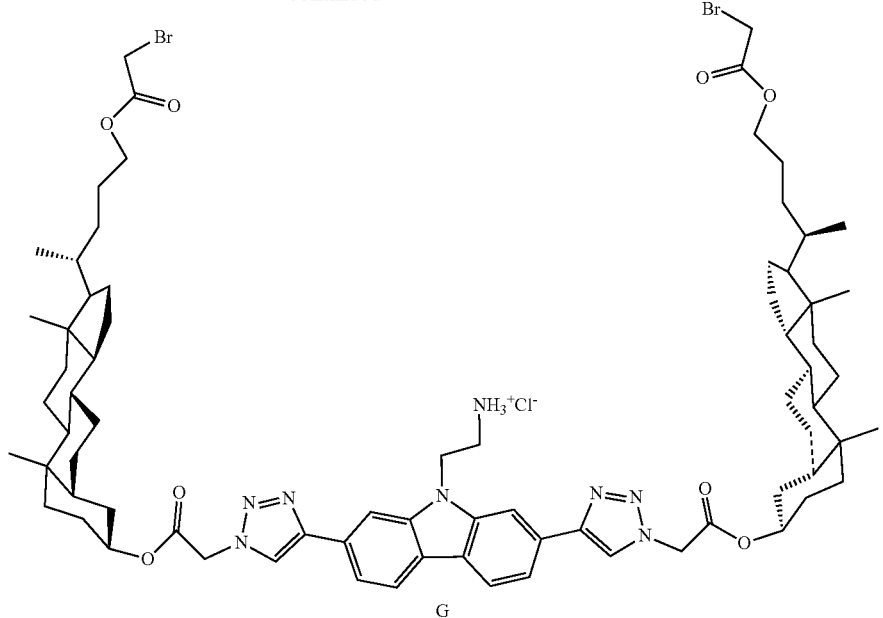

G

During the synthesis of compound A it is important to use a distillation setup in which the acetone, which is formed during the reaction, can be removed from the reaction mixture via distillation. For the work-up of reaction product C and F it is mandatory to remove the pyridine using a 10% (w/v %) $CuSO_4$ solution before evaporating the solvent in vacuo in order to avoid degradation.

The convergent synthesis of the receptor (Scheme 1) involves two fragments: a steroid fragment D and a carbazole fragment A, which are joined together via a copper-catalyzed alkyne azide cycloaddition (CuAAC) to yield the bipodal receptor E after some manipulations.

For the steroid fragment we started from commercially available lithocholic acid. Carboxylic acid reduction was performed in two steps: esterifying the carboxylic acid via Fisher esterification using MeOH and sulfuric acid, followed by a reduction with full conversion to the primary alcohol using $LiAlH_4$. For the protection of the primary alcohol in the presence of the secondary alcohol, we originally planned on using the tert-butyldiphenylsilyl (TBDPS) group. Even though we managed to successfully complete the synthesis, deprotection using tetrabutylammonium fluoride (TBAF) caused degradation of the product. When the basicity of TBAF was buffered with acetic acid almost no deprotection took place. We thus decided to replace the TBDPS group by the dimethoxytrityl (DMT) protecting group. The synthesis of the DMT-protected steroid derivative B proceeded smoothly with a yield of 54% over 3 steps.

Next, acetylation with bromoacetylbromide was undertaken. Using $K_2CO_3$ as a base, a red color immediately appeared, indicating undesired DMT deprotection while the use of pyridine as solvent and base resulted in poor conversion. When the reaction was performed in dry DCM with 4 eq pyridine, the product could be obtained in a reasonable yield. The final steroid fragment 1 could be obtained without any difficulties through an $S_N2$ reaction with $NaN_3$.

For the synthesis of the carbazole fragment, N-alkylation of 2,7-dibromocarbazole allowed the introduction of the required primary amine, necessary for complexation within the beauvericin interior. In the next step, we observed a strong solvent dependence on the outcome of the Sonogashira reaction. Using $THF/Et_3N$ (1:1) as a solvent only poor conversion was observed, while addition of DMF slightly improved the yield but was still unsatisfactory. The best results were obtained with pure $Et_3N$ as a solvent, which resulted in a yield of 89%. Subsequently, the 2-hydroxypropyl protecting group must be removed. In literature this is typically achieved using either NaOH or KOH in refluxing toluene. However on this particular substrate, no reaction took place using NaOH, probably due to its low solubility. Also KOH, though being more soluble, resulted in a low yield of 30%. We managed to solve this problem by using NaH in toluene, which allowed the synthesis of compound A with a yield of 62%.

With these two building blocks at hand we could proceed to the construction of the bipodal receptor using the CuAAC reaction. While typically this "click" reaction is very efficient, no reaction took place at room temperature using standard Fokin-Sharpless conditions. By heating the mixture at 60° C. overnight, the desired CuAAC product could be obtained. In principle, at this stage, deprotection of both DMT and Boc group would yield a functional receptor. However, the limited solubility of the resulting construct in DMF only, severely limits its future application. Therefore, the free alcohols were acetylated to render the receptor more hydrophobic. After Boc deprotection with 4M HCl in dry dioxane, we were glad to observe that the final receptor G was indeed soluble in $CHCl_3$. With our receptor at hand we could then proceed to determine its affinity for beauvericin.

Analysis of Synthetic Receptor with Affinity for Beauvericin

Figure 2:
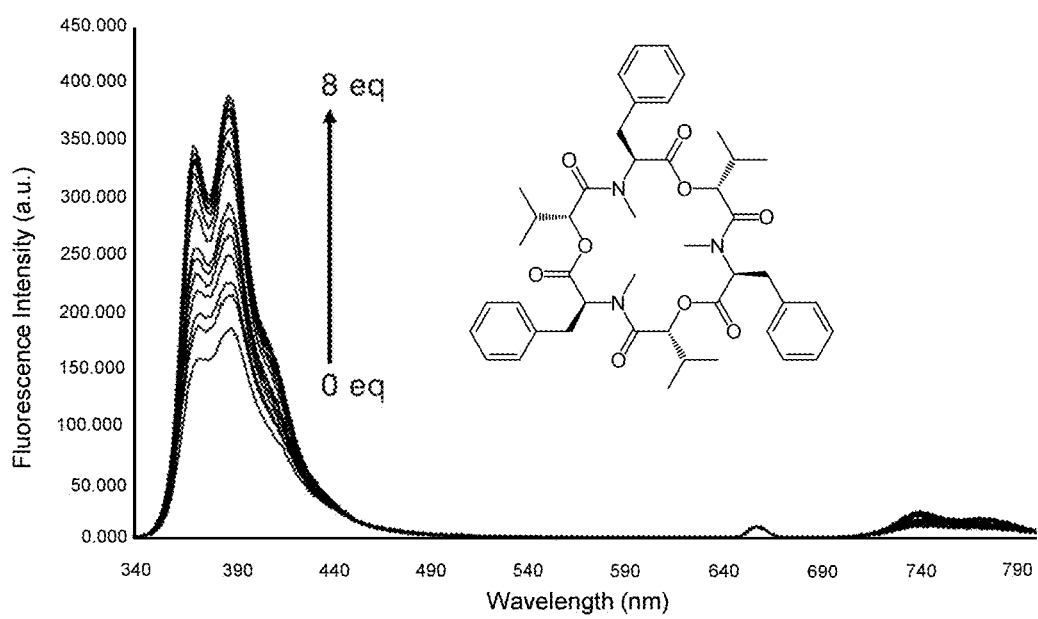
FIG. 2. Fluorescence titration of 0 to 8 eq beauvericin (BEA) to 2.5 µM receptor G in CHCl$_3$ using $\lambda_{ex}$=329 nm. The chemical structure of beauvericin is shown on the right.

It is known that fluorescence is highly dependent on the molecular environment. We therefore reasoned that binding of beauvericin in close proximity to the fluorescent carbazole moiety, would influence the local environment, thus permitting the use of fluorescence titration for the determination of binding affinity. Gratifyingly, upon addition of beauvericin to receptor G a clear concentration dependent increase in fluorescence is observed around 373 nm and 389 nm (FIG. 2) which corresponds to the typical blue carbazole emission.

Figure 3:
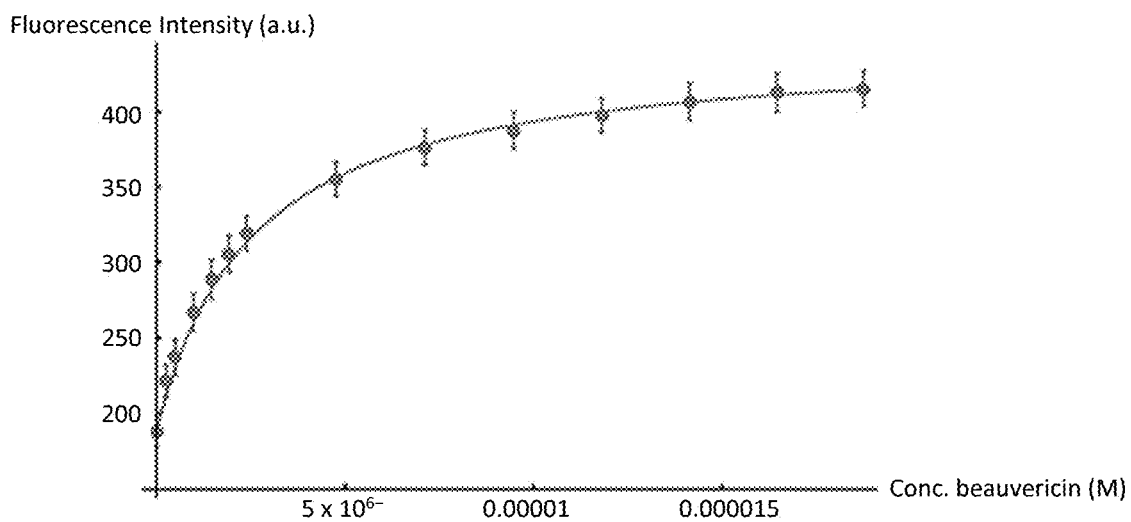
FIG. 3. Mean fluorescence intensity of compound G at 389 nm in function of added beauvericin concentration. The mean and standard error at each titration point were calculated based upon 3 independent titrations. Data points were fitted to a 1:1 stoichiometry.

When this increase in fluorescence intensity is plotted versus the added ligand concentration, a binding curve is obtained. As shown in FIG. 3, this curve can be fitted to a 1:1 stoichiometry resulting in a mean association constant of $3.99 \cdot 10^5$ $M^{-1} \pm 2.05 \cdot 10^4$ ($K_a \pm SD$). Even though the Job plot has been the golden standard in terms of determining binding stoichiometry, multiple authors have raised concerns and criticized its use in supramolecular chemistry. It has therefore been recommended to fit the data to different binding models and to asses which model explains the experimental data most satisfactory. When trying to fit the above titration points to a 1:2 or 2:1 host-guest stoichiometry (data not shown), no proper fit could be obtained. The fact that a good mathematical fit can be found for a 1:1 binding model and no reasonable fit is achievable using either 1:2 or 2:1 binding models, confirms that the observed binding is best explained based upon a 1:1 stoichiometry.

Figure 4:
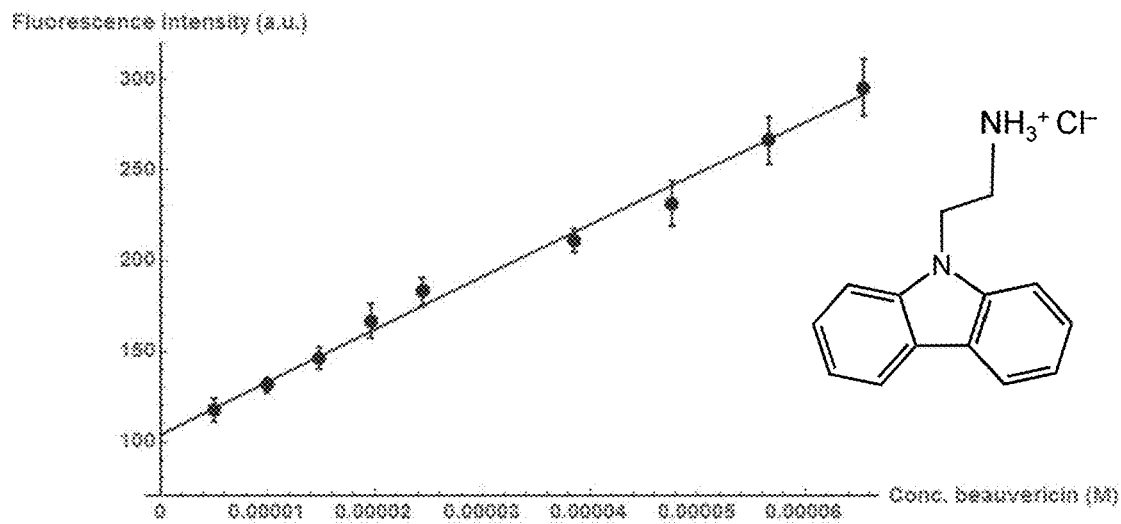
FIG. 4. Mean fluorescence intensity at 365 nm of the carbazole fragment (shown on the right) in function of added beauvericin concentration. The mean and standard error at each titration point were calculated based upon 3 independent titrations. Data points were fitted to a 1:1 stoichiometry.

As expected, when the amine is still Boc protected no change in fluorescence is observed (data not shown). More importantly when only the carbazole fragment is tested without the steroid arms, a much weaker association (factor $10^3$ smaller) is observed (FIG. 4). This decrease in binding strength clearly emphasizes the role of the hydrophobic cavity generated by the steroid arms.

Fitting the titration data gave a mean $K_a=385$ $M^{-1}$ for the carbazole fragment depicted in FIG. 4. However it should be noted that due to this low value of the association constant, small variations in the experimental data can have a large impact on the absolute value of $K_a$. Instead of looking at absolute values, we therefore prefer to look at order of magnitudes. We can thus conclude that the affinity of the carbazole fragment is a factor $10^3$ smaller than receptor G.

To assess the degree of selectivity, the capacity of receptor G to bind valinomycin was also tested. This bacterial toxin is produced by *Streptomyces* spp. and like beauvericin, is an ionophoric depsipeptide with selectivity for $K^+$ and $NH_{4+}$ ions. Valinomycin has been used as the ionophore of choice in $K^+$-selective electrodes. The main difference between the two toxins is their molecular weight and size (783 Da for beauvericin and 1111 Da for valinomycin). Interestingly even though both ionophores are very similar, when valinomycin was added to receptor G, a negligible increase in fluorescence occurred (data not shown).

Conclusion

To conclude, we have described the first synthetic receptor for the ionophore beauvericin with an association constant of $3.99 \cdot 10^5$ $M^{-1}$ in chloroform. This receptor shows a pronounced increase of fluorescence intensity upon addition of the toxin. Interestingly, when a very similar ionophore such as valinomycin is added no change in fluorescence is observed, providing evidence for the selectivity of our receptor. In terms of ligand scope, the receptors with closest resemblance to the work presented herein, are synthetic receptors binding peptides. H. Wennemers et al. developed diketopiperazine hosts that complexed a tripeptide with $K_a=2.5 \cdot 10^3$ $M^{-1}$ in $CHCl_3$ (Bernard et al., 2007). While the group of J.-M. Fang were able to bind the Ac-D-Ala-Gly-D-Ala-$NH_{12}H_{25}$ tripeptide with $K_a=294 \cdot 10^3$ $M^{-1}$ in MeOH/$CHCl_3$ (1:9) using a tris(bipyridine) ruthenium(II) based receptor (Chang et al., 2005). The bowl-shaped macrobicyclic receptor synthesized by J. D. Kilburn et al., showed affinity for the Cbz-β-Ala-D-Ala-OH dipeptide with $K_a=1.2 \cdot 10^4$ $M^{-1}$ in deuteroform (Henley et al., 2000). Other synthetic receptors have been shown to bind tripeptides with association constants in the range of $10^5$-$10^6$ $M^{-1}$ in buffer/MeOH or buffer/DMSO (1:1). The affinity for beauvericin obtained with our receptor is thus comparable with those obtained for peptide receptors.

This receptor is also useful for immobilization on resin and subsequent use for solid phase extraction of beauvericin in real food samples.

Example 2

In order to be able to immobilize the receptor on a solid support, the incorporation of a suitable handle is required. For this purpose, the synthesis of a synthetic receptor containing two carboxylic acid functionalities was developed (Scheme 2).

Scheme 2. Synthesis of a synthetic receptor containing carboxylic acid functionalities. For the synthesis of the carbazole fragment we refer to scheme 1.

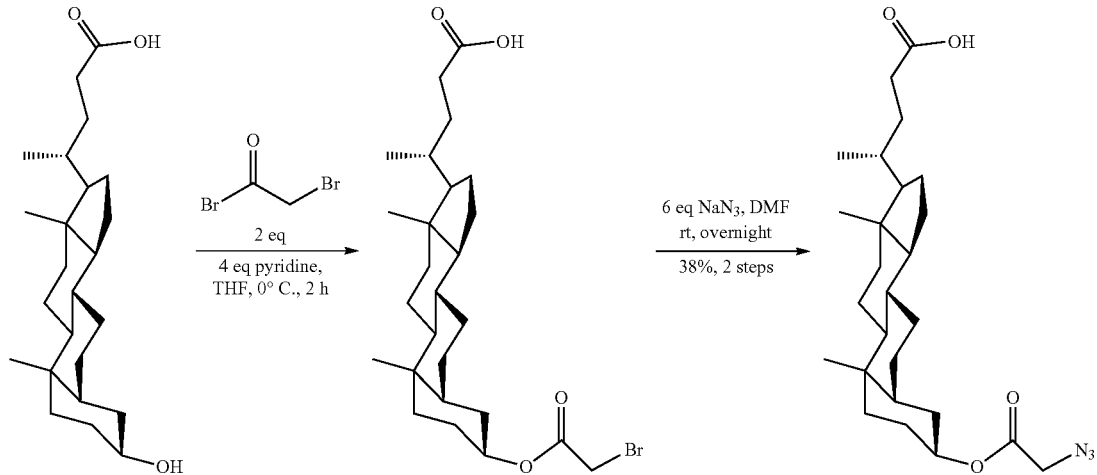

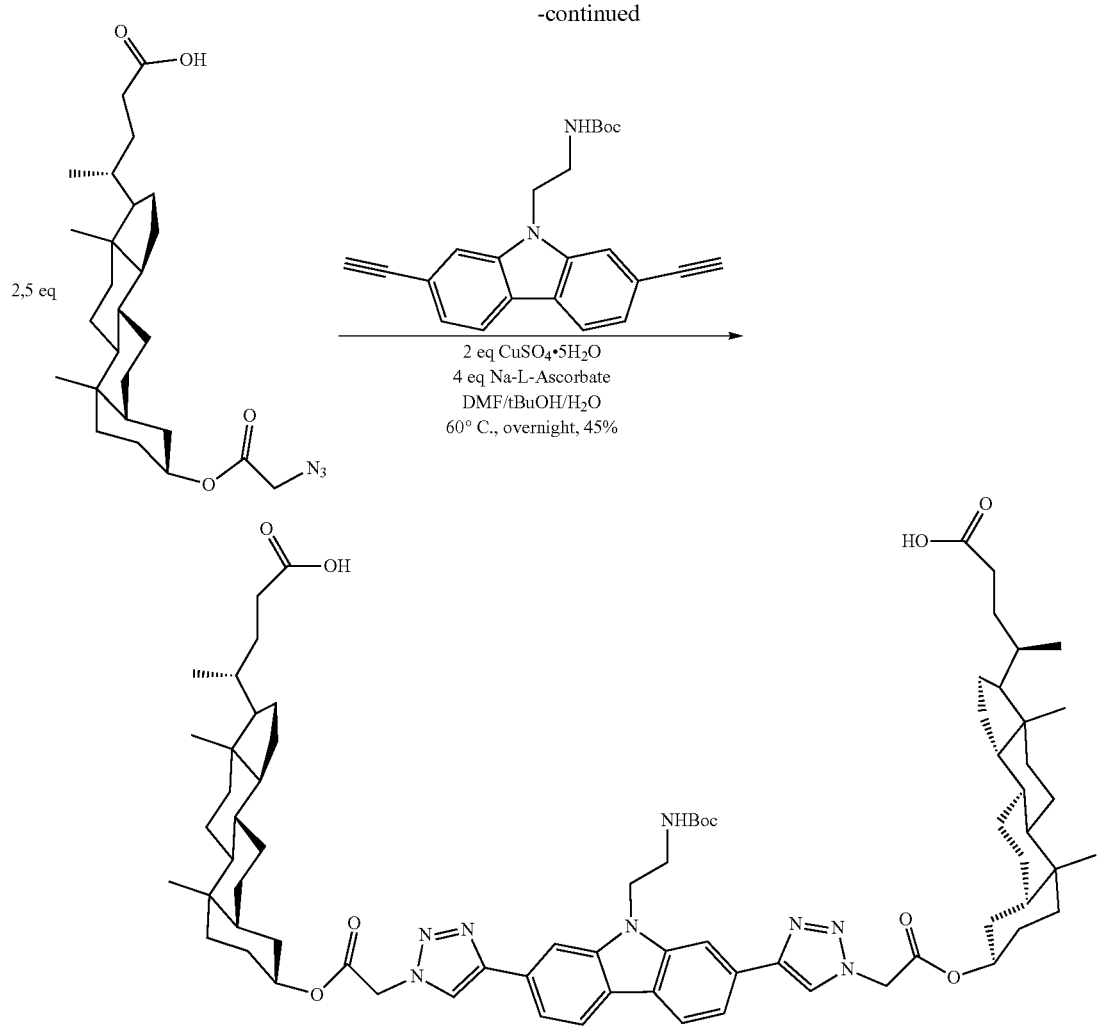
With this receptor at hand, we then performed the amide bond formation for immobilization onto the solid support. For the latter, either chemmatrix, polystyrene or 3-aminopropyl silica were used (Scheme 3).
Scheme 3. Immobilization of the synthetic receptor containing carboxylic acid functionalities onto 3-aminopropy silica.
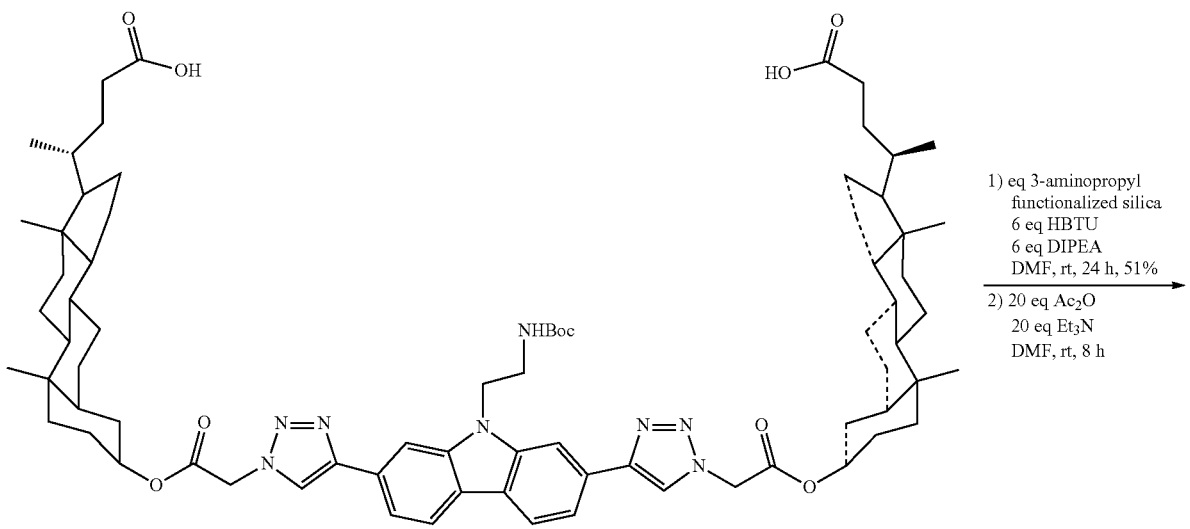

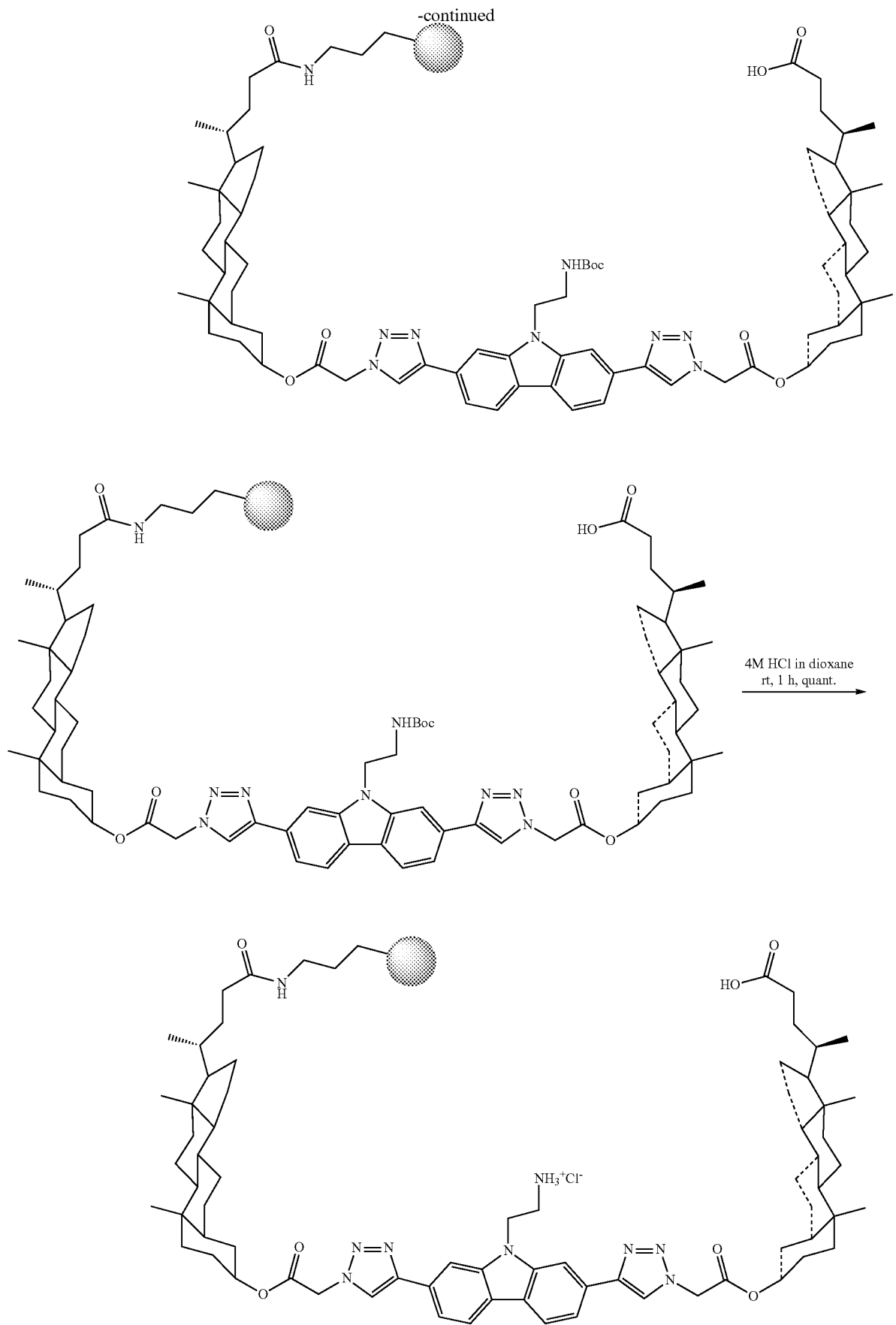

Figure 5:
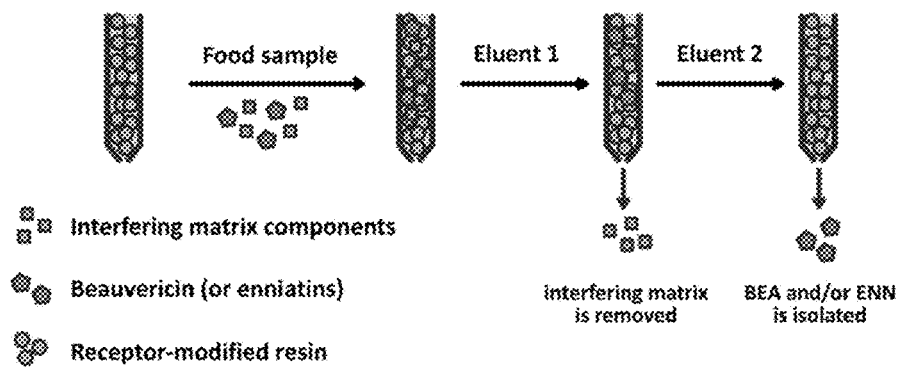
FIG. 5. Illustration of the use of the immobilized receptor for SPE purposes.
Figure 6:
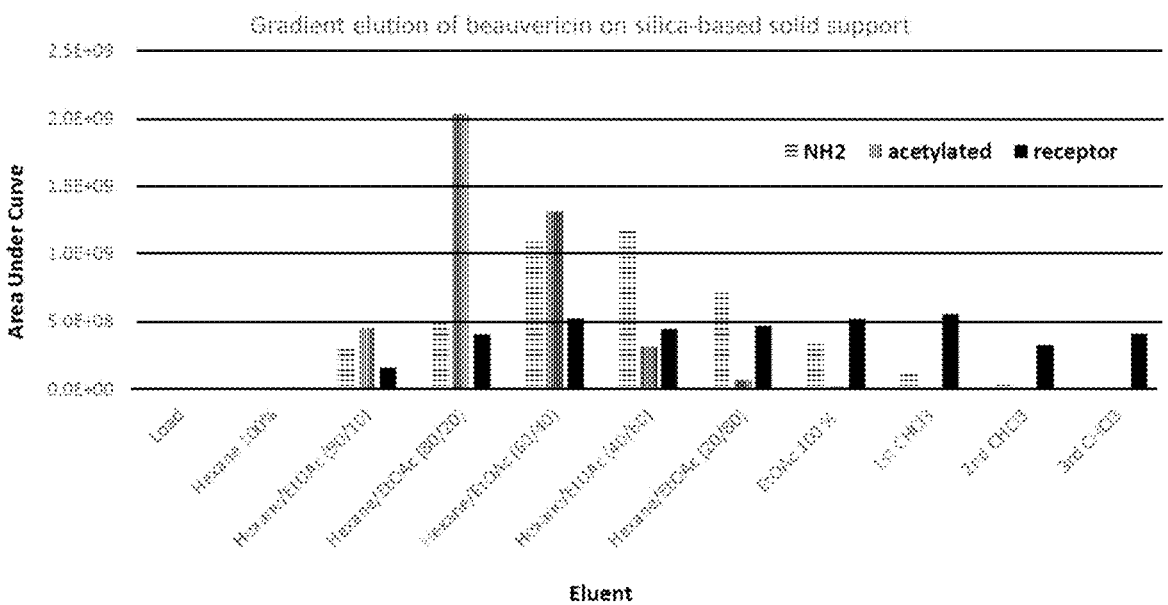
FIG. 6. Area under curve of the total ion count for the BEA ions in each elution fraction. The results for non-modified resin ($NH_2$), acetylated resin and receptor-modified resin (with the resin being silica) are shown.
Figure 7:
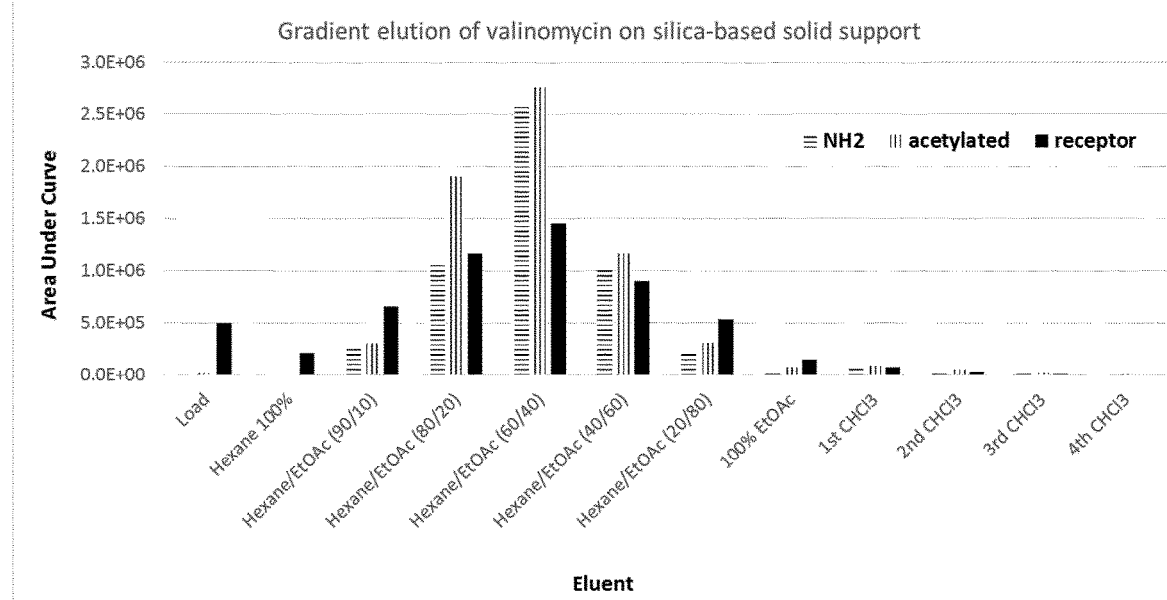
FIG. 7. Area under curve of the total ion count for the VAL ions in each elution fraction. The results for non-modified resin ($NH_2$), acetylated resin and receptor-modified resin (with the resin being silica) are shown.

The obtained immobilized receptors were subsequently tested for their capability to retain BEA which would allow its use in Solid Phase Extraction (SPE) cartridges (the principle is depicted in FIG. 5). Briefly, when a sample containing BEA is poured onto the receptor-modified resin, the high affinity of the receptor for BEA will ensure that the latter is bound strongly to the resin. Elution with a weakly or non-competing solvent such as hexane will elute the interfering matrix components in the mixture while BEA will still remain bound to the receptor. In a second step, a strong competing eluent is used (a more polar solvent such as EtOAc, $CHCl_3$ or a solvent containing an ammonium salt which can compete with the receptor for binding with BEA). This allows the elution of the toxin from the column. This method can thus be used to remove interfering matrix components or to concentrate a certain sample containing BEA.

In order to test the immobilized receptor for SPE purposes, a 100 nM solution of BEA in hexane was added to a column packed with the receptor-modified resin. After shaking overnight, the solvent was eluted (=load in graph 1) and the resin was subsequently washed with different solvent ratios, whereby the polarity was gradually increased (hence increase in competitiveness of the eluent). The same experiment was also conducted on the non-modified resin containing the amine functionality (termed NH2) and on the acetylated resin (termed acetylated) as controls (Scheme 4). Quantification of the BEA concentration in each elution fraction was performed using standard LC-MS procedures for BEA detection.

sites for BEA, the retention is purely non selective and the obtained results are illustrative for the background absorption resulting from the resin material itself. The non-modified resin on the other hand contains the amine functionality but lacks the hydrophobic pocket of the receptor. Indeed, a stronger retention was observed compared to the acetylated resin. Gratifyingly, the receptor-modified resin (which contains both the amine and the hydrophobic cavity) shows a stronger retention of BEA compared to the other two resins, thereby highlighting the added value of the receptor construct for the binding of BEA. Moreover, the results obtained in this SPE experiment nicely complement the results obtained via fluorescence titration.

Interestingly, when the same experiment was conducted using a solution containing valinomycin (VAL) instead of BEA, no difference was observed between the resins (FIG. 7). This validates the observation made during the fluorescence titration of VAL with the receptor (vide supra).

To conclude, immobilization of the receptor on a silica solid support allows the selective retention of BEA compared to VAL and opens-up the possibility of utilizing this receptor-modified resin for SPE.

Example 3

A shorter synthesis route for a functional synthetic receptor was developed whereby a methyl ester functionality was introduced at the C24 end of the steroid fragment instead of the previously described acetylbromide end group (Scheme 5). This allows the synthesis of the receptor on a larder scale compared to what can be achieved with the acetylbromide derivative (Scheme 1).

Scheme 4. Depiction of (from left to right): receptor-modified resin, acetylated resin and non-modified resin (NH2).

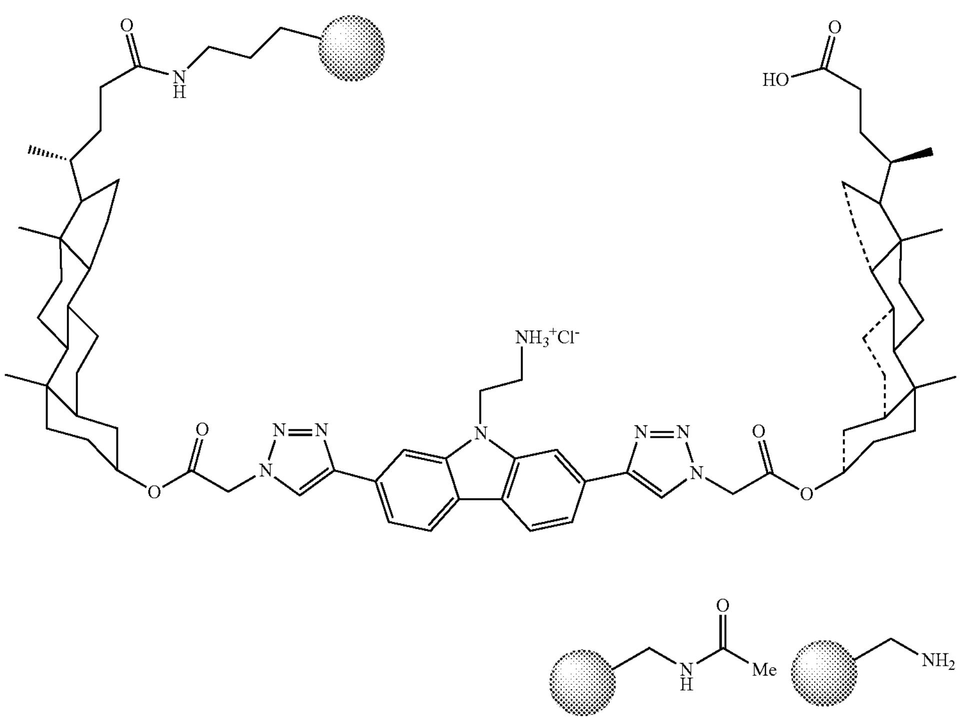

As can be seen from FIG. 6, when the resin is acetylated, BEA elutes earlier compared to the other two resins. Because the acetylated resin does not contain any binding Scheme 5. Synthesis of the methyl ester derivative.
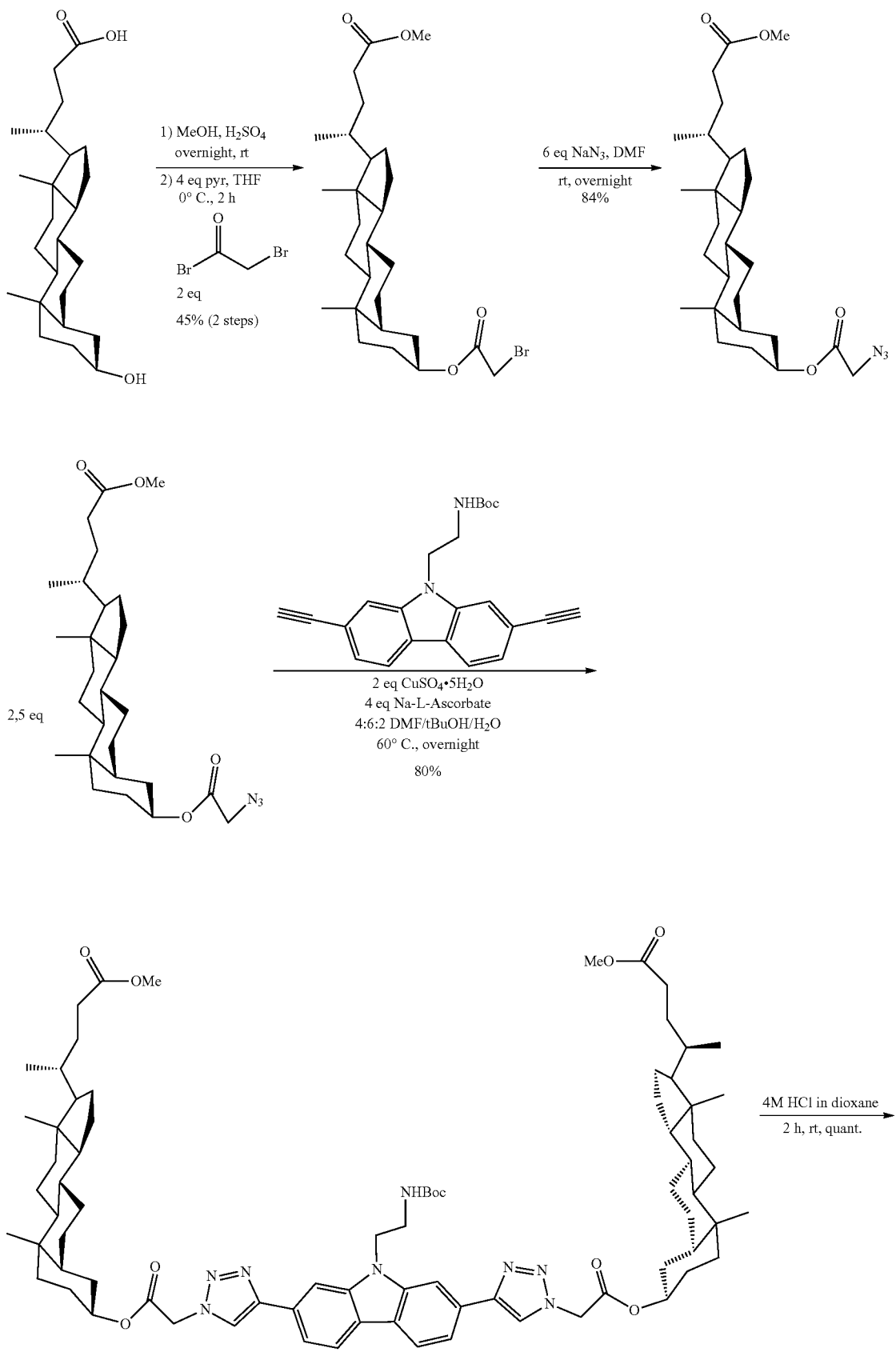

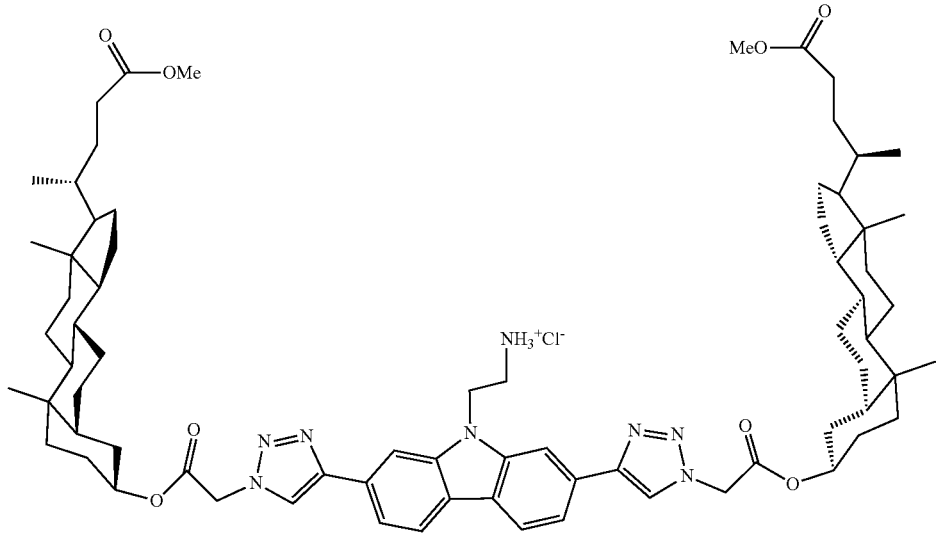

Fluorescence titration of this methyl ester derivative with BEA yielded a $K_a=1.1\cdot10^5$ M$^{-1}$ which is in the same order of magnitude but a factor 4 lower compared to the acetylbromide derivative ($K_a=4.0\cdot10^5$ M$^{-1}$). The methyl ester derivative was subsequently used for the detection of BEA in real food samples and biological fluids.

Figure 8:
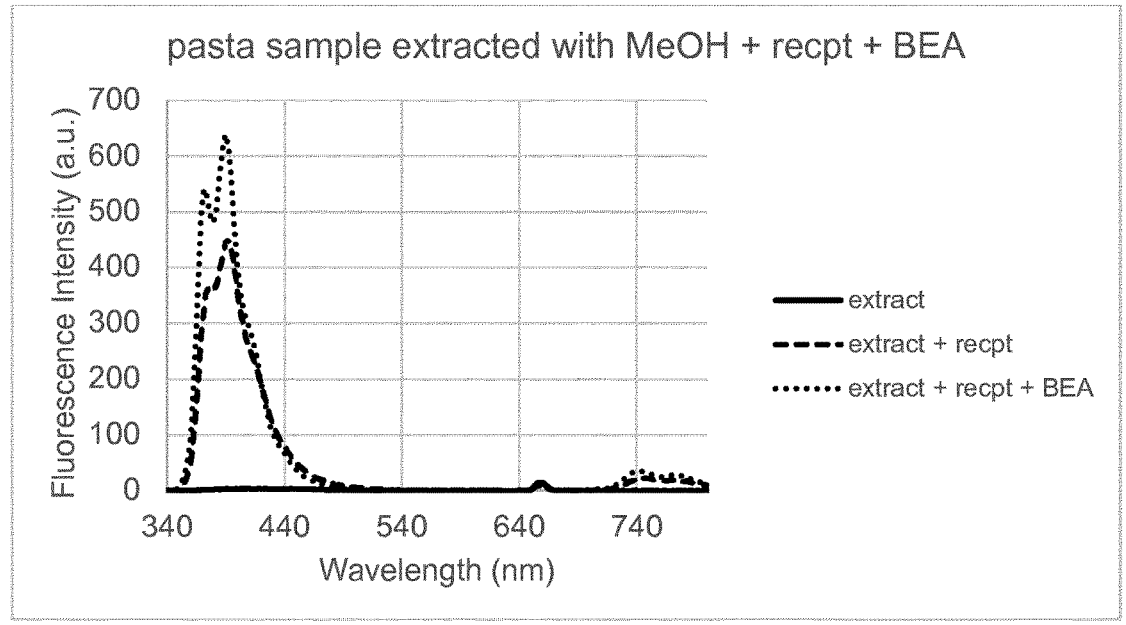
FIG. 8. Fluorescence intensity of pasta extract without methyl derivative (full line), with methyl derivative before addition of BEA (dashed line) and after addition of BEA (dotted line) in $CHCl_3$.

Briefly, 26 g pasta was cooked and extracted with 20 ml MeOH. The solvent was then evaporated and reconstituted in CHCl$_3$. Addition of 10 µM of the methyl ester derivative to this extract gave similar fluorescence intensity as was the case in pure CHCl$_3$. Interestingly, addition of 2 eq BEA to this extract resulted in a pronounced increase in fluorescence intensity (FIG. 8), thus indicating that the receptor can still detect BEA in food extracts. Similar results were obtained in maize extracts.

A similar experiment was conducted in a urine sample in order to asses if the receptor can be applied in biological fluids. During this experiment, 3 ml urine was extracted with 2 ml CHCl$_3$. Fluorescence measurement of the organic phase showed no background fluorescence (full line, FIG. 8). Addition of 10 µM of the methyl ester derivative to this extract gave similar fluorescence intensity as was the case in pure CHCl$_3$ (dashed line, FIG. 8). Also here, addition of 2 eq BEA to this extract containing the methyl ester derivative resulted in an increase in fluorescence intensity (dotted line, FIG. 8). The synthetic receptor is thus still functional even in biological samples such as urine extracts.

To conclude, the above experiments indicate that the synthetic receptor presented herein can still function even in complex matrixes such as pasta or urine extracts.

Example 4

In order to assess the importance of the hydrophobic moiety, we also synthesized a receptor based on dehydroabietylamine instead of lithocholic acid, the synthesis of which is depicted in scheme 6.

Scheme 6. Synthesis of dehydroabietylamine-based receptor.

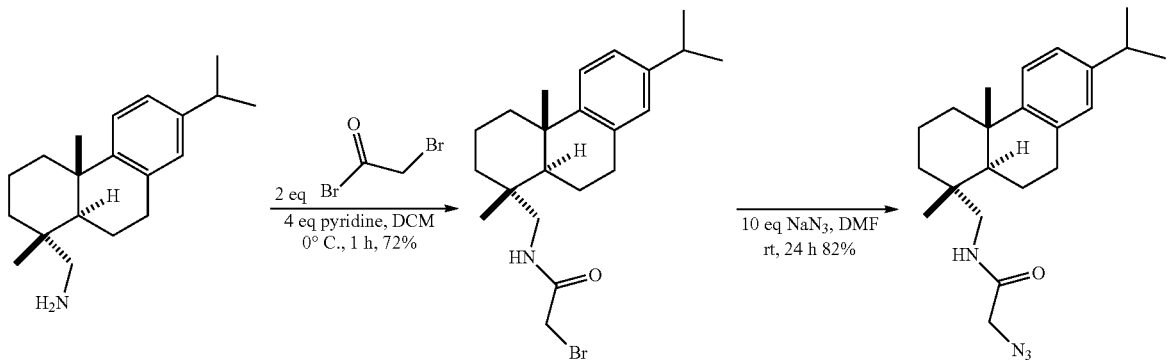

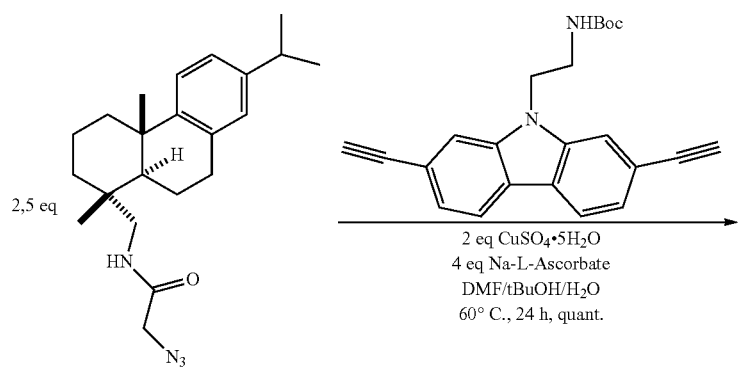
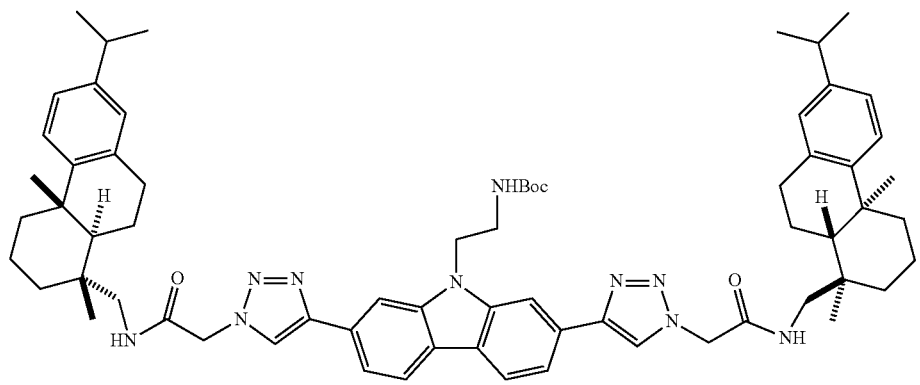
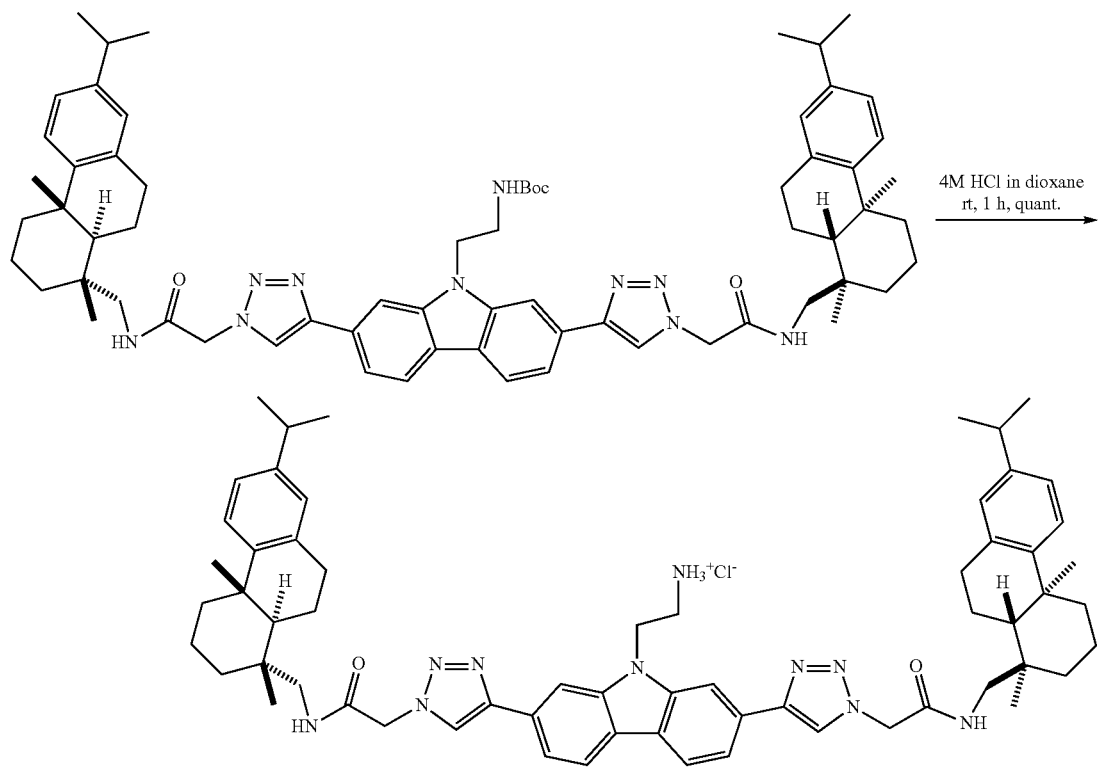

Interestingly, fluorescence titration of this receptor with BEA yielded a $K_a=1.6 \cdot 10^6$ M$^{-1}$ which is 10 times larger than what was obtained for the methyl ester derivative ($K_a=1.1 \cdot 10^5$ M$^{-1}$) and a factor 4 larger compared to the acetylbromide derivative ($4.0 \cdot 10^5$ M$^{-1}$).

Example 5

In order to investigate the influence of the cavity size, the following two derivatives were synthesized (Scheme 7 and 8). In terms of cavity size the following holds true: methyl ester derivative (largest)>receptor in scheme 8 (intermediate)>receptor in scheme 7 (smallest).

Scheme 7. Synthesis of receptor with small cavity size. For the synthesis of the carbazole fragment we again refer to scheme 1.

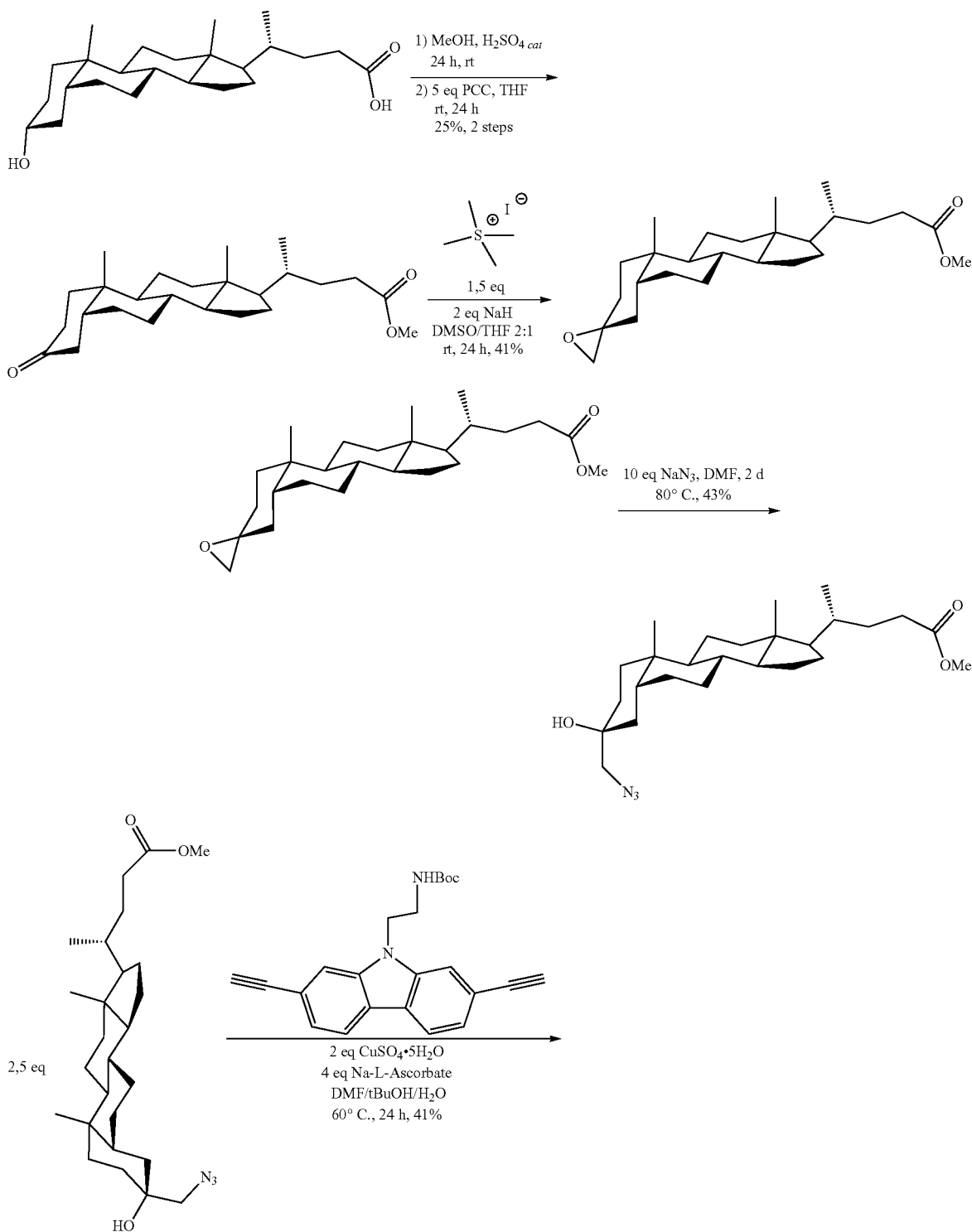

69
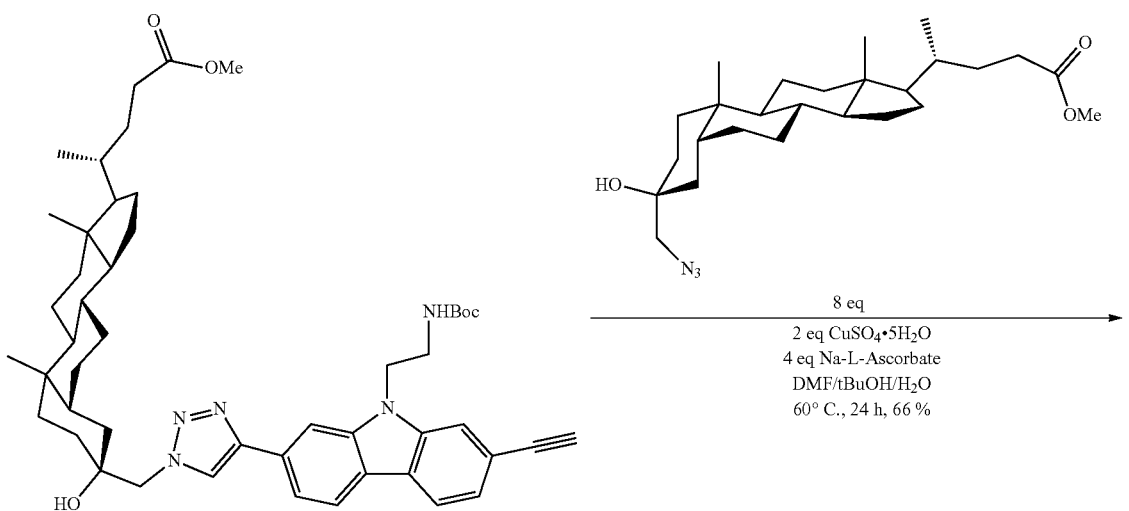
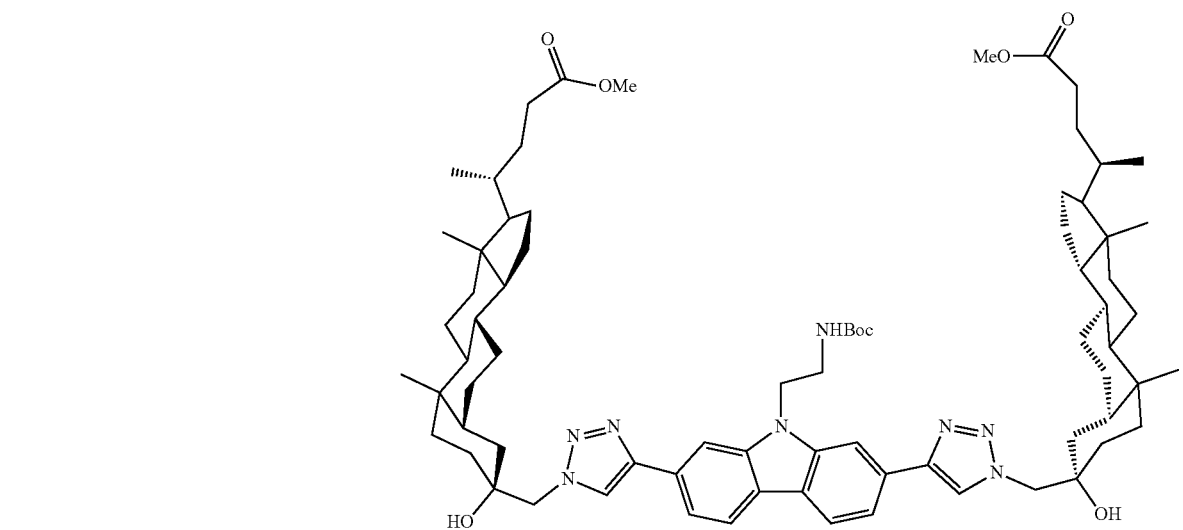
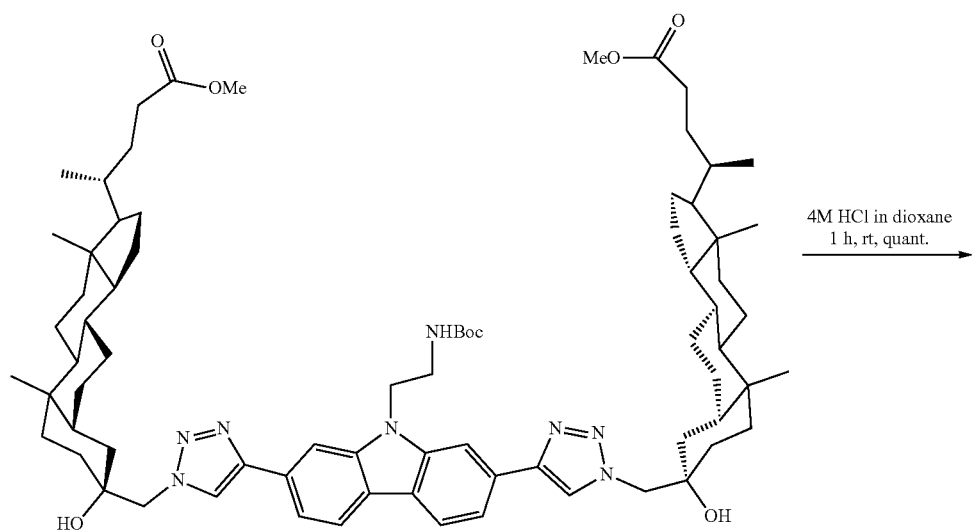

-continued
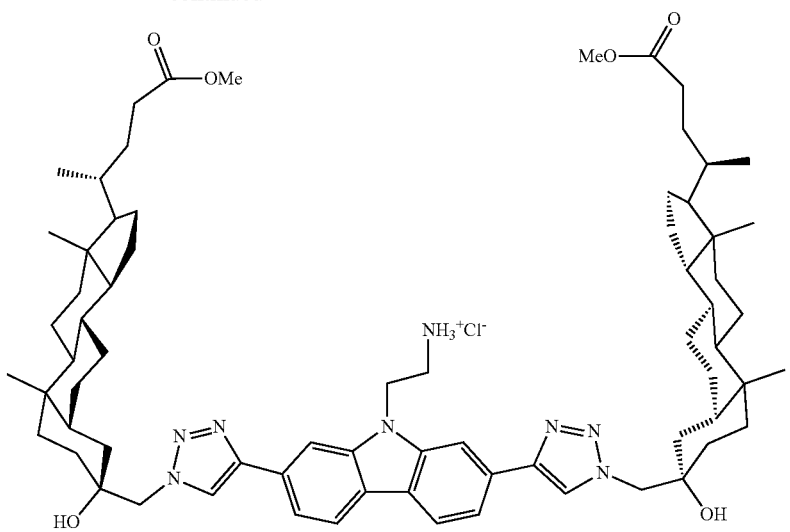
Scheme 8. Synthesis of receptor with intermediate cavity szie. For the synthesis of the starting materials we refer to scheme 7 and scheme 5.
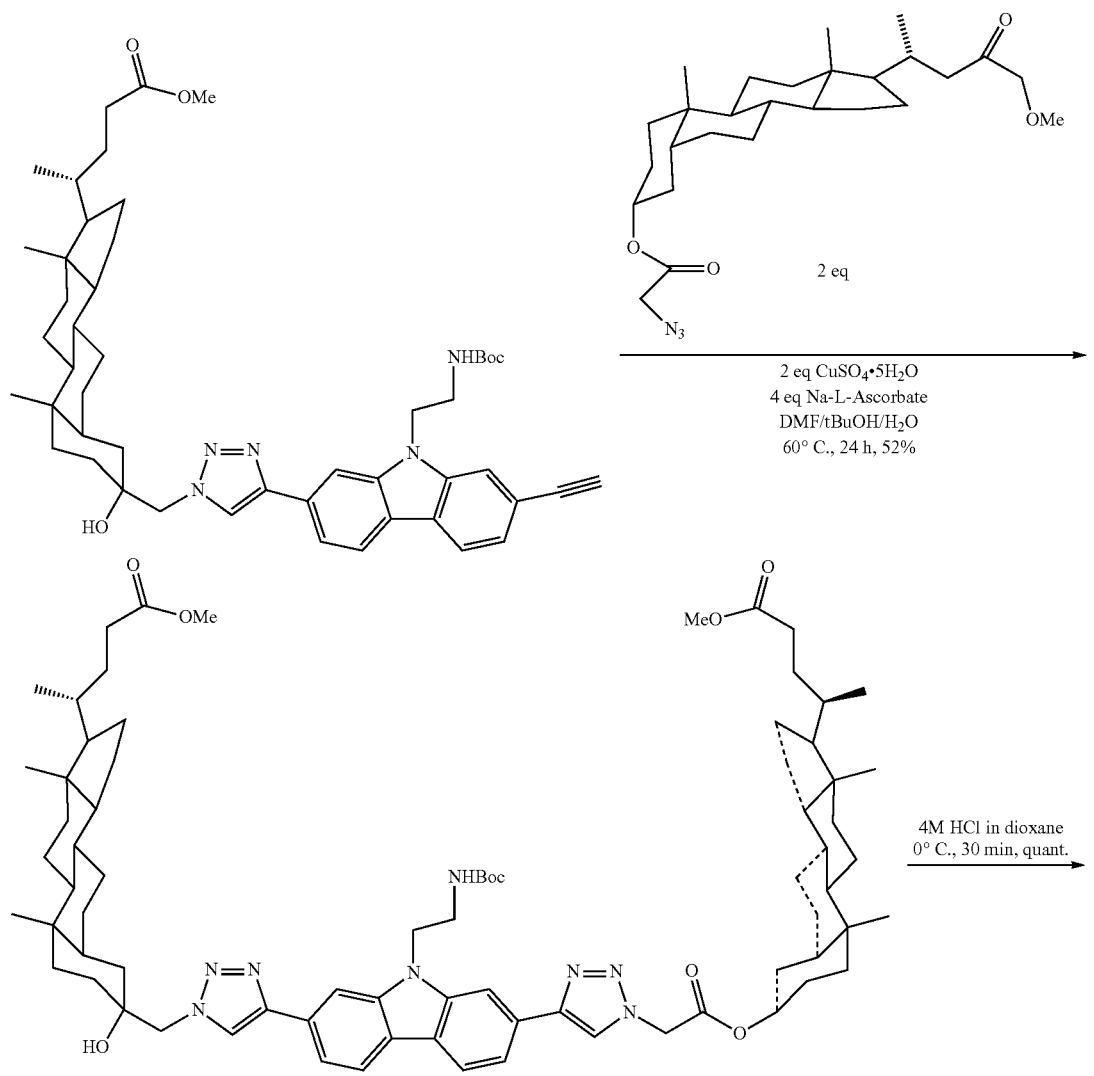
2 eq
2 eq CuSO₄·5H₂O
4 eq Na-L-Ascorbate
DMF/tBuOH/H₂O
60° C., 24 h, 52%
4M HCl in dioxane
0° C., 30 min, quant.

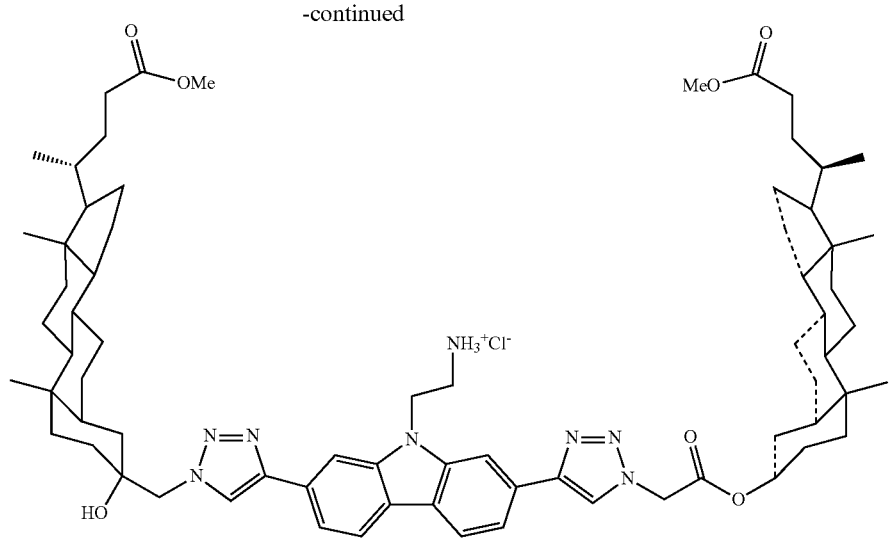

Example 6

For many applications a labeled receptor is required (ELISA, lateral flow devices, . . . ). In order to achieve this we either synthesized a receptor labeled with gold nanoparticles (vide infra) or a biotin labeled receptor (Scheme 9). Incorporation of the biotin label may allow immobilization on streptavidin coated surfaces or the enzymatic labeling of the biotin-modified receptor using streptavidin-HRP (horse radish peroxidase).

Scheme 9. Synthesis of biotin-modified receptor.

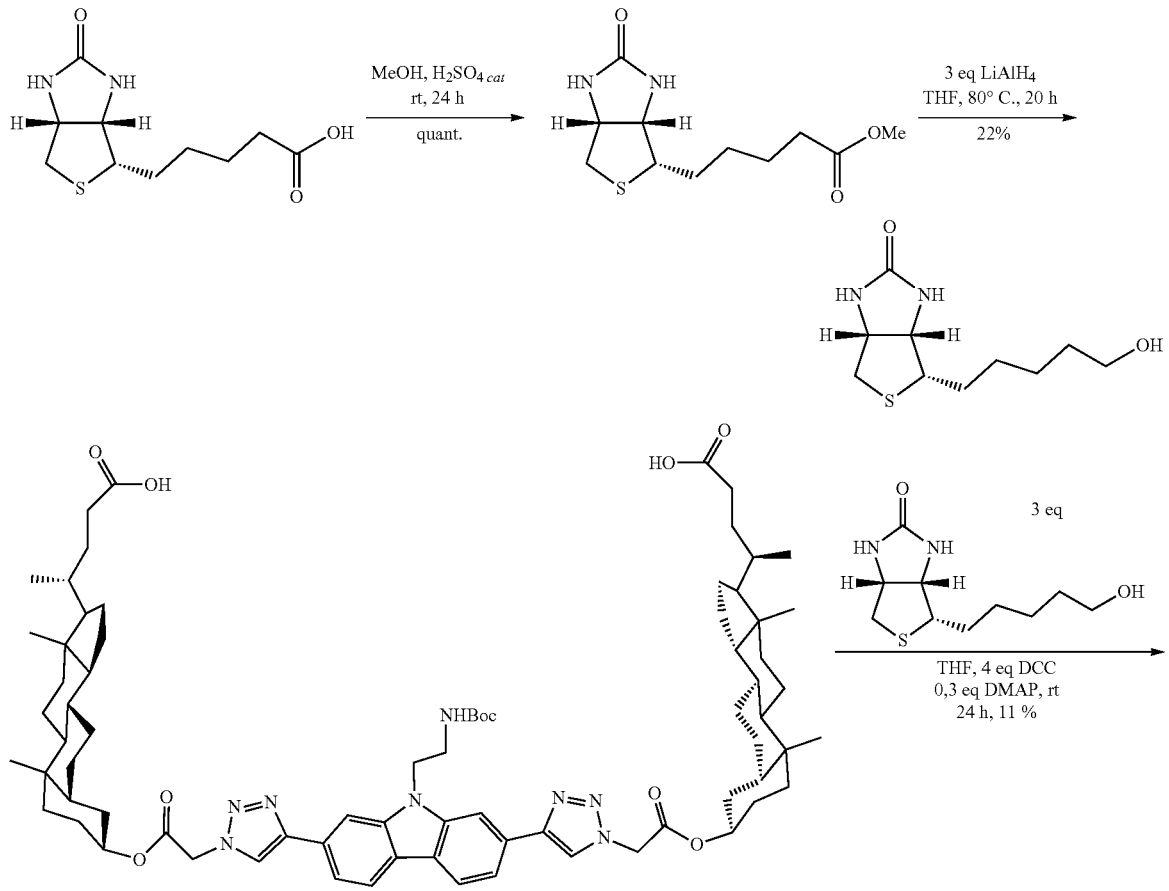

-continued
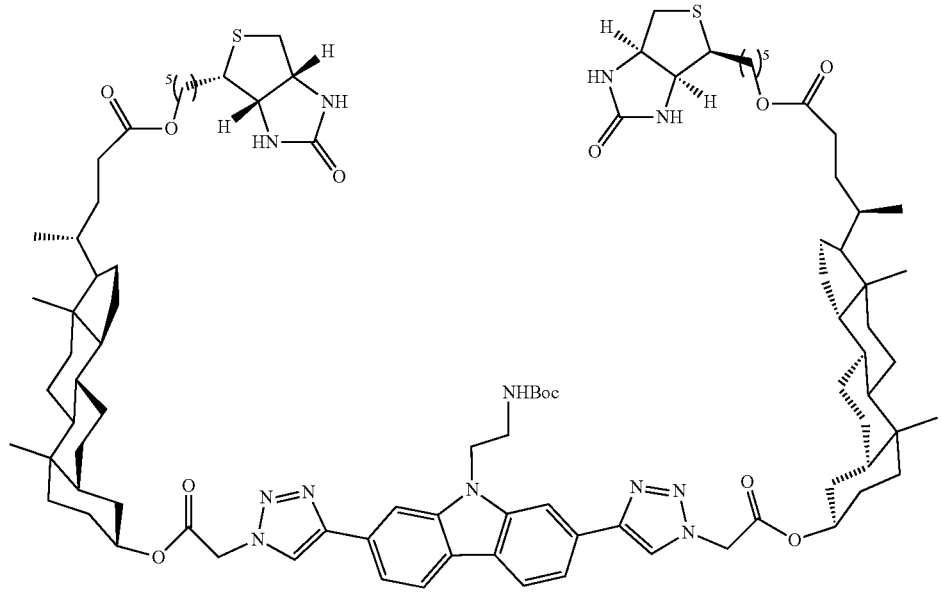
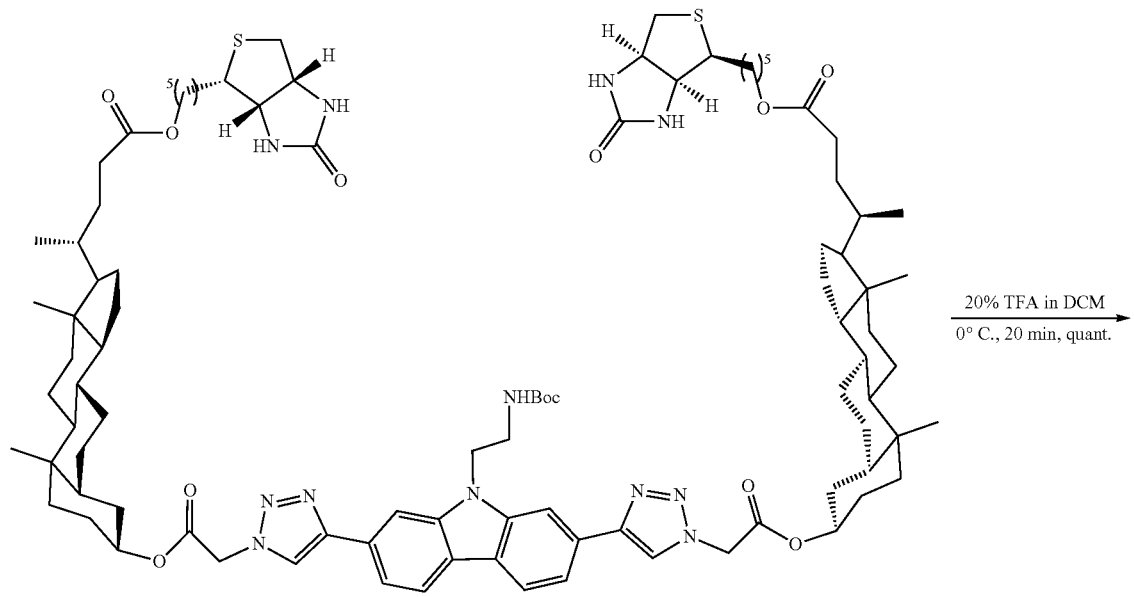
20% TFA in DCM
0° C., 20 min, quant.

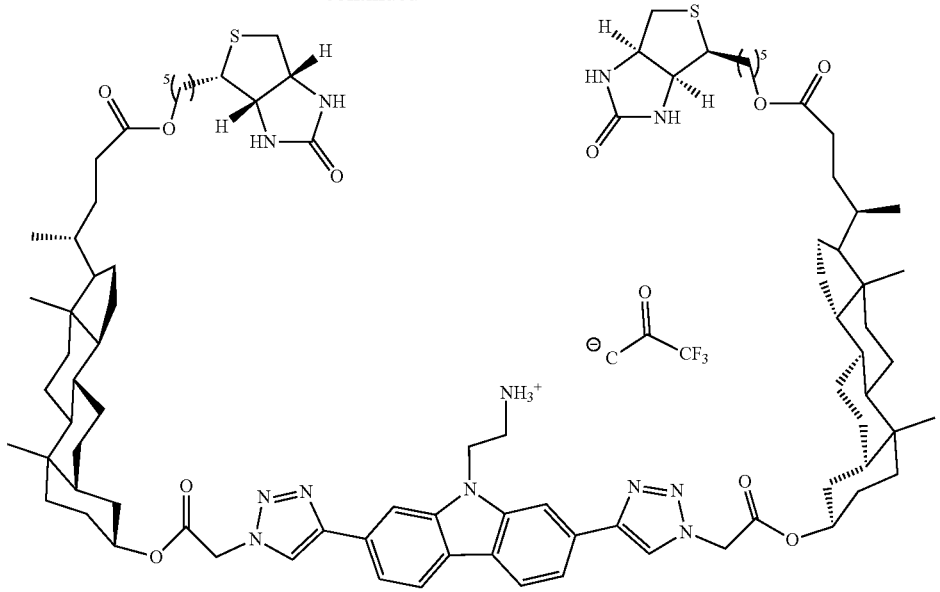

Example 7

Next to the synthesis of a biotin-modified receptor for concomitant labeling of this construct with streptavidin-enzyme conjugates, we also developed a lipoic acid modified receptor (Scheme 10) which was subsequently coupled to gold nanoparticles as labels.

For the synthesis of water-soluble gold nanoparticles, 79 mg HAuCl$_4$·3H$_2$O was dissolved in 180 ml milliQ water and heated. Once the solution is boiling, the solution is stirred another 30 min while heating. Then a citrate solution (200 mg trisodium citrate dihydrate in 20 ml milliQ water) is added in one portion and after 3 min the solution is cooled to room temperature. Thus yielding non-modified gold nanoparticle solution.

For the modification with the receptor, the lipoic acid derivative (0.1 mg) dissolved in DMF (5 µL) was added to 1 ml of the colloidal gold solution and the mixture was stirred for 24 h at rt. Centrifugation was used, followed by removal of the supernatant. MilliQ water was added and this was repeated once in order to remove impurities. Finally the particles were redissolved in water yielding the receptor modified colloidal gold particles.

Also the synthesis of hydrophobic gold nanoparticles is possible which are soluble in organic solvents such as CHCl$_3$. To achieve this, 104 mg HAuCl$_4$·3H$_2$O was dissolved in 20 ml EtOAc and 100 µL of the lipoic acid derivative (2 mg) dissolved in DMF was added. Then a NaBH$_4$ solution is added while stirring (150 mg NaBH$_4$ in 4 ml H$_2$O) which renders the solution black. After 2 min stirring, the solution was washed with H$_2$O. The organic layer was precipitated three times (removing the supernatant every time) using centrifugation and after removal of residual solvent, the residue was reconstituted in CHCl$_3$. This yielded the colloidal gold modified with the lipoic acid derivative.

Scheme 10. Synthesis of a lipoic acid modified synthetic receptor. For the synthesis of the carbazole fragment we refer to scheme 1. For the synthesis of the steroid fragment we refer to scheme 2.

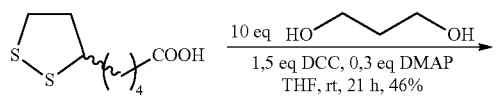

-continued
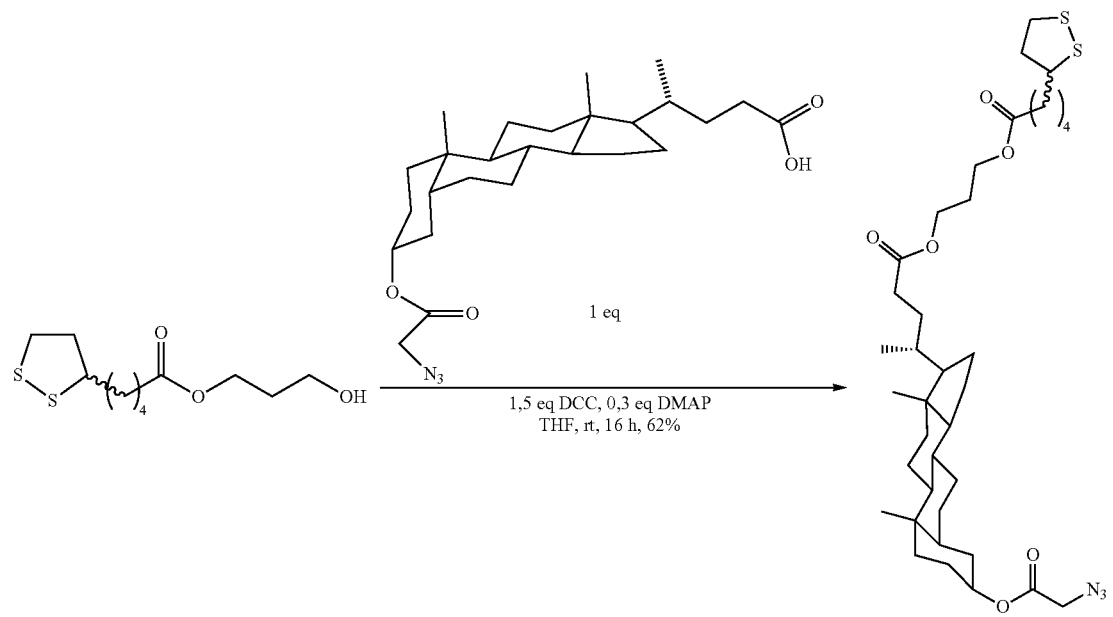
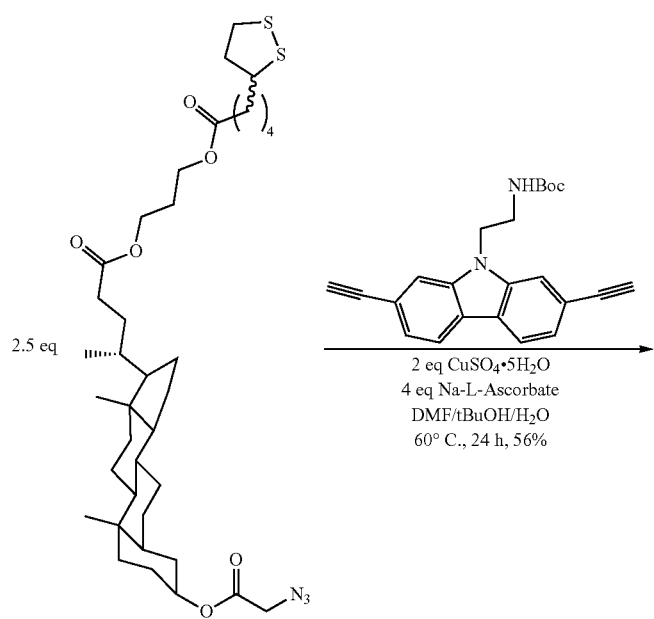

-continued

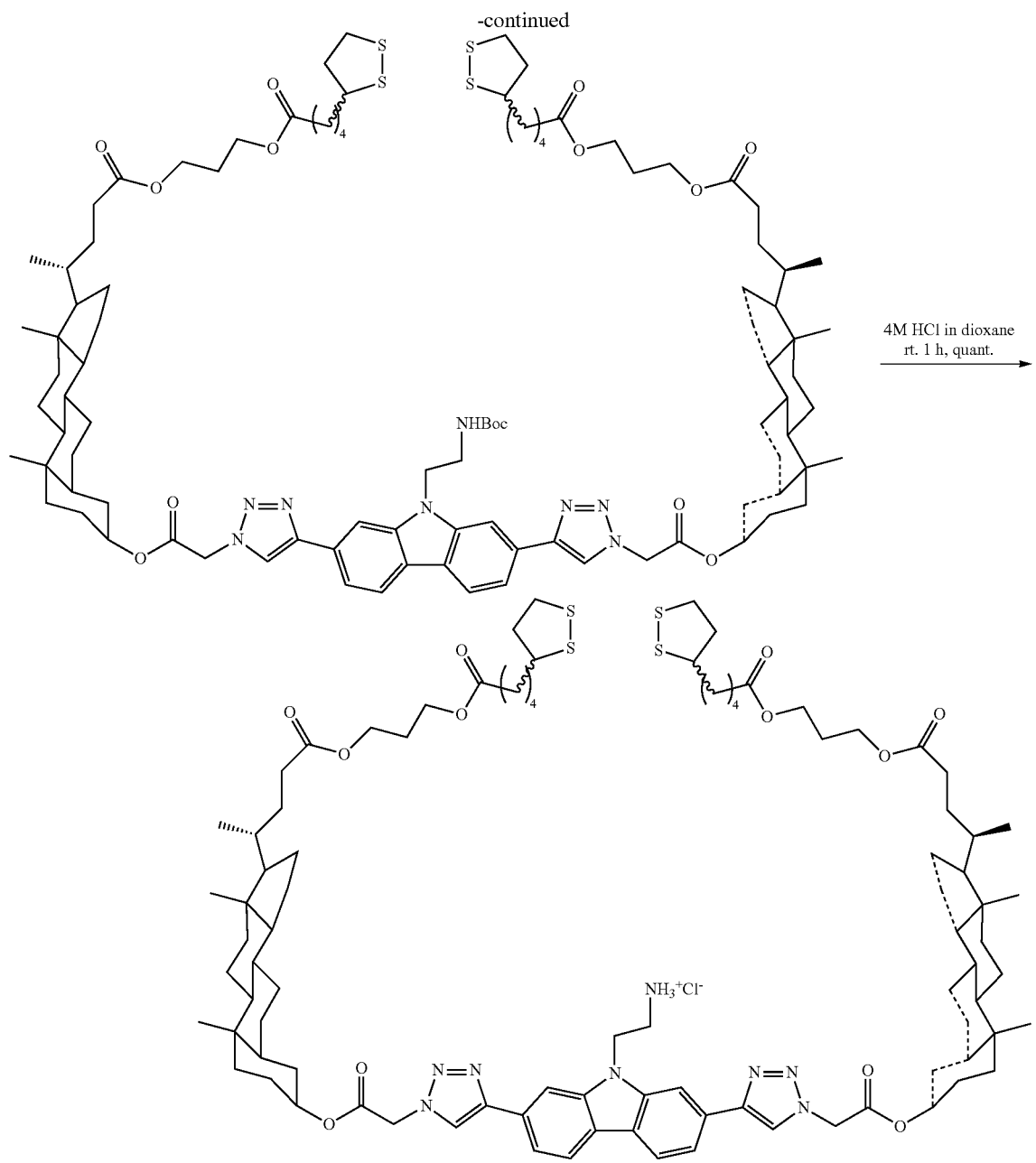

4M HCl in dioxane
rt. 1 h, quant.

Example 8

Currently, there is no antidote against ionophoric toxins such as beauvericin, enniatins or cereulide. In order to probe if receptor V1 (FIG. 9, top) could be used to counteract beauvericin intoxication, cell experiments were conducted. Knowing that this toxin accumulates in the liver, HepG2 cells (liver carcinoma) were chosen.

HepG2 cells were grown in T25 or T75 flasks containing 4 ml or 12 ml of growth medium respectively. The growth medium contained: 10% foetal bovine serum, 1% antibiotics (Pen Strep, 10000 units/ml Penicillin+10000 µg/ml Streptomycin, purchased from Gibco, Thermofisher), 1% non-essential amino acids and cell medium (Dulbecco's Modified Eagle Medium+GlutaMAX, purchased from Gibco, Thermofisher). Cells were incubated in an atmosphere containing 5% $CO_2$. 96-Well plates were prepared containing 0.2 ml of growth medium and 40.000 cells/well. The outer wells were filled with PBS buffer and did not contain any cells. The resulting plates are then incubated overnight. The growth medium was removed from the plate and the wells were filled with 200 µL of the appropriate treatment condition. Taking the 5 µM BEA+10 eq V1 treatment condition as an example: 20 µL from a $6.38 \cdot 10^{-3}$ M stock solution of BEA (in DMF) is added to 80 µL DMF (=solution A). From a stock solution of V1 ($1.82 \cdot 10^{-5}$ M in DMF), 50 µL is taken and added to 50 µL DMF (=solution B). Then 16.5 µL is taken from this solution and added to a mixture containing 23.5 µL of solution A and 20 µL DMF. This solution was subsequently added to 5940 µL of growth medium. The other treatment solutions were prepared in a similar fashion while making sure that the total DMF concentration always remained constant (1%).

The plates were incubated for 24 h at 37° C. and stained according to the MTT, SRB or NR staining procedure described below.

Procedure for Performing the MTT Assay

After the treatment, 100 μL of medium is removed from each well and 20 μL of the MTT solution is added (5 mg/ml in PBS buffer, 0.22 μm filter sterilized). The plate is incubated for 2 h at 37° C. The liquid is completely removed from each well and 200 μL DMSO is added. The solution is pipetted up and down in order to homogenize and the UV-VIS absorbance is measured at 570 nm using a plate reader.

Procedure for Performing the SRB Assay

After the treatment, 50 μL of a trichloroacetic acid solution (50% in milliQ water) is added, followed by storage of the plate at 4° C. for 1 h. The plate is carefully rinsed with tap water multiple times. Once dry, 200 μL SRB staining solution is added (0.4% in 1% acetic acid). After 30 min the plate is rinsed with 1% acetic acid to remove the unbound dye (3 times), followed by drying.

Then 200 μL of a 10 mM Tris buffer solution is added and each well is properly homogenized. The UV-VIS absorbance is measured at 490 nm using a plate reader.

Procedure for Performing the NR Assay

After the treatment, each well was washed once with growth medium (without antibiotics nor serum). The NR staining solution was made by adding 0.3 ml from a NR stock solution to 30 ml growth medium (without antibiotics nor serum, the stock solution was prepared by dissolving 40 mg neutral red dye in 10 ml PBS). The solution was first placed in a water bath at 37° C. for 30 min to assure solubility of the dye, followed by filtration through a 0.22 μm filter. Then, the liquid in each well was replaced by 100 μL of this staining solution and the plates were incubated at 37° C. for 3 h. The cells were washed once with PBS and dried. Subsequently, 100 μL desorption solution was added (1% HOAc, 50% EtOH and 49% $H_2O$). After 20 min, the UV-VIS absorbance is measured at 540 nm using a plate reader.

Figure 9:
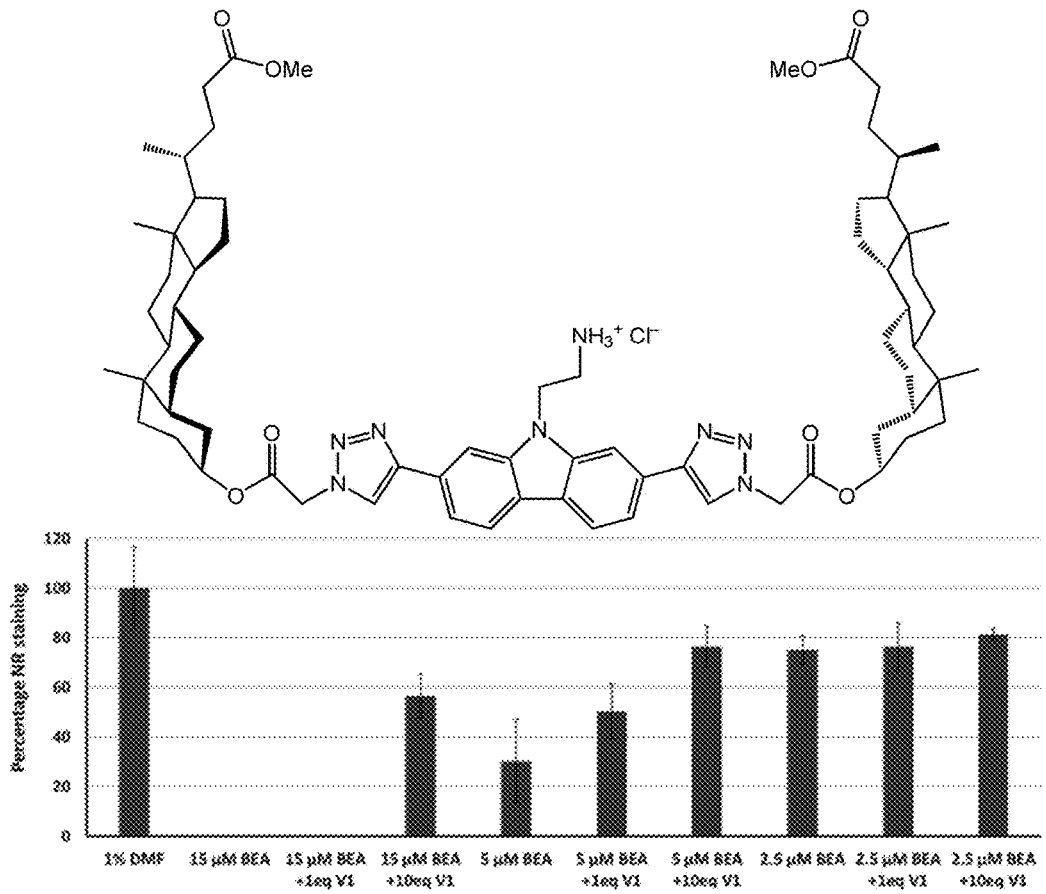
FIG. 9. Structure of receptor V1 (top) and result of the NR assay after 24 h incubation of HepG2 cells with different concentrations beauvericin in combination with receptor V1 (bottom). The error bars represent the RSD value.
Figure 10:
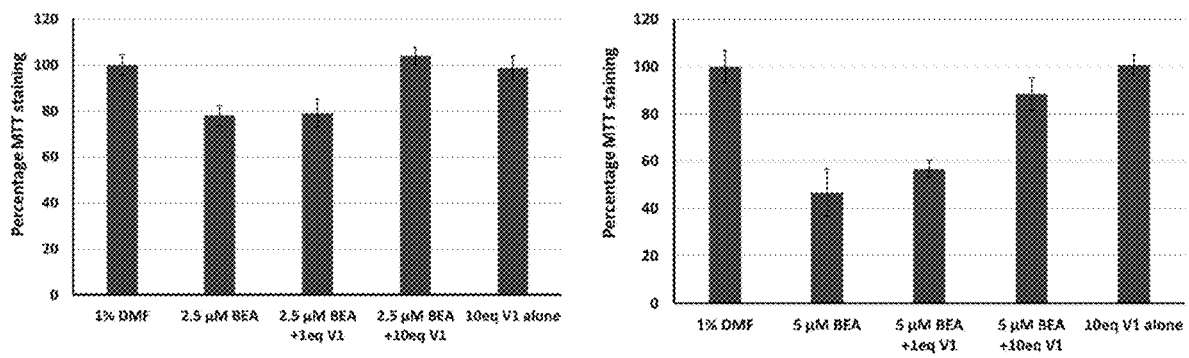
FIG. 10. Result of the MTT assays after 24 h incubation of HepG2 cells with different concentrations beauvericin in combination with receptor V1. The error bars represent the RSD value.
Figure 11:
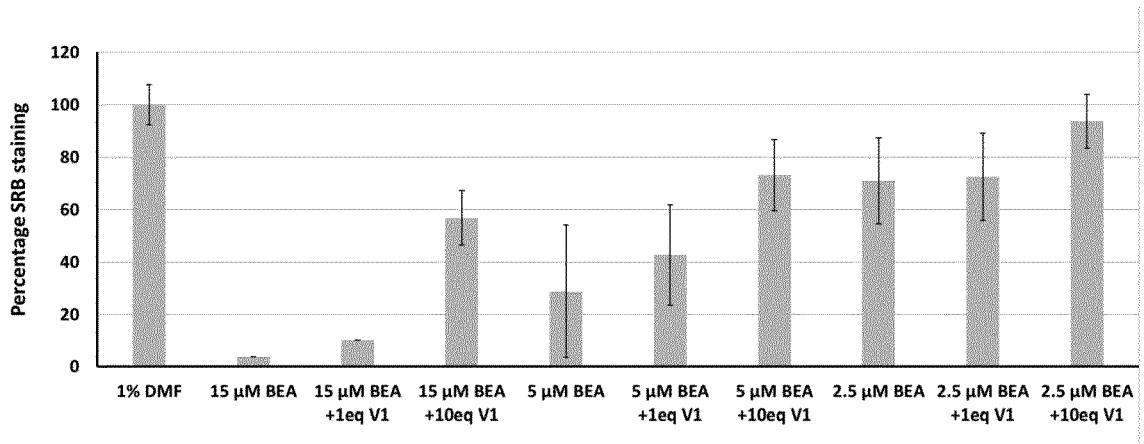
FIG. 11. Result of the SRB assay after 24 h incubation of HepG2 cells with different concentrations beauvericin in combination with receptor V1. The error bars represent the RSD value.

As shown in FIGS. 9 and 10, a mixture of 5 or 2.5 μM BEA and 10 equivalents receptor V1 was clearly less toxic compared to beauvericin alone. When only 1 equivalent V1 was used, the reduction in cytotoxicity wasn't that pronounced, which could be due to non-selective binding to serum proteins present in the growth medium.

Remarkably, while all cells that were treated with 15 μM BEA had died, in the presence of 10 equivalents V1, 60% survived (FIG. 9, bottom). A similar observation was made using the SRB assay (FIG. 11).

In a separate experiment, the toxicity of receptor V1 alone was tested in order to ascertain that the receptor itself would not cause any harm to the cells. Gratifyingly even at the highest dosage tested (200 μM) no cytotoxicity was observed as determined with the MTT, SRB and NR assay (data not shown). These results demonstrate the possible use of receptor V1 to reduce beauvericin-induced cytotoxicity.

Example 9

As already mentioned, receptor V1 is unable to bind larger ionophoric toxins such as cereulide (CER) or valinomycin (VAL). Based on previous observations, we reasoned that the length of the linker connecting the ammonium group with the carbazole moiety was one of the major drivers behind this selectivity. In order to assess if a receptor containing a longer linker would be able to bind CER (or VAL), receptor V2 was synthesized (Scheme 11).

Scheme 11. Synthesis of receptor V2 (for the synthesis of the steroid fragment we refer to scheme 2).

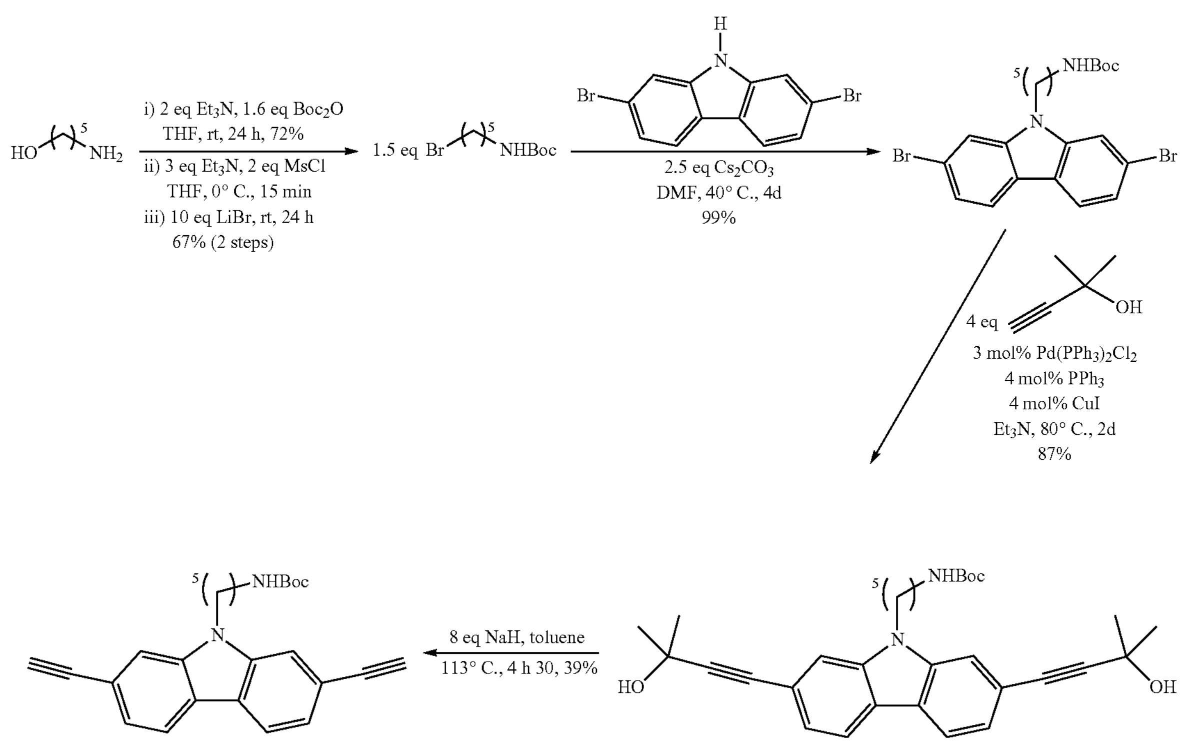

-continued
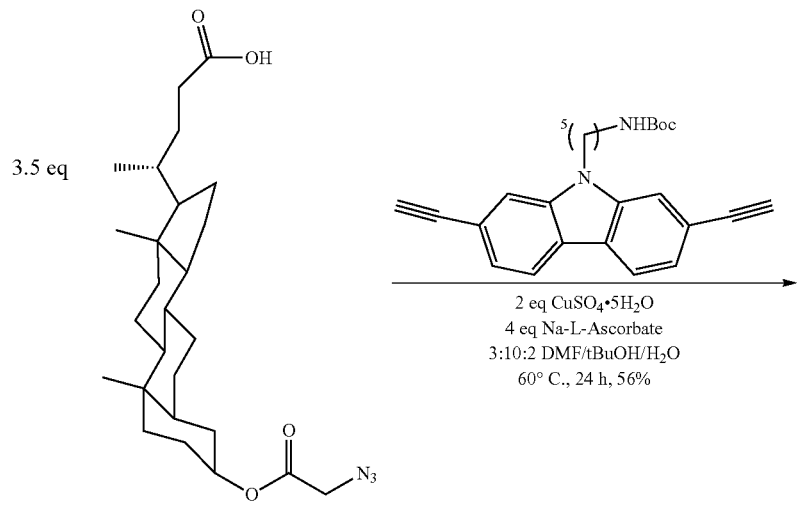
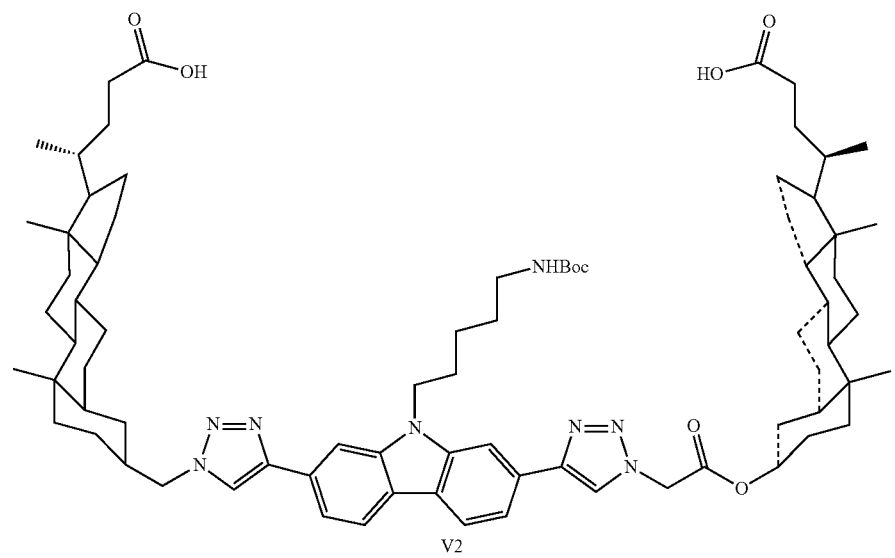
V2

Receptor V2 was subsequently immobilized onto 3-aminopropyl functionalized silica resin (Scheme 12).

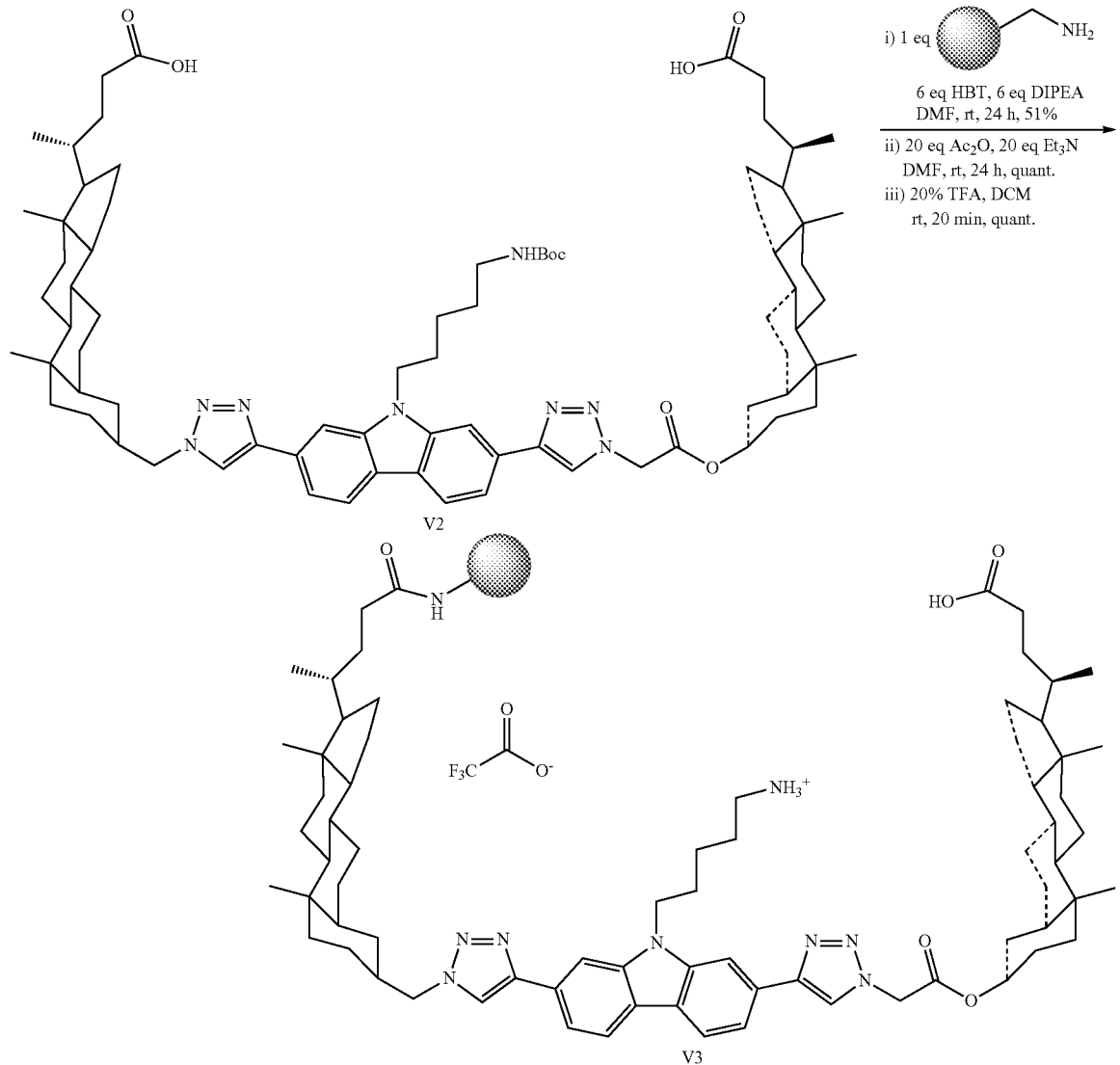

Scheme 12. Immobilization of receptor V2.

The obtained immobilized receptor (V3) was subsequently tested for its affinity towards VAL (which is a model compound for CER). To this end, a 100 nM valinomycin solution in hexane was added to the resin followed by shaking overnight. After elution of the residual solvent (=Rest), a gradient elution was performed and the valinomycin content in each fraction was determined using LC-MS/MS. As a control, the same protocol was applied to a resin containing an analogous receptor having a shorter carbon spacer between the ammonium group and the carbazole moiety (FIG. 12, receptor V4).

Figure 12:
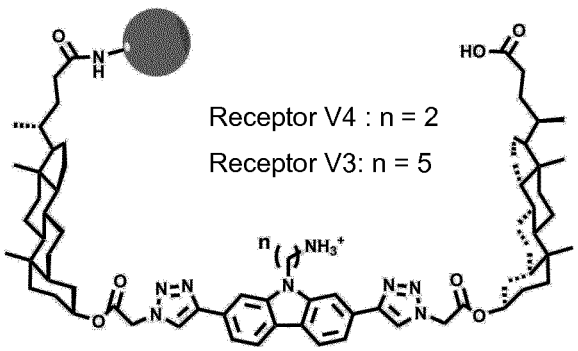
FIG. 12. Structure of receptor V3 and V4(top). Results from the SPE experiment (bottom). The area under the curve of the most abundant VAL fragment ion (LC-MS/MS) in each collected fraction is shown on the vertical axis.
Figure 12:
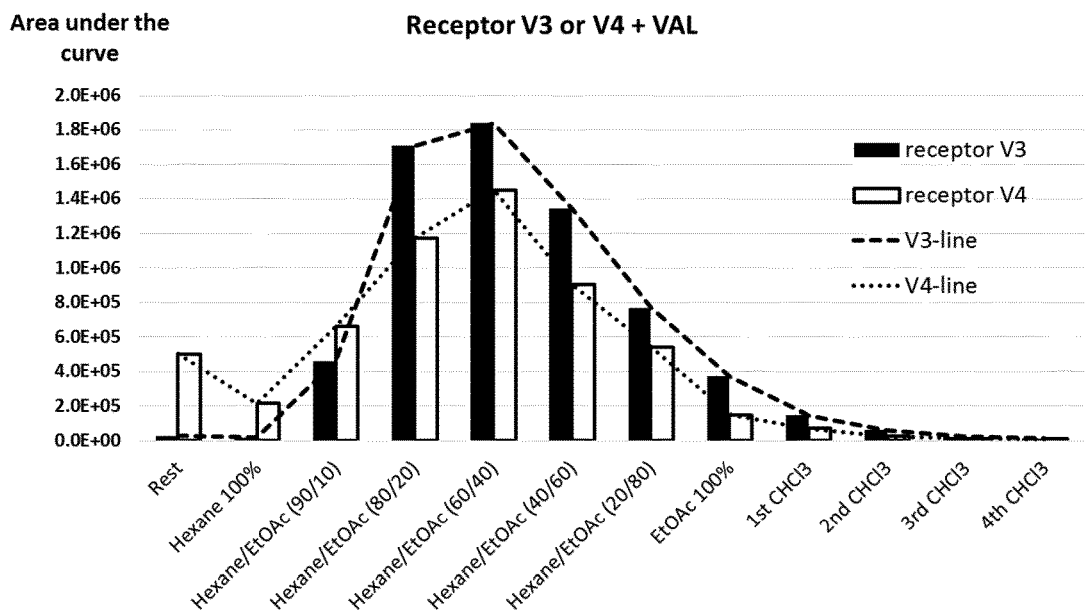

From the data it becomes apparent that both V3 and V4 behave quite similarly (FIG. 12). The major difference lies in the fact that with the shorter linker (receptor V4), not all of the toxin absorbs onto the resin as evidenced by its presence in the Rest- and 100% hexane fraction. For the longer linker (receptor V3) on the other hand, no toxin is detected in these fractions, which indicates complete absorption onto the resin. As such, the longer linker seems to provide better retention capabilities towards valinomycin, compared to its shorter counterpart.

Example 10

So far for synthesis of the receptors, the connection between the carbazole moiety and the hydrophobic side-arms has always been achieved using the CuAAC reaction. Next to this approach, we decided to explore the SN2 reaction to couple both moieties to each other. At the same time we assessed the possibility of using pyrene as side-arm, which acts both as a hydrophobic moiety and fluorescent label. As shown in Scheme 13, this route required the synthesis of an alternative carbazole fragment, modified with propargyl bromide substituents. Subsequent $S_N2$ reaction with 1-amino-pyrene followed by Boc-deprotection, yielded the envisioned pyrene-labeled receptor V5 (Scheme 14).

Scheme 13. Synthesis of propargyl bromide substituted carbazole

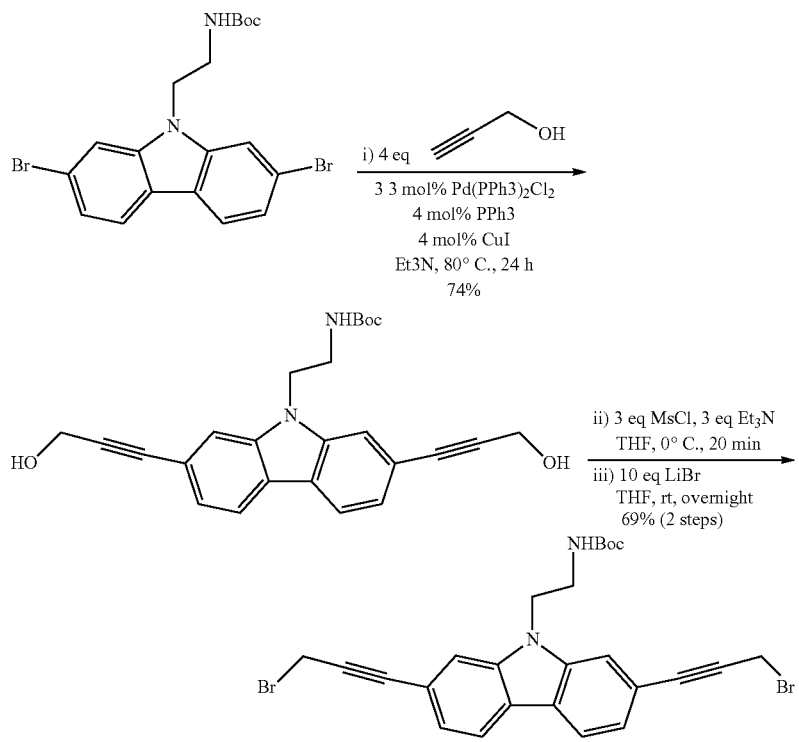

Scheme 14. Synthesis of pyrene-labeled receptor V5.

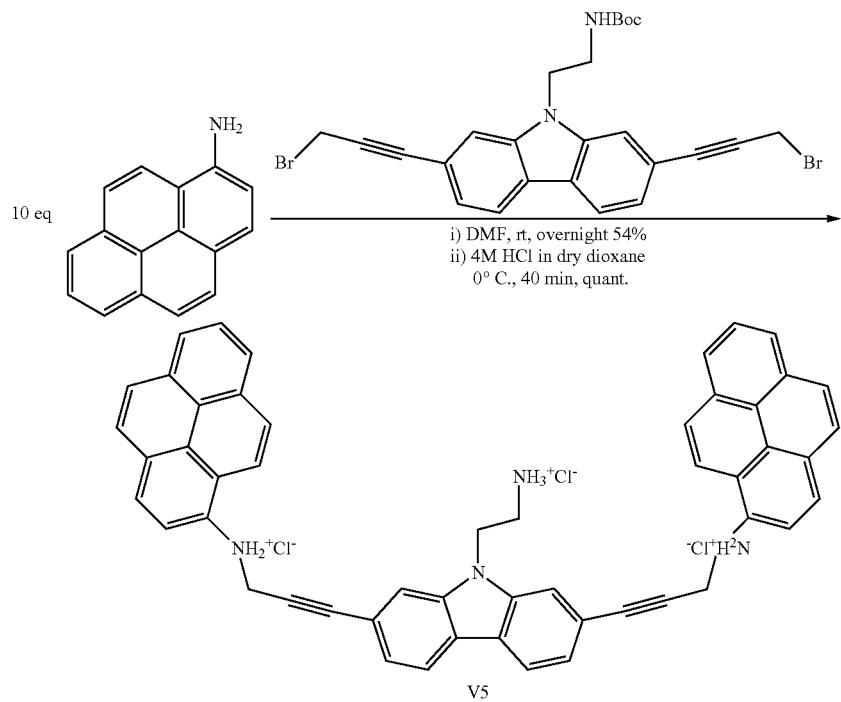

Figure 13:
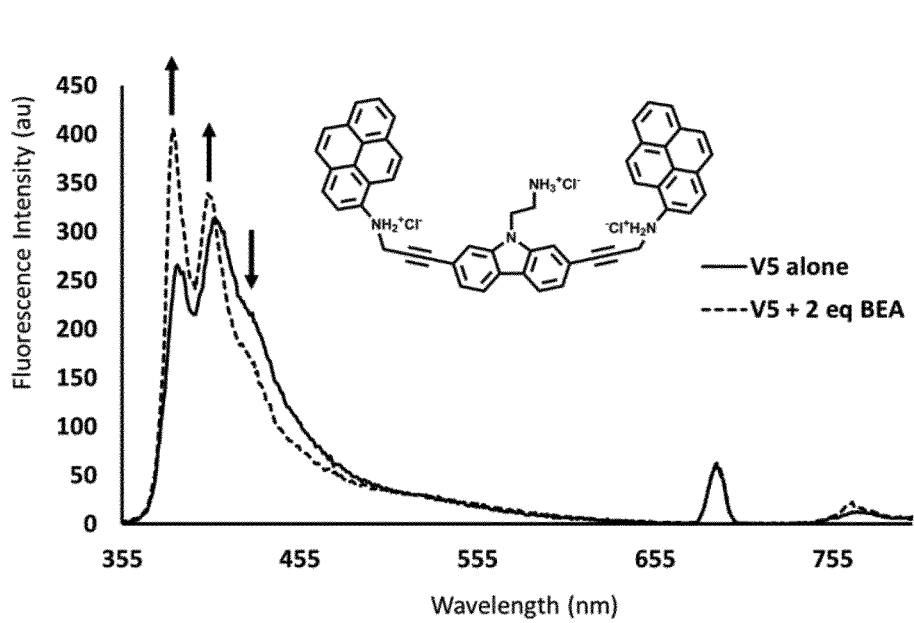
FIG. 13. Fluorescence emission of 10 μM receptor V5 in $CHCl_3$ before (full line) and after addition of 2 eq BEA (dotted line) using $\lambda_{ex}=344$ nm.

Receptor V5 was then tested for affinity towards beauvericin using fluorescence titration as described before (FIG. 13). Gratifyingly, addition of 2 equivalents beauvericin to 10 μM receptor V5 in CHCl$_3$ resulted in an increase in fluorescence intensity, which indicates the occurrence of binding interactions. The pyrene label could potentially increase the sensitivity of beauvericin detection compared to a receptor containing solely carbazole as fluorophore.

Moreover, this label might allow the localization of the receptor in cell culture using confocal microscopy.

Example 11

Although promising results have been obtained in $CHCl_3$, certain applications require water soluble receptors. In a first attempt to synthesize such derivatives, receptor V6 (Scheme 15) was prepared which contains two sulphate substituents. The negative charges on the sulphates in combination with the positive charge on the ammonium functionality, should help to increase the water solubility. Sadly, these modifications were not sufficient to achieve this goal and although receptor V6 was soluble in a MeOH/THF mixture, it didn't solubilize in $H_2O$.

Example 12

In a second attempt to develop water soluble receptors, we decided to employ polyethylene glycol (PEG) or polyoxazoline (PDX). These polymers are known to be water soluble and due to their biocompatibility (low immunogenicity) they are the perfect candidates for receptor derivatization. Knowing that conjugation of a 5 kDa PEG-chain to cholesterol results in a water soluble product, we synthesized a receptor with a 5 kDa PEG-chain attached to each steroid side-arm. As shown in Scheme 16, synthesis of such analogue started with the formation of N-hydroxy-succinimide derivative V7 followed by reaction with commercially available PEG-chain V8 (average MW=5000 Da). After dialysis (using a 8-10 kDa membrane) and Boc-deprotection using 4M HCl in dioxane, receptor V10 could be obtained (note: partial degradation of the PEG-chain was observed on NMR).

Scheme 15. Synthesis of receptor V6 (for the synthesis of the starting material we refer to Scheme 1).

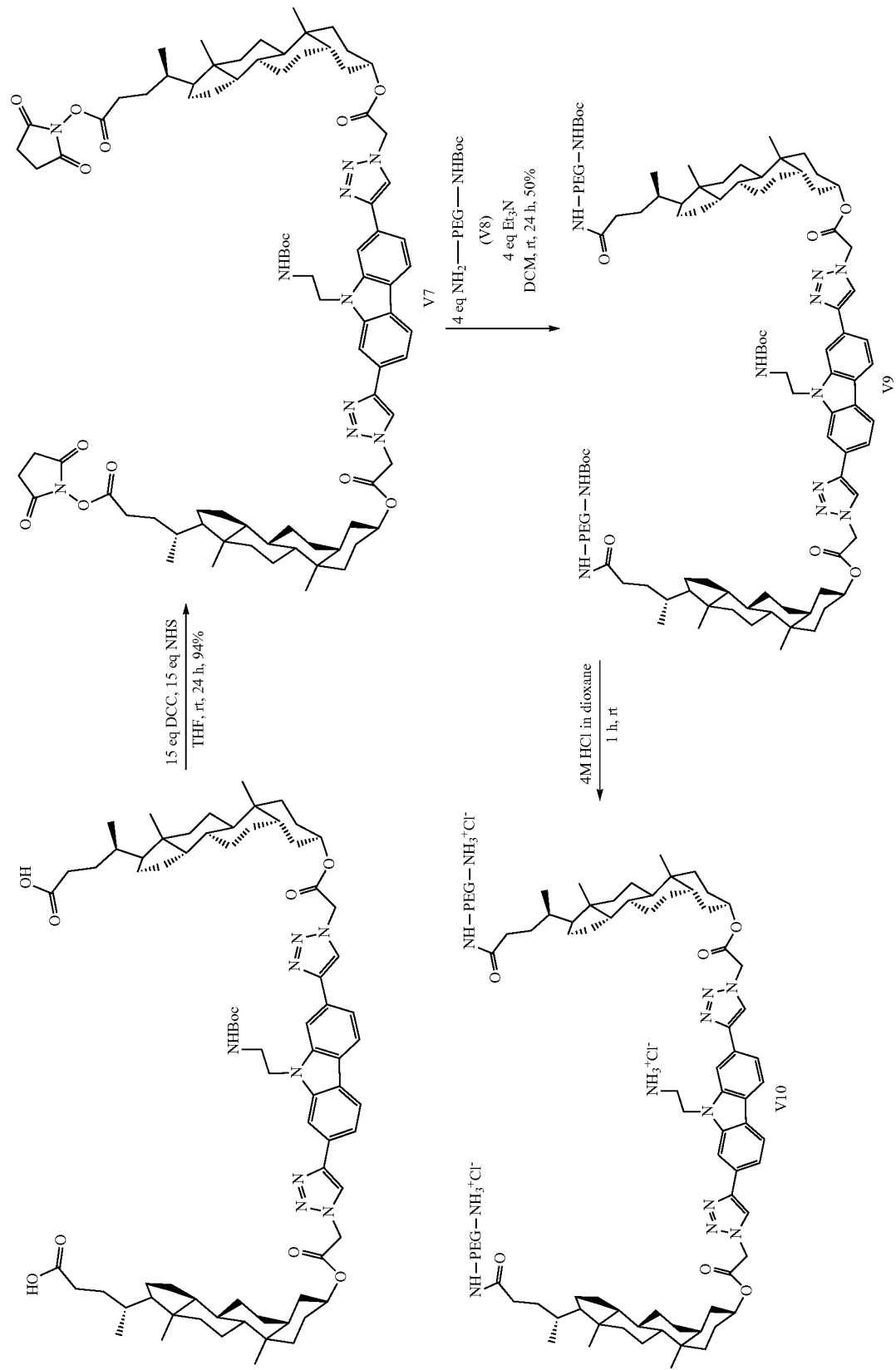
Scheme 16. Synthesis of pegylated receptor V10 (for the synthesis of the starting material we refer to Scheme 2).

Initial attempts at using the same synthetic route for the polyethyloxazoline derivative failed. Therefore, an alternative protocol was employed in which the polymer was first synthesized using standard procedures and 1-(bromomethyl) pyrene as the initiator. Termination of the polymer (average MW=5 kDa) with the dicarboxylic acid receptor (Scheme 17) yielded the desired polyethyloxazoline-modified receptor. DOSY NMR indicated the presence of only one species. Final Boc-deprotection with 4M HCl in dioxane gave receptor V11.

Gratifyingly, both PEG- and POX-receptors (V10 and V11 respectively) were soluble in $H_2O$. Hence, PEG and POX polymers are effective modifications to increase the water solubility of a poorly soluble compound. As a final remark, it is worth mentioning that N-hydroxy-succinimide derivative V7 (Scheme 16) can be further derivatized using a wide variety of amines. For example, one can easily conceptualize the further chemical modification of V7 with peptides.

Scheme 17. Synthesis of polyethyloxazoline receptor V11.

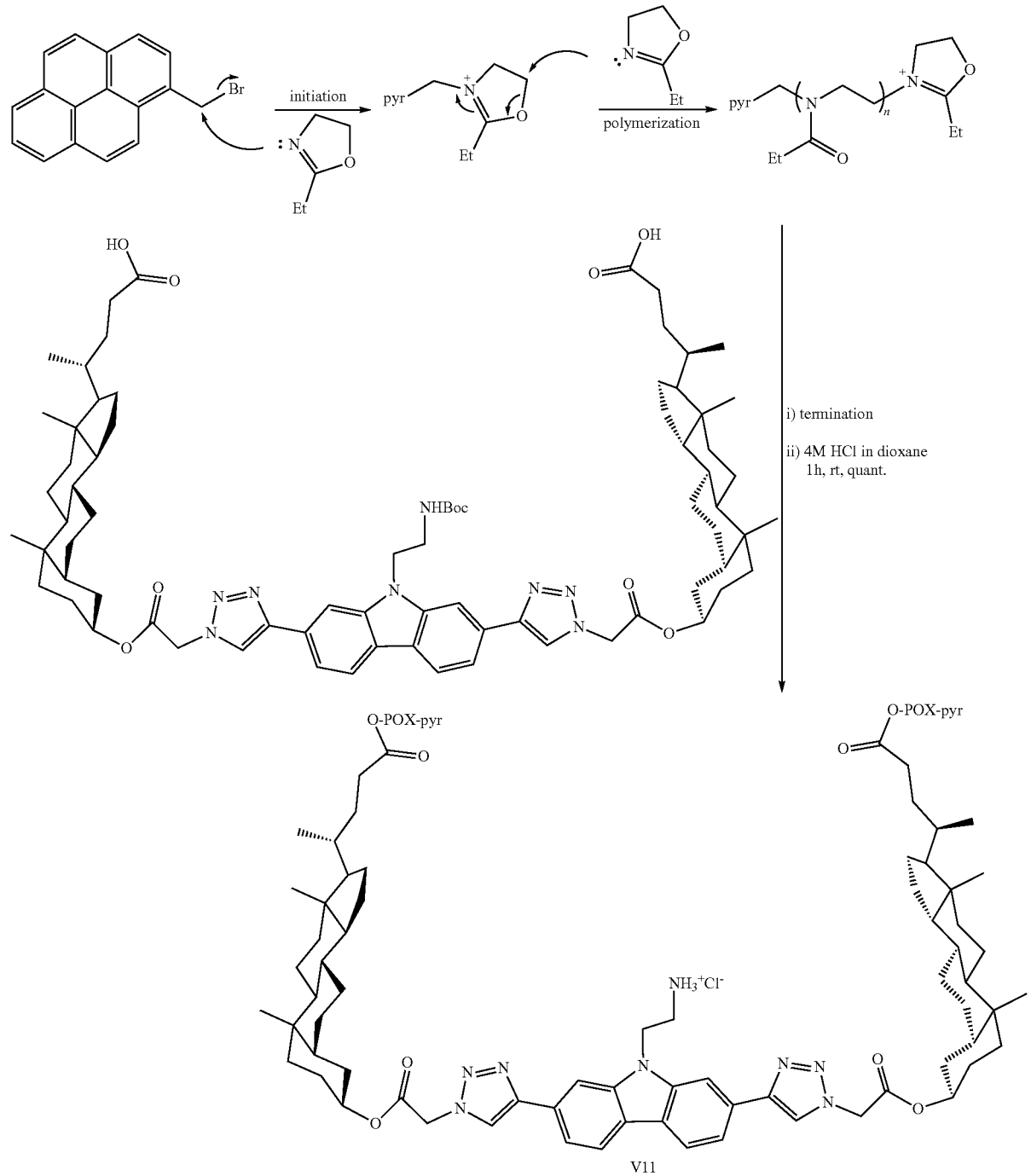

Example 13

We previously mentioned the synthesis of a receptor containing cyclic disulfides (Scheme 10) for immobilization onto gold nanoparticles (or surfaces). In a continuation of that work, we explored the possibility of modifying the receptor with thiol functionalities. As shown in Scheme 18, the synthesis of such derivative started with the formation of cysteine analogue V12, followed by amide bond formation with previously reported dicarboxylic acid receptor.

Next to its possible immobilization onto (gold) surfaces, the thiol handles of receptor V13 (after -StBu deprotection) could be used for further derivatization using well-known thiol conjugation methodologies (e.g. maleimide chemistry).

REFERENCES

Bernard, J.; Wennemers, H. . *Lett.* 2007, 9, 4283-4286.
Chang, K.-H.; Liao, J.-H.; Chen, C.-T.; Mehta, B. K.; Chou, P.-T.; Fang, J.-M. *J. Org. Chem.* 2005, 70, 2026-2032.

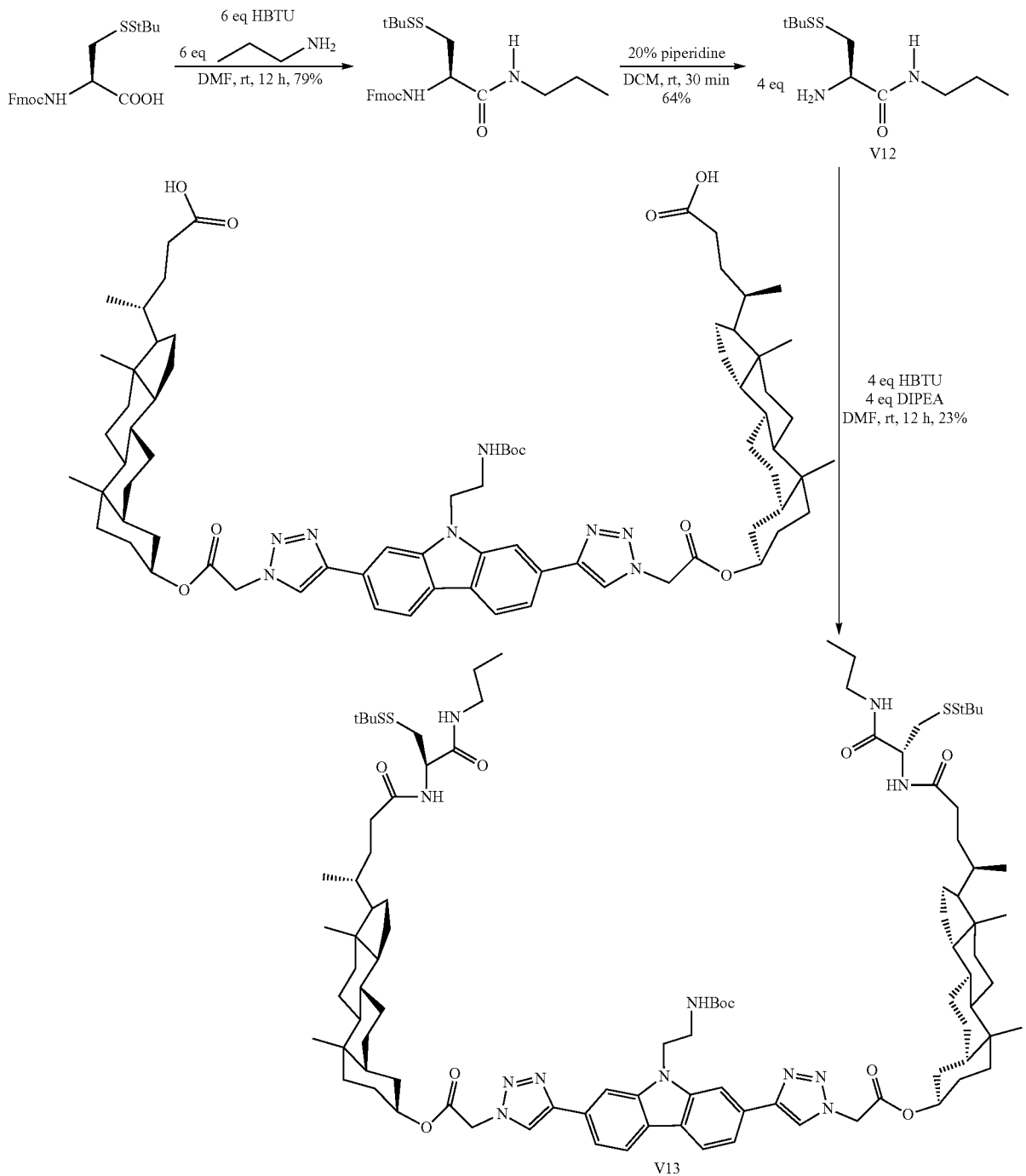

Scheme 18. Synthesis of a receptor containing thiol functionalities.

Gefen, T.; Vaya, J.; Khatib, S.; Rapoport, I.; Lupo, M.; Barnea, E.; Admon, A.; Dan Heller, E.; Aizenshtein, E.; Pitcovski, J. *Immunology* 2014, 144, 116-126.

Henley, P. D.; Waymark, C. P.; Gillies, I.; Kilburn, J. D. *J. Chem. Soc. Perkin Trans.* 1, 2000, 1021-1031.

Maragos, C. M. *World Mycotoxin J.* 2009, 2, 221-238.

O'Kennedy, R.; Byrne, M.; O'Fagain, C.; Berns, G. *Biochem. Educ.* 1990, 18, 136-140.

Santini, A.; Ferracane, R.; Meca, G.; Ritieni, A. *Anal. Bioanal. Chem.* 2009, 395, 1253-1260.

Tonshin, A. A.; Teplova, V. V.; Andersson, M. A.; Salkinoja-Salonen, M. S. *Toxicology* 2010, 276, 49-57.

The invention claimed is:

1. A compound of formula (I):

where:

$L_1$ and $L_2$ are each independently linker moieties chosen from $H_1$ and $H_2$ are each independently chosen from steroids, abietic acid derivatives, naphthalene, pyrene, acenaphthylene, or anthracene;

X is chosen from —CR'R"—, —NR'—, and —O—;

R' and R" are each independently chosen from —H and optionally substituted alkyl;

n is 0 or 1; and at least one of the $L_1$, $H_1$, $L_2$, $H_2$, and moieties is substituted
with an amine-containing moiety chosen from —$NH_3^+$ or —NHY, where Y is a protecting group chosen from Boc, Fmoc, Cbz, Bn, or Trt,
wherein the compound of formula (I) forms a cavity for accommodating an ionophoric compound.

2. The compound of claim 1, wherein
the $L_1$ and $L_2$ moieties are attached to the moiety according to any of representations A, B, C, or D:

A

B

-continued

C

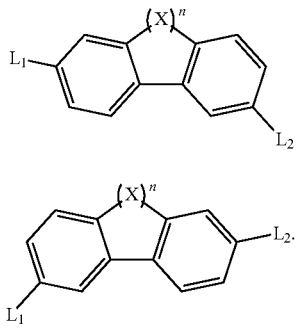

D

3. The compound of claim 1, wherein the amine-containing moiety
is attached to the $H_1$, $H_2$, $L_1$, $L_2$, R', or

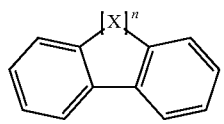

moiety through an alkyl linker
optionally substituted with one or more substituents chosen from hydroxyl groups, carboxyl groups, carbonyl groups, thiol groups, sulfide groups, sulfonyl groups, amides, amines, epoxides, aldehydes, cyano groups, nitrile groups, aminocarbonyl groups, aminocarboxyl groups, alkene, alkyne, phenyl, and heterocycles.

4. The compound of claim 1, wherein X is —NR'—, and the compound is of formula (II):

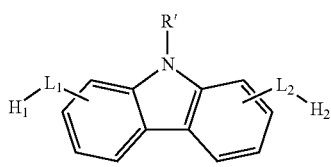

(II)

where:
$L_1$ and $L_2$ are each independently linker moieties chosen from

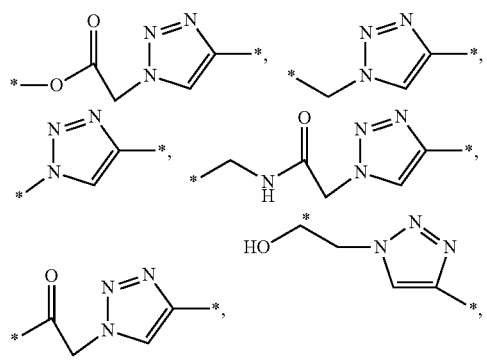

-continued

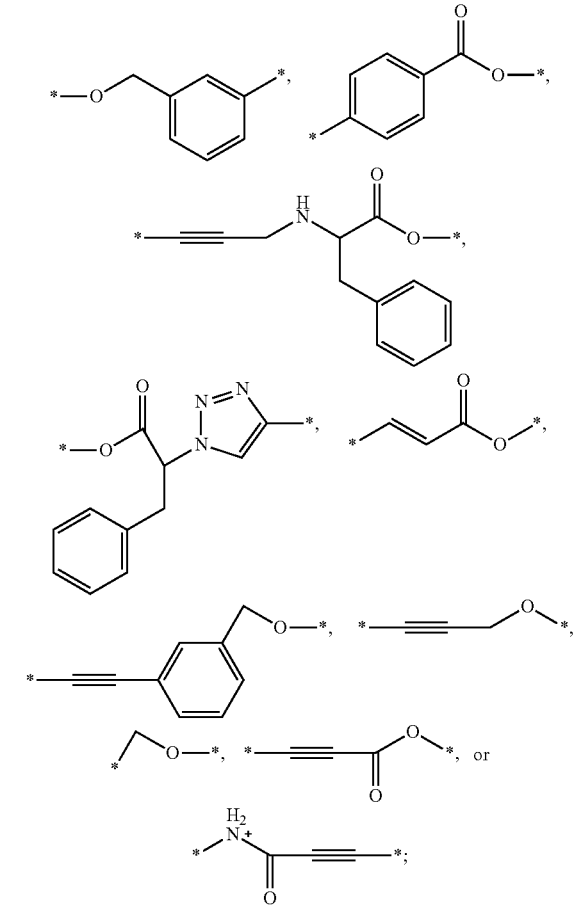

$H_1$ and $H_2$ are each independently hydrophobic cyclic moieties chosen from steroids, abietic acid derivatives, naphthalene, pyrene, acenaphthylene, or anthracene;
R' is optionally substituted alkyl; and
at least one of the $L_1$, $H_1$, $L_2$, $H_2$, and R' moieties is substituted with an amine-containing moiety chosen from —$NH_3^+$ or —NHY, where Y is a protecting group chosen from Boc, Fmoc, Cbz, Bn, or Tr,
wherein the compound of formula (II) forms a cavity for accommodating an ionophoric compound.

5. The compound of claim 4, wherein the amine-containing moiety
is attached to the $H_1$, $H_2$, $L_1$, $L_2$, R', or

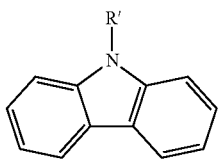

moiety through an alkyl linker
optionally substituted with one or more substituents chosen from hydroxyl groups, carboxyl groups, carbonyl groups, thiol groups, sulfide groups, sulfonyl groups, amides, amines, epoxides, aldehydes, cyano groups, nitrile groups, aminocarbonyl groups, aminocarboxyl groups, alkene, alkyne, phenyl, and heterocycles.

6. The compound of claim 1, wherein X is —NR'—, and the compound is of formula (III):

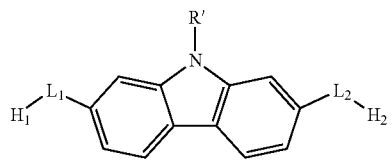

where:

$L_1$ and $L_2$ are each independently linker moieties chosen from

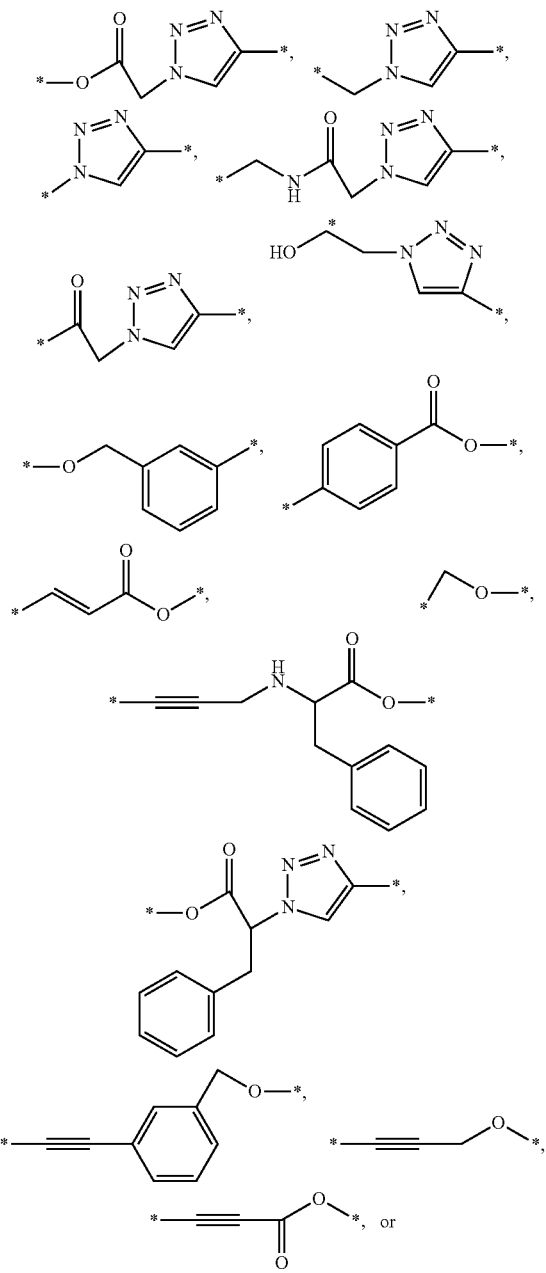

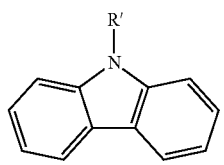

$H_1$ and $H_2$ are each independently hydrophobic cyclic moieties chosen from steroids, abietic acid derivatives, naphthalene, pyrene, acenaphthylene, and anthracene;

R' is optionally substituted alkyl; and at least one of the $L_1$, $H_1$, $L_2$, $H_2$, and R' moieties is substituted with an amine-containing moiety chosen from; —$NH_3^+$ or —NHY, where Y is a protecting group chosen from Boc, Fmoc, Cbz, Bn, or Tr, wherein the compound of formula (III) forms a cavity for accommodating an ionophoric compound.

7. The compound of claim 6, wherein the amine-containing moiety is attached to the $H_1$, $H_2$, $L_1$, $L_2$, R', or

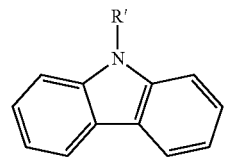

moiety through an alkyl linker optionally substituted with one or more substituents chosen from hydroxyl groups, carboxyl groups, carbonyl groups, thiol groups, sulfide groups, sulfonyl groups, amides, amines, epoxides, aldehydes, cyano groups, nitrile groups, aminocarbonyl groups, aminocarboxyl groups, alkene, alkyne, phenyl, and heterocycles.

8. The compound of of claim 1 and having formula (Ma):

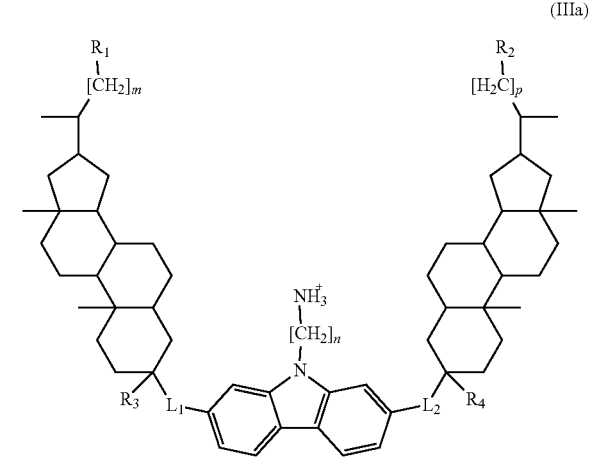

where:
R₁ and R₂ are each independently chosen from —(C=O)-O—R₅, —(C=O)—NH—R₅, or —(C=O)-OH, where each R₅ is a —C₁₋₆ alkyl that is optionally substituted with one or more of —OH, —halo, —biotin, —disulfide, or a detectable label;
R₃ and R₄ are each independently chosen from —H or —OH;
L₁ and L₂ are each independently chosen from

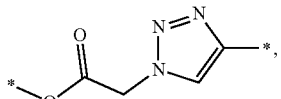

-continued

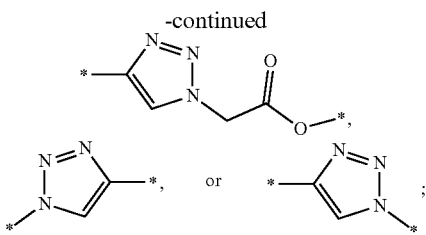

and m, n, and p are each independently an integer from 1 to 10.

9. The compound of claim 1, selected from the group consisting of compounds 1 to 25:

(Compound 1)

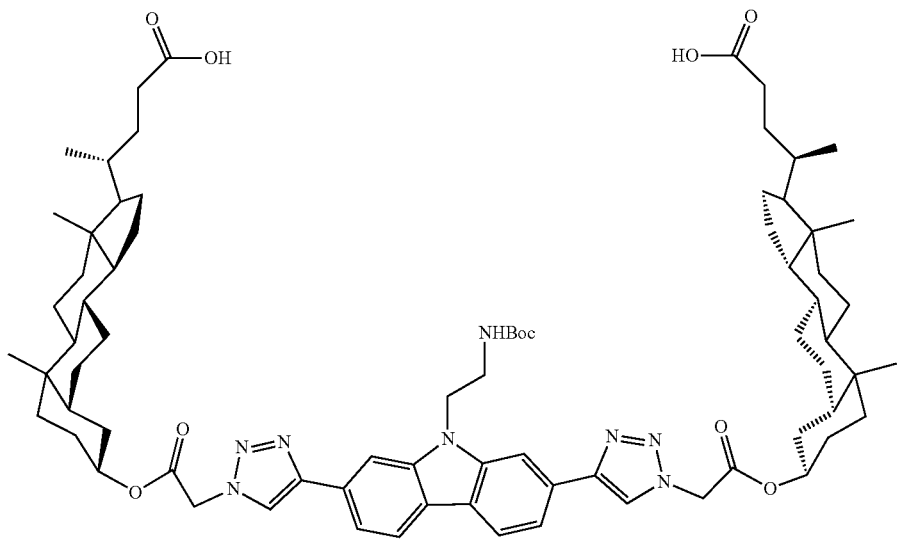

(Compound 2)

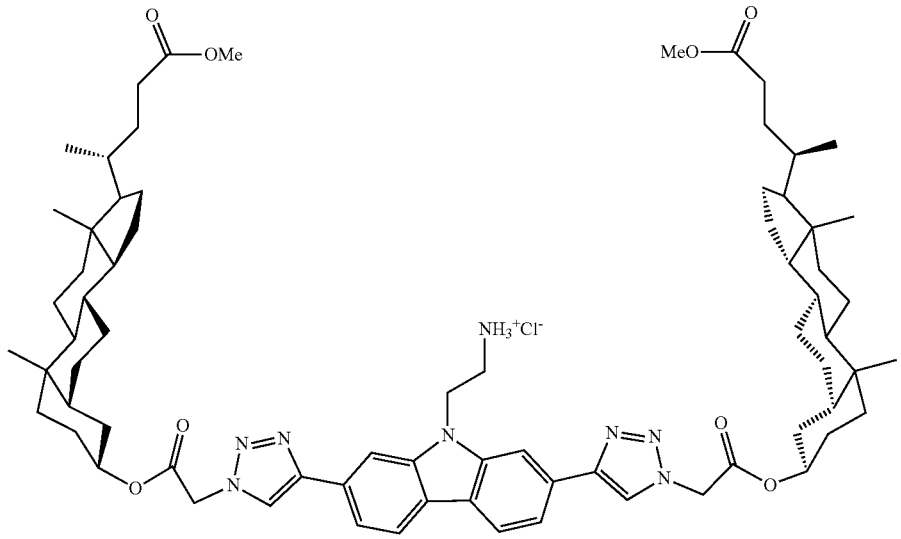

-continued
(Compound 3)
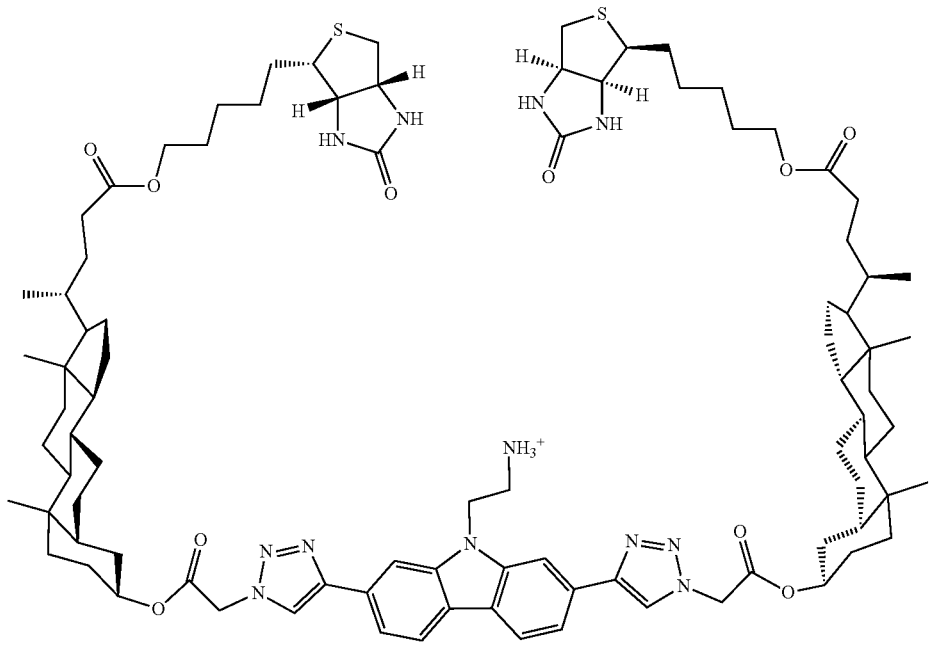
(Compound 4)
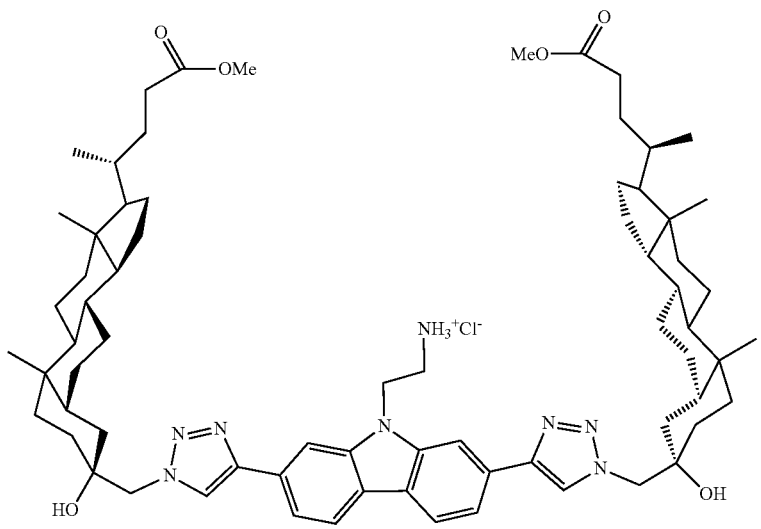

(Compound 5)
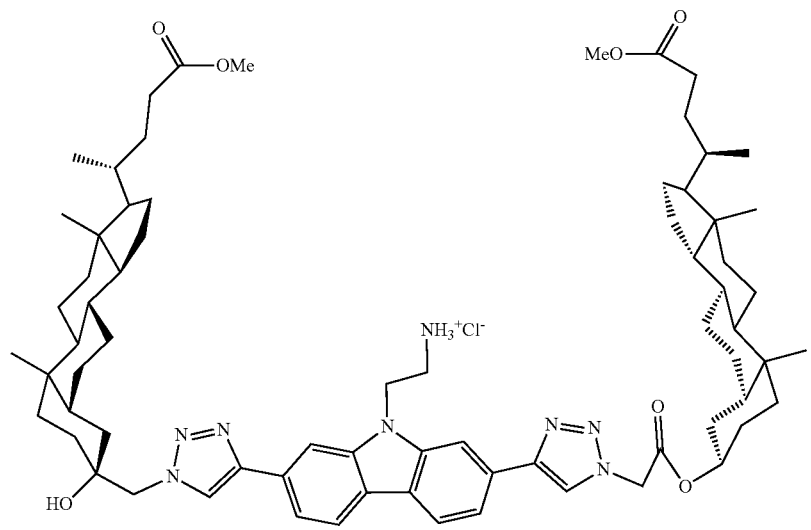
(Compound 6)
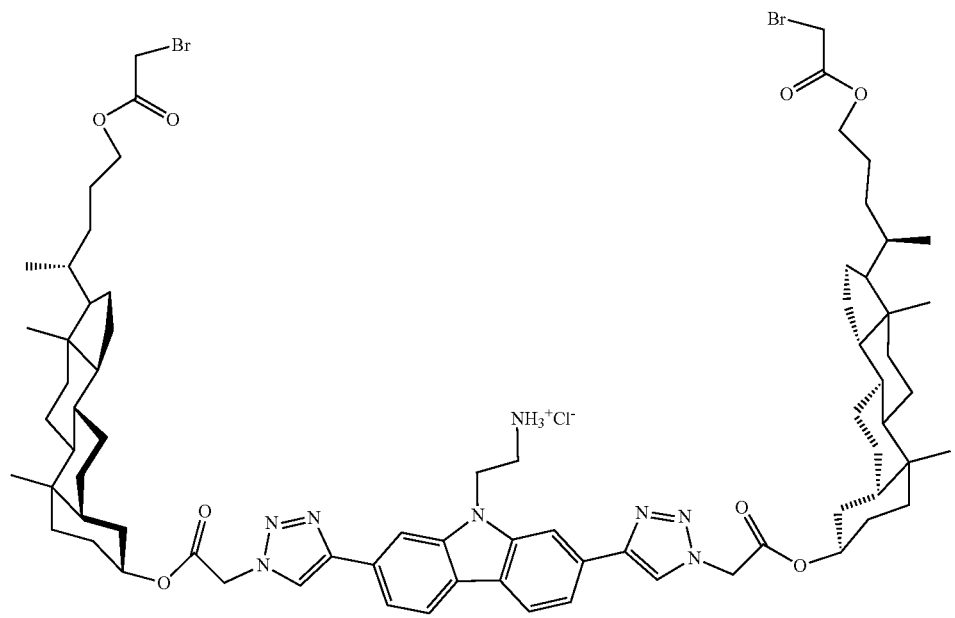

(Compound 7)
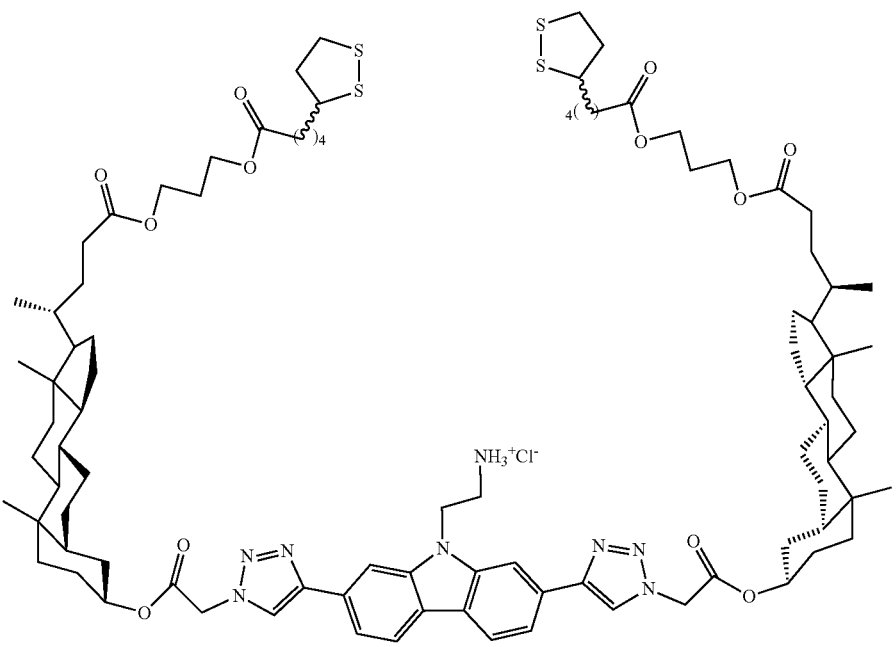
(Compound 8)
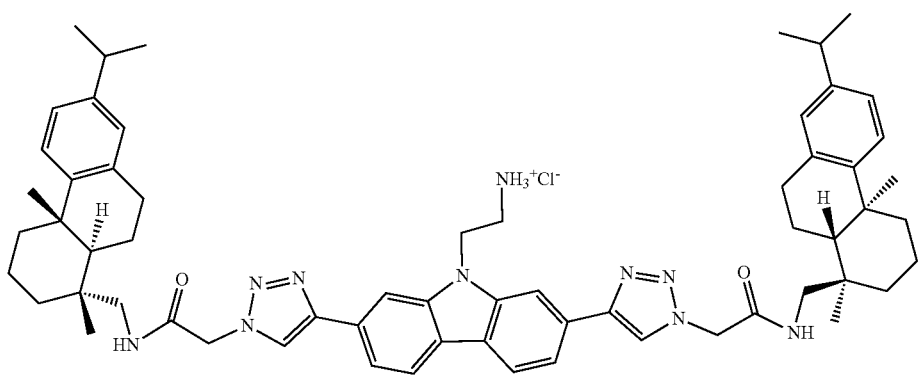
(Compound 9)
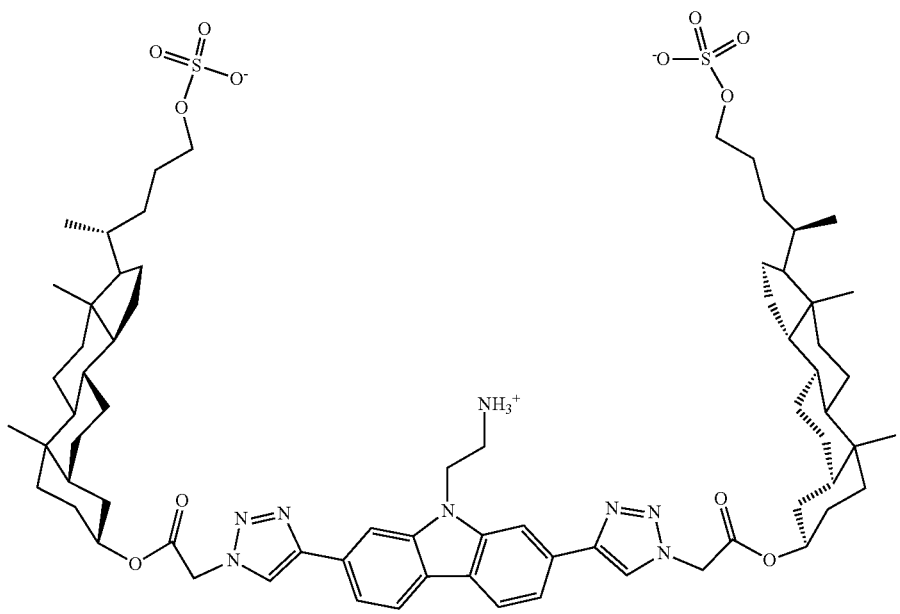

(Compound 10)
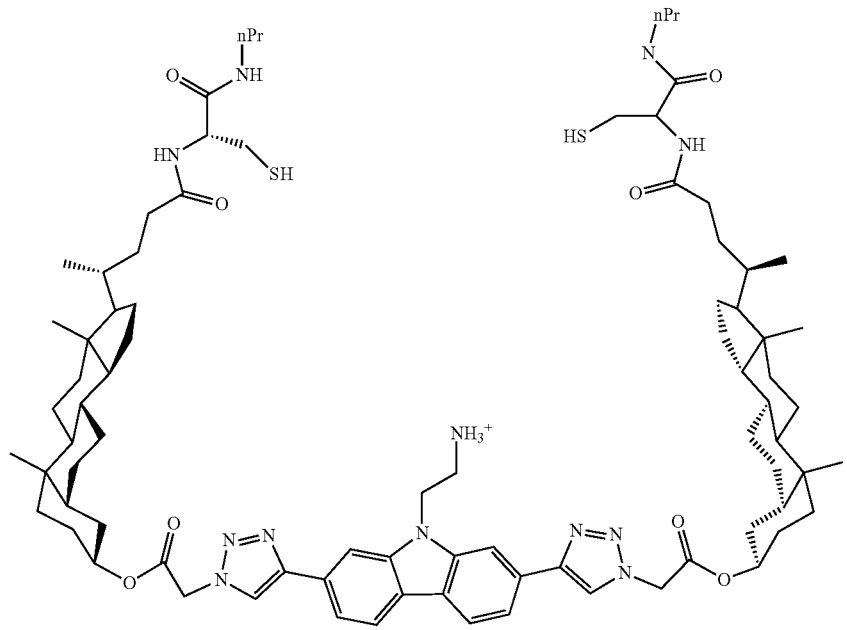
(Compound 11)
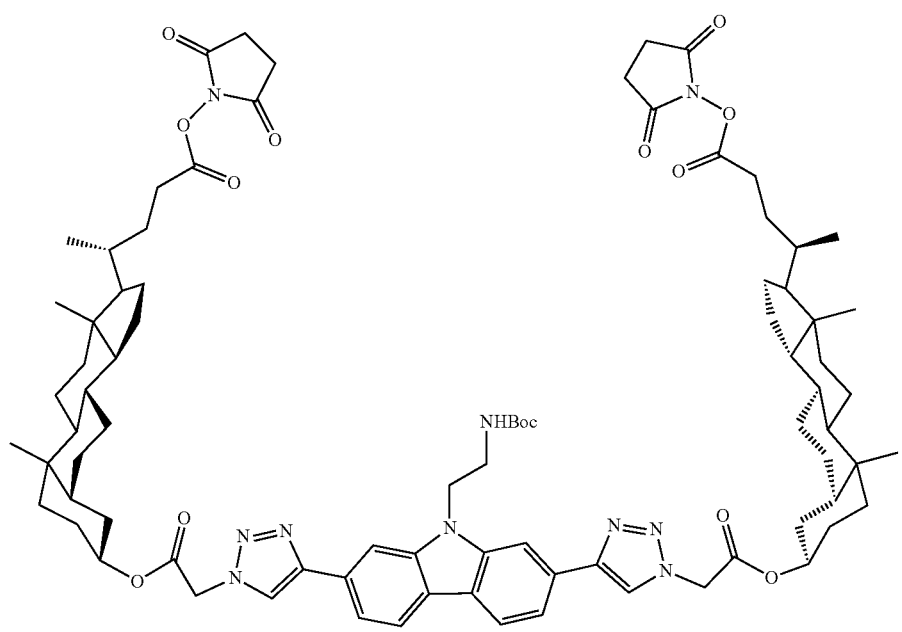

-continued
(Compound 12)
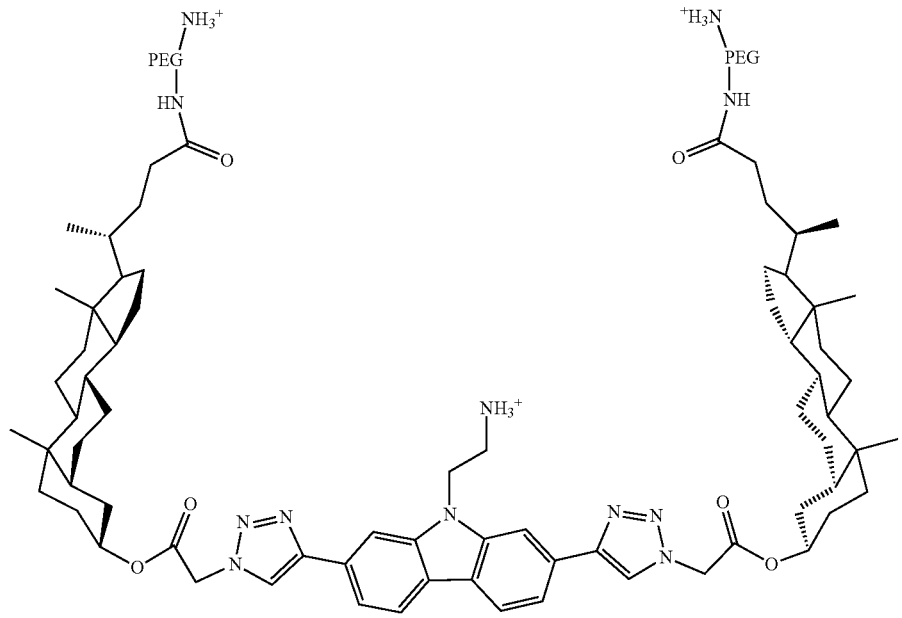
(Compound 13)
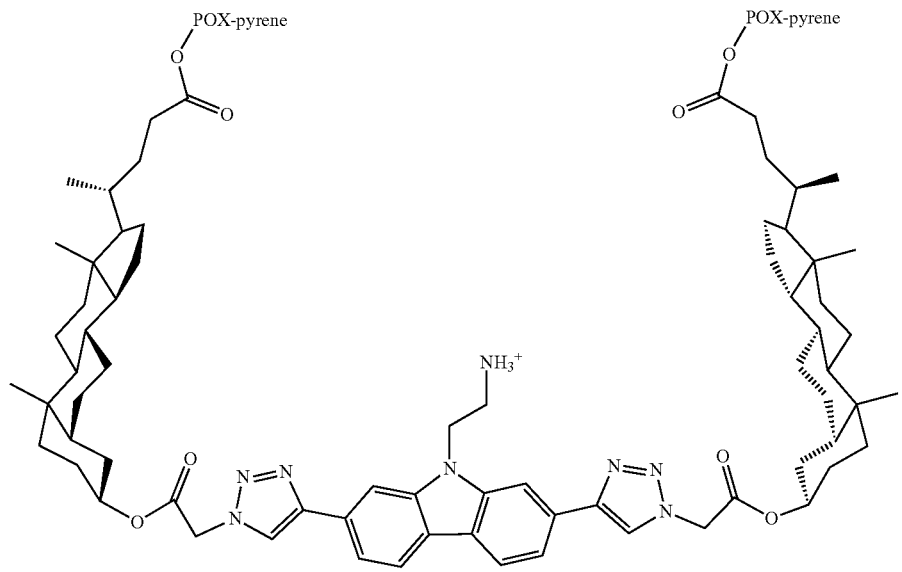

-continued
(Compound 14)
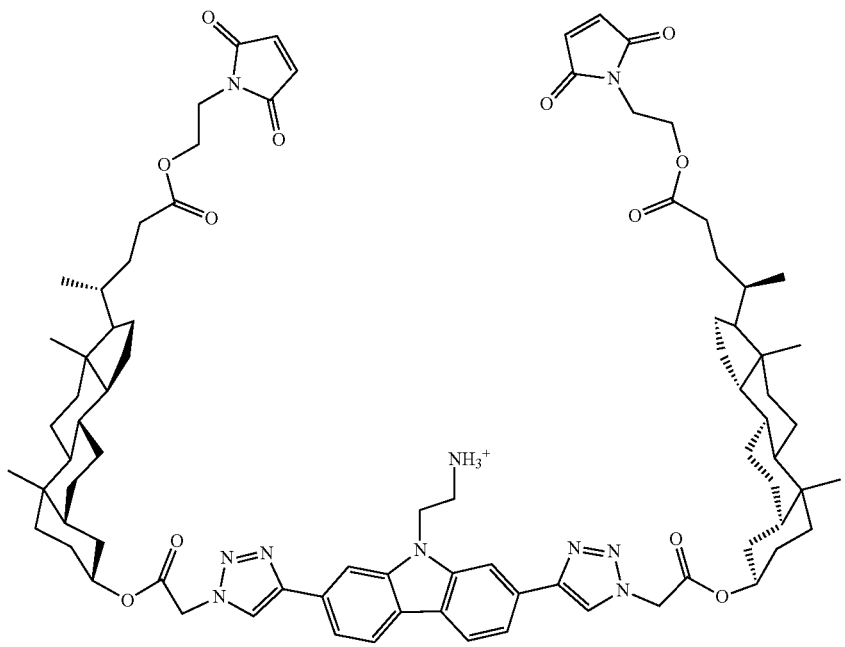
(Compound 15)
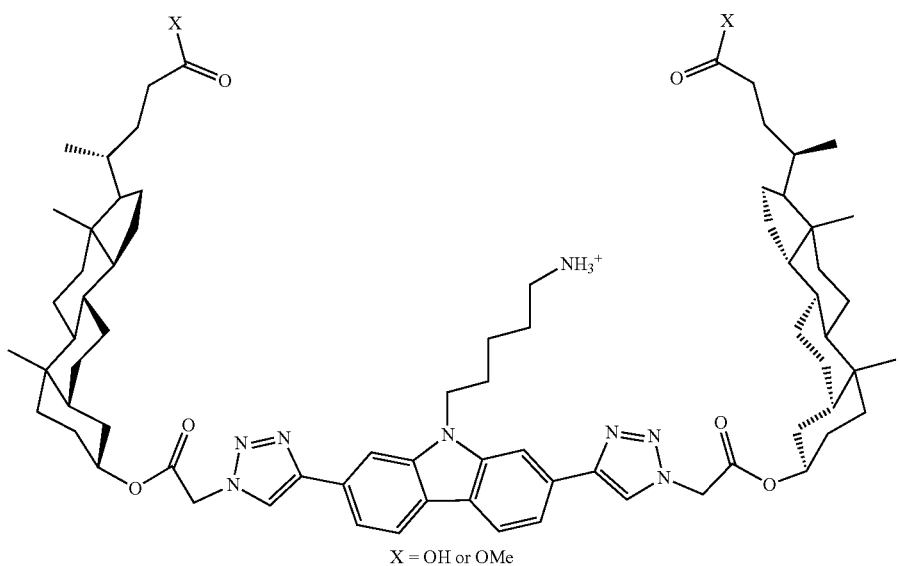
X = OH or OMe
(Compound 16)
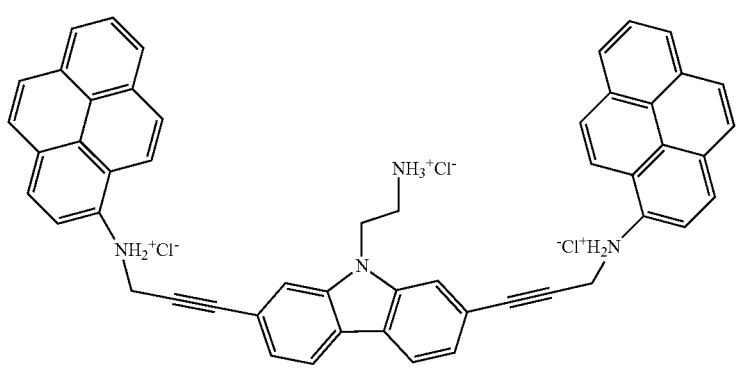

(Compound 17)
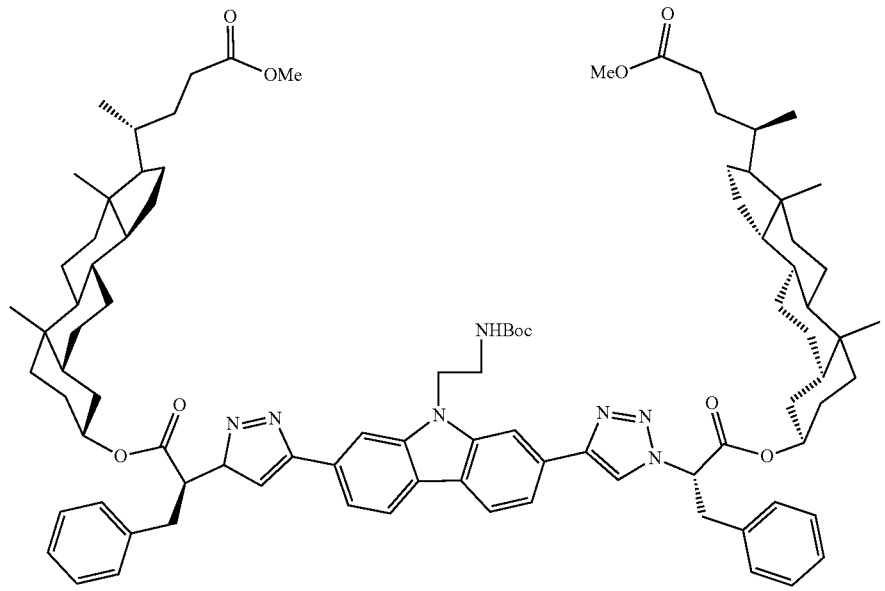
X5
(Compound 18)
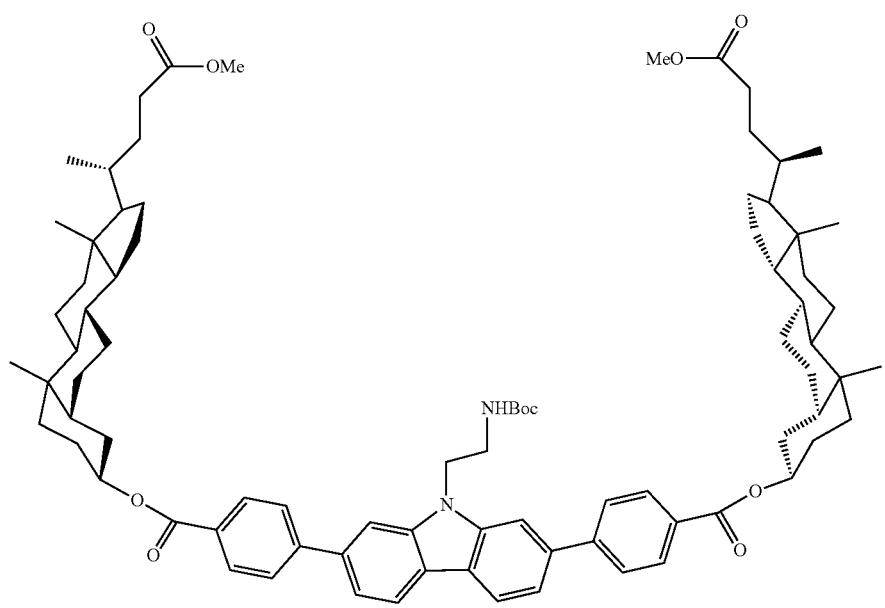
X7

-continued
(Compound 19)
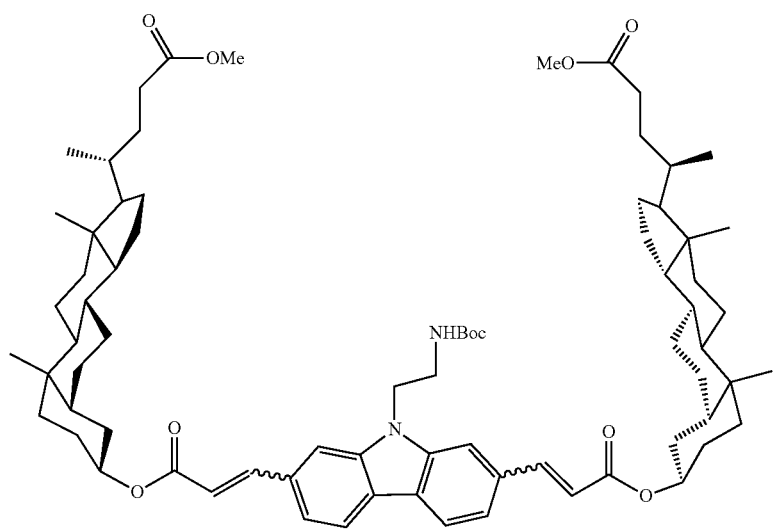
X10
(Compound 20)
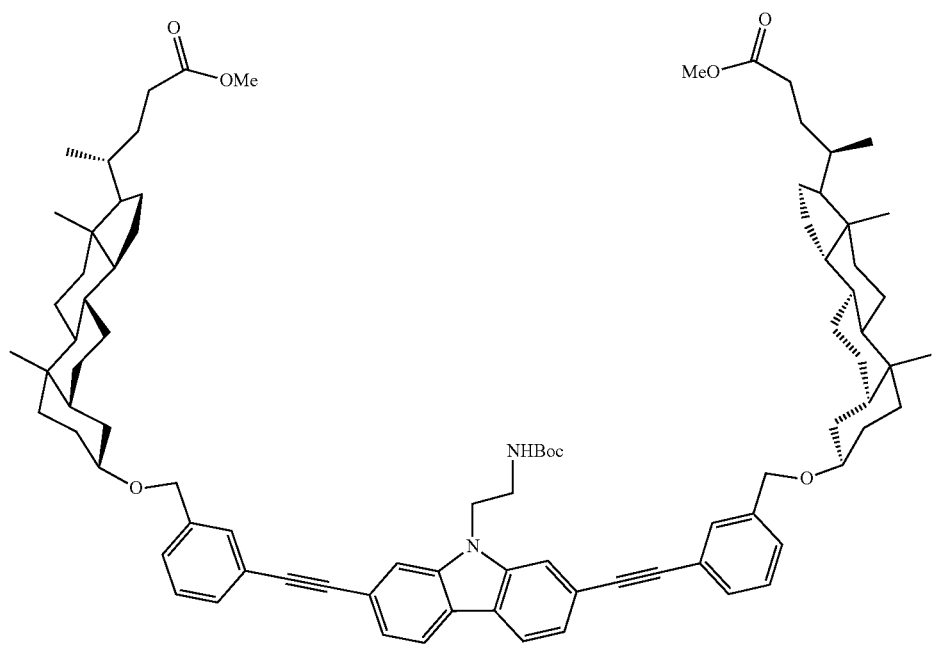
X12

(Compound 21)
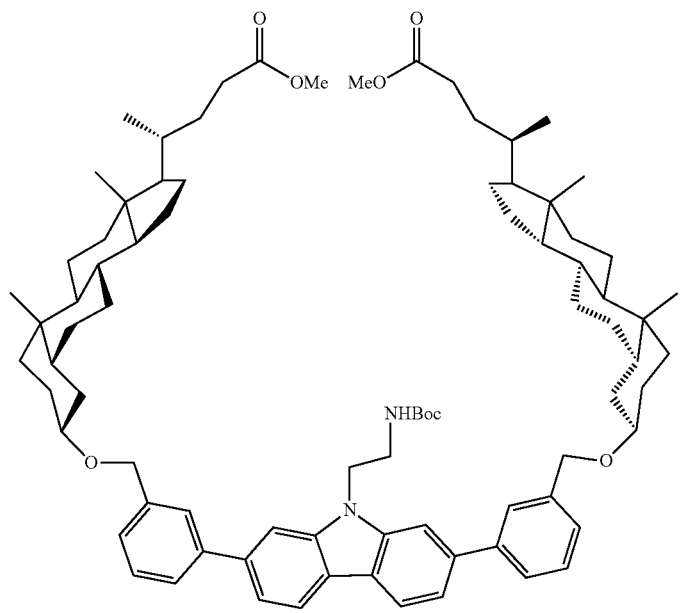
X14
(Compound 22)
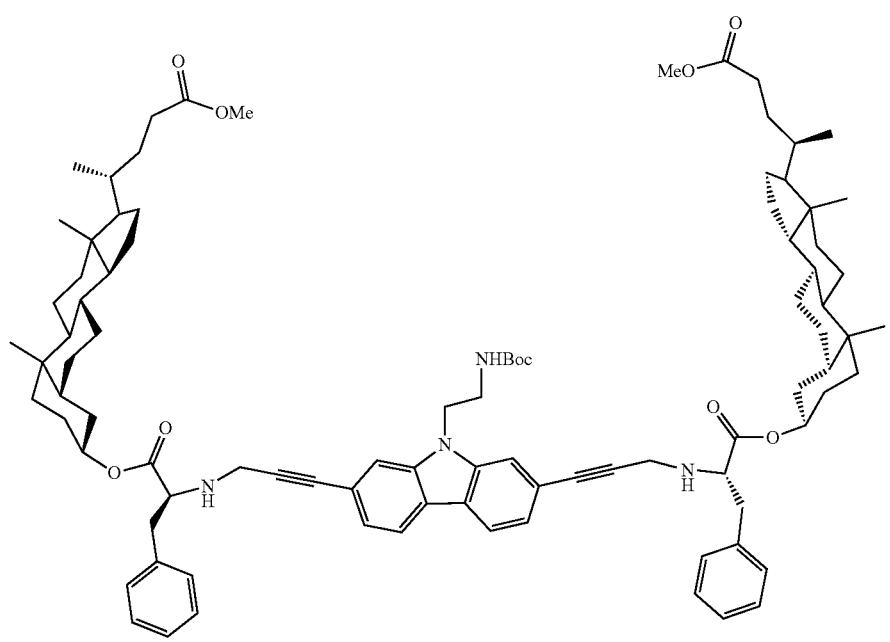
X18

(Compound 23)
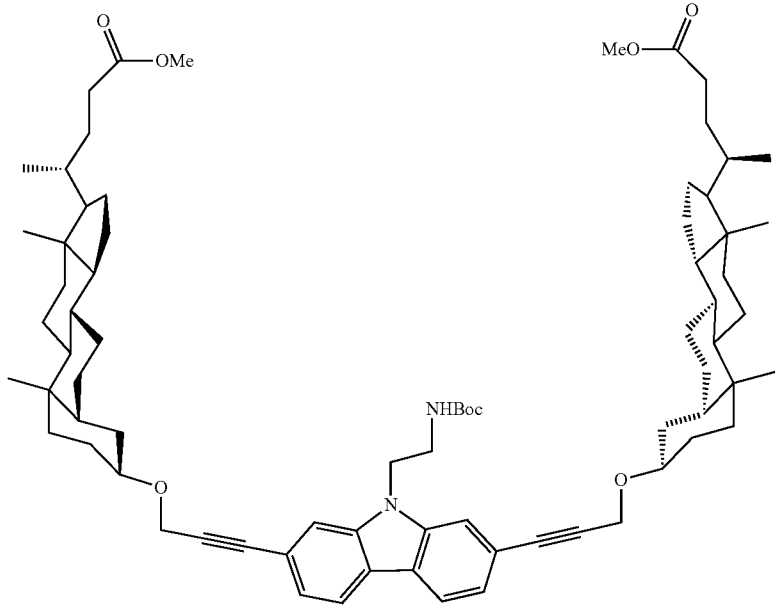
X25
(Compound 24)
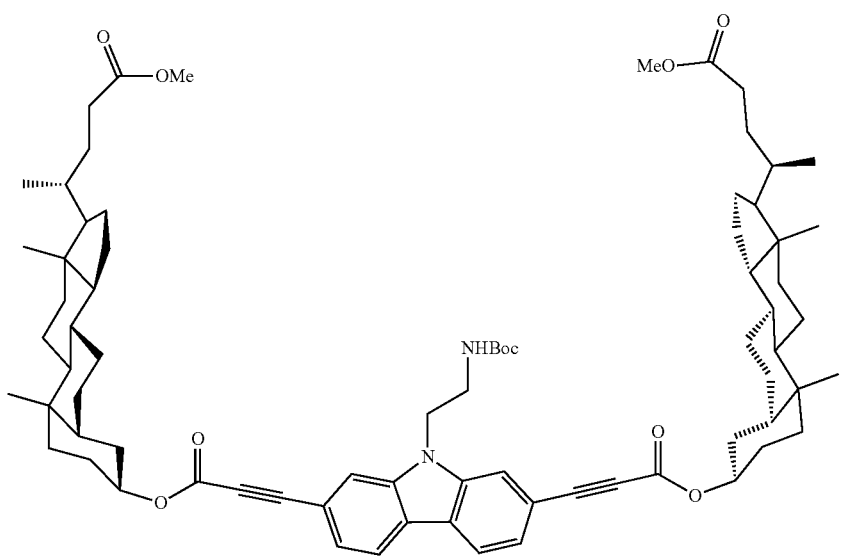
X23

-continued (Compound 25)

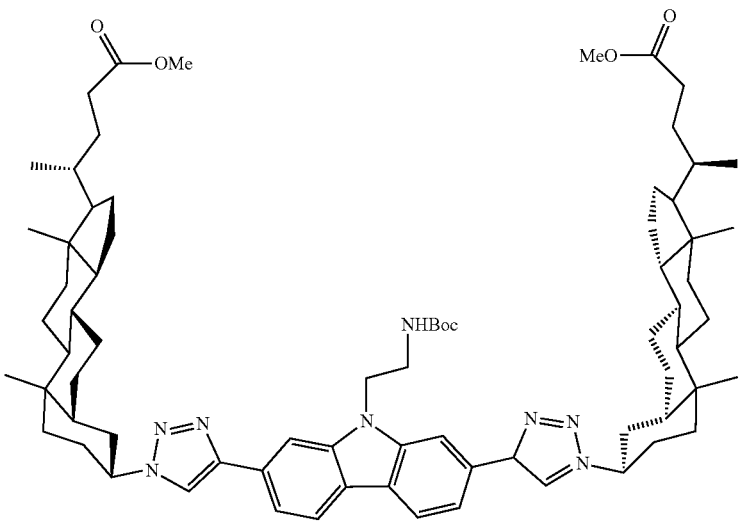

10. The compound of claim 1, wherein the ionophoric compound is selected from the group consisting of mycotoxins, beauvericin, enniatins, ionophoric polyether antibiotics, monensin A, salinomycin, emetic toxins, cereulide, bacterial ionophores, and valinomycin.

11. A pharmaceutical composition comprising a compound according to claim 1 and a pharmaceutically acceptable excipient or carrier.

12. A method for the treatment of at least one disease or disorder caused by an ionophoric compound, the method comprising:

administering to a subject in need thereof a therapeutically effective amount of a compound according to claim 1 or a pharmaceutical composition comprising the compound in combination with a pharmaceutically acceptable excipient or carrier.

13. The method of claim 12, wherein the subject is a human subject or a veterinary subject.

14. The method of claim 12, wherein the disease or disorder is a neurological disorder, a cancer, food poisoning, a heart disorder, or encephalopathy.

15. The method of claim 12, wherein the ionophoric compound is selected from the group consisting of mycotoxins, beauvericin, enniatins, ionophoric polyether antibiotics, monensin A, salinomycin, emetic toxins, cereulide, bacterial ionophores, and valinomycin.

16. A solid support having attached thereto a compound according to claim 1.

* * * * *